(12) United States Patent
Gilson et al.

(10) Patent No.: US 10,779,927 B2
(45) Date of Patent: Sep. 22, 2020

(54) VASCULAR FILTER DEVICE

(71) Applicant: Novate Medical Limited, Dublin (IE)

(72) Inventors: Paul Gilson, Galway (IE); Steven Horan, Galway (IE); Karl Keating, Galway (IE); Damien Ryan, Galway (IE); Jacqueline O'Gorman, County Clare (IE); Paul Bateman, Surrey (GB); Martin Keegan, Galway (IE); Declan Broderick, Cork (IE)

(73) Assignee: Novate Medical Limited, Galway (IE)

( * ) Notice: Subject to any disclaimer, the term of this patent is extended or adjusted under 35 U.S.C. 154(b) by 112 days.

(21) Appl. No.: 15/787,320

(22) Filed: Oct. 18, 2017

(65) Prior Publication Data
US 2018/0256308 A1 Sep. 13, 2018

Related U.S. Application Data

(63) Continuation of application No. 14/416,562, filed as application No. PCT/EP2013/065666 on Jul. 24, 2013, now abandoned.
(Continued)

(51) Int. Cl.
*A61F 2/01* (2006.01)
*A61F 2/86* (2013.01)

(52) U.S. Cl.
CPC ............... *A61F 2/01* (2013.01); *A61F 2/011* (2020.05); *A61F 2/86* (2013.01);
(Continued)

(58) Field of Classification Search
CPC ...... A61F 2/86; A61F 2/89; A61F 2230/0067; A61F 2230/0069
See application file for complete search history.

(56) References Cited

U.S. PATENT DOCUMENTS 8,057,507 B2 11/2011 Horan et al.
8,162,970 B2 4/2012 Gilson et al.
(Continued)

FOREIGN PATENT DOCUMENTS

EP 1733702 A2 12/2006
EP 2208479 B1 5/2012
(Continued)

OTHER PUBLICATIONS

International Preliminary Report on Patentability for corresponding International Application No. PCT/EP2013/065666 dated Jan. 27, 2015 (7 pages).
(Continued)

*Primary Examiner* — Ashley L Fishback
(74) *Attorney, Agent, or Firm* — Seager, Tufte & Wickhem LLP

(57) ABSTRACT

A vascular filter device (1) has a support frame (2) and filter elements (4). The filter elements (4) extend from the support frame towards filter element ends forming an on-axis apex (5) at which they are interconnected by a holder (6). The filter elements (4) are biased such that if unconnected the filter element ends are located between the support frame and said central axis when the vascular filter device is unconstrained. The filter element unconnected positions are provided by the filter element shapes and the angles at which they extend from the support frame, and in one example this is achieved by laser cutting tubing and heat setting the material.

20 Claims, 70 Drawing Sheets

Related U.S. Application Data

(60) Provisional application No. 61/675,515, filed on Jul. 25, 2012.

(52) U.S. Cl.
CPC ... *A61F 2002/016* (2013.01); *A61F 2210/009* (2013.01); *A61F 2230/005* (2013.01); *A61F 2230/0017* (2013.01); *A61F 2230/0067* (2013.01); *A61F 2230/0069* (2013.01); *A61F 2250/006* (2013.01); *Y10T 83/0596* (2015.04)

(56) References Cited

U.S. PATENT DOCUMENTS

| 8,443,854 | B2 | 5/2013 | Long |
| 8,647,360 | B2 | 2/2014 | Gilson et al. |
| 8,668,713 | B2 | 3/2014 | Horan et al. |
| 8,821,530 | B2 | 9/2014 | Horan et al. |
| 2003/0004536 | A1 | 1/2003 | Boylan et al. |
| 2003/0195607 | A1 | 10/2003 | Trout et al. |
| 2007/0112372 | A1 | 5/2007 | Sosnowski et al. |
| 2010/0185230 | A1 | 7/2010 | Horan et al. |
| 2010/0228281 | A1 | 9/2010 | Gilson et al. |
| 2011/0054519 | A1 | 3/2011 | Neuss |
| 2012/0029552 | A1 | 2/2012 | Horan et al. |
| 2012/0245620 | A1 | 9/2012 | Gilson et al. |
| 2014/0207176 | A1 | 7/2014 | Gilson et al. |
| 2014/0207177 | A1 | 7/2014 | Horan et al. |
| 2015/0025565 | A1 | 1/2015 | Horan et al. |

FOREIGN PATENT DOCUMENTS

| JP | 2006255428 A | 9/2006 |
| WO | 2008010197 A2 | 1/2008 |
| WO | 2010025775 A1 | 3/2010 |

OTHER PUBLICATIONS

International Search Report for corresponding International Application No. PCT/EP2013/065666 dated Oct. 29, 2013 (3 pages).

Rogers, MD, Frederick B., "Five-Year Follow-Up of Prophylactic Vena Cava Filters in High-Risk Trauma Patients," Arch Surg, vol. 133, Apr. 1998, pp. 406-411.

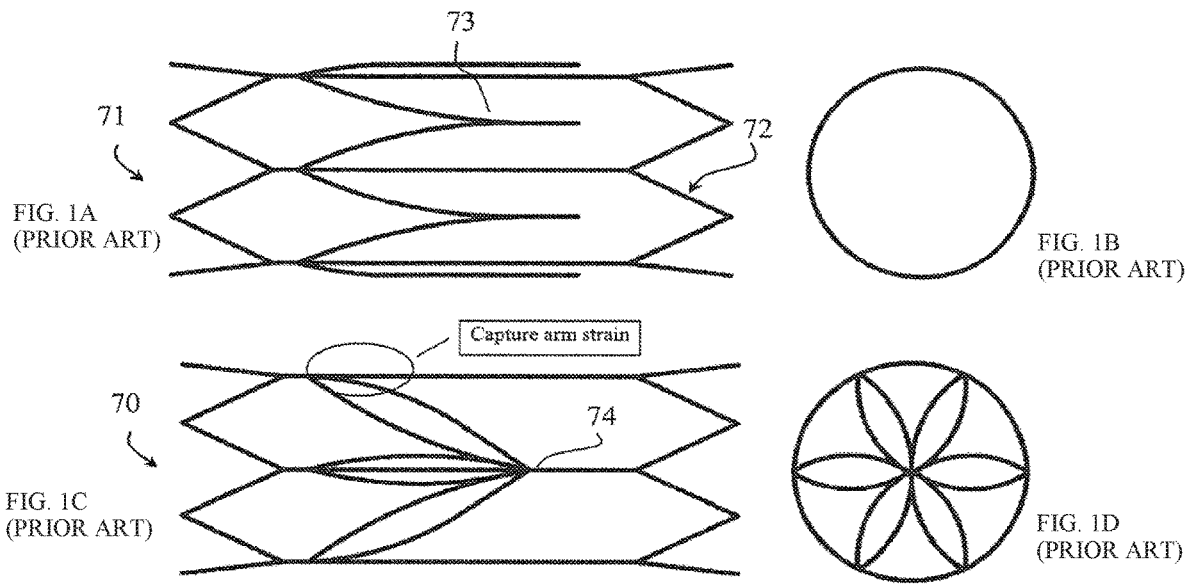
FIG. 1A (PRIOR ART)
FIG. 1B (PRIOR ART)
FIG. 1C (PRIOR ART)
FIG. 1D (PRIOR ART)
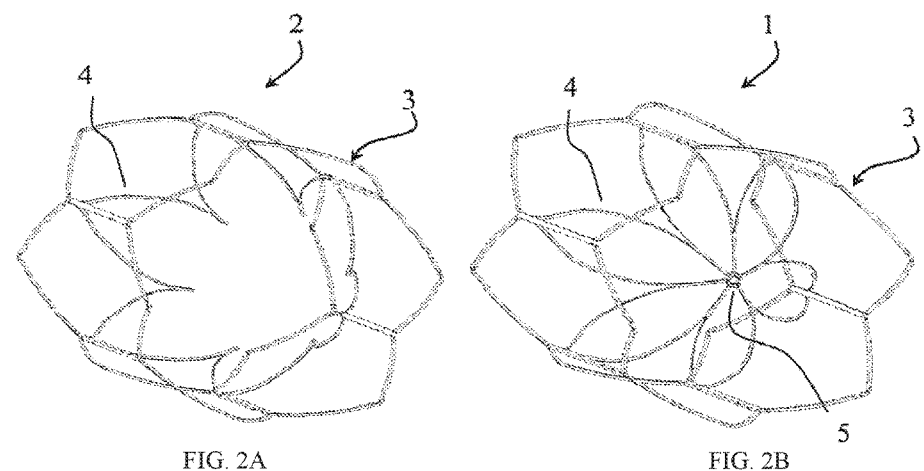
FIG. 2A
FIG. 2B

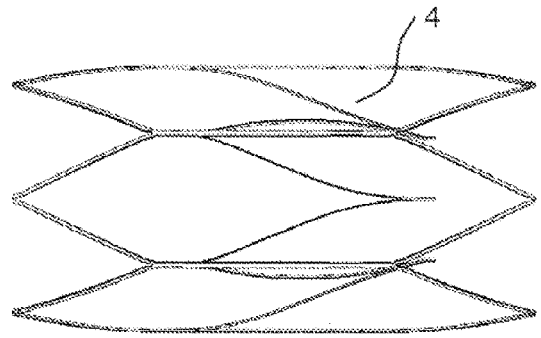
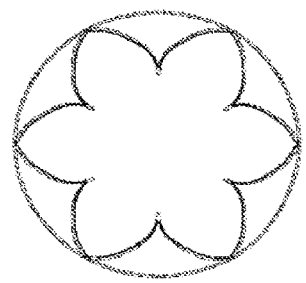
FIG. 3A
FIG. 3B
FIG. 3C
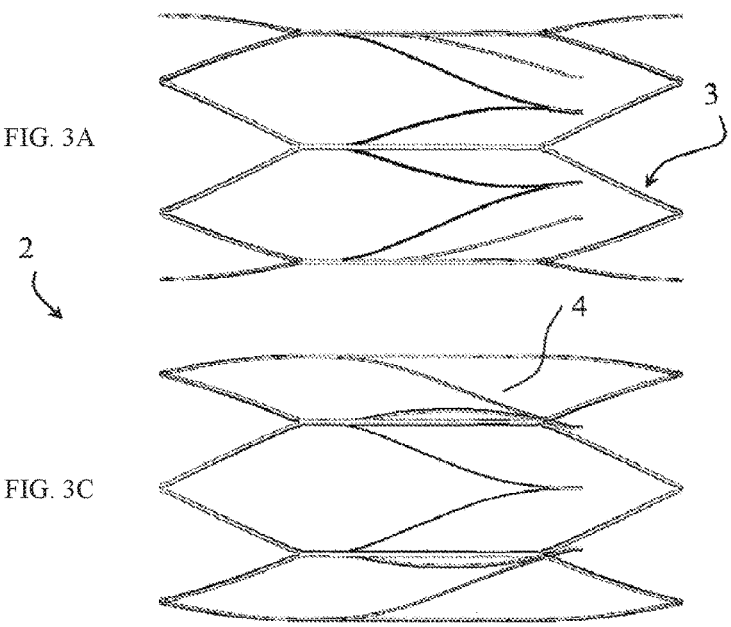
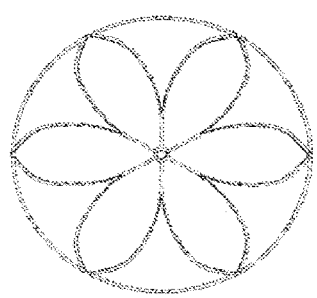
FIG. 4A
FIG. 4B
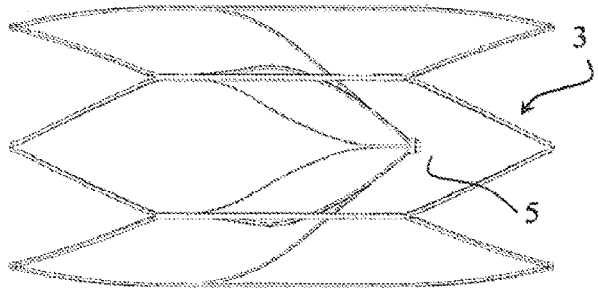
FIG. 4C

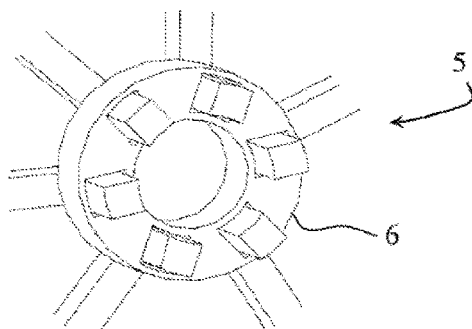
Fig 5
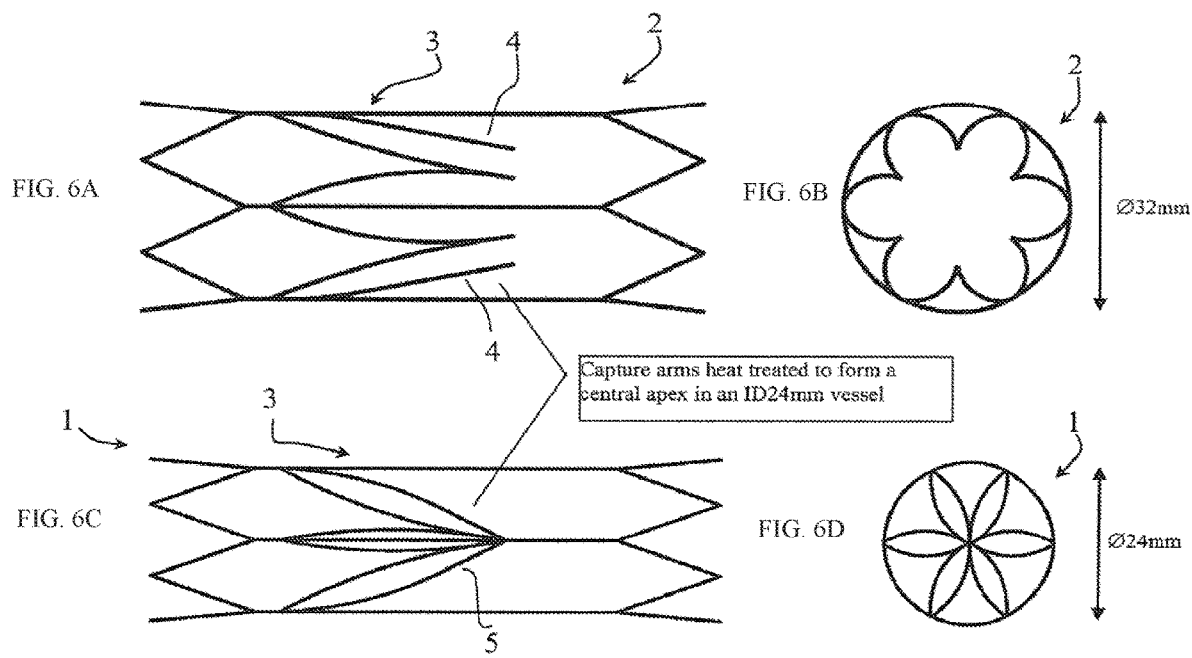

SECTION A-A

SECTION B-B

Straight connectors 210

DETAIL E
SCALE 10 : 1

Straight connectors 210

211
Proximal peak of distal support hoop

DETAIL F
SCALE 10 : 1

212
Distal peak of distal support hoop

DETAIL G
SCALE 10 : 1

205 Proximal peaks of proximal support hoop

DETAIL A
SCALE 10 : 1

206 Distal peaks of proximal support hoop

Filter elements

Straight connectors

DETAIL B
SCALE 10 : 1

208 Straight connectors

207 Filter elements

DETAIL C
SCALE 10 : 1

207 Filter elements

209 Integral apex

DETAIL D
SCALE 10 : 1

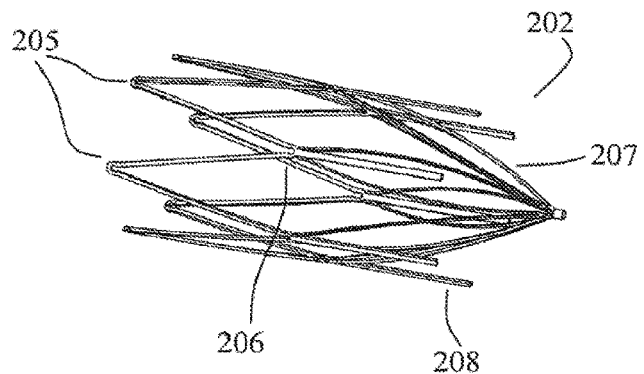
FIG. 23A
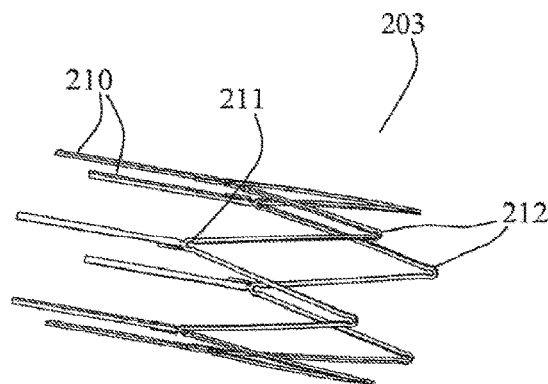
FIG. 23B
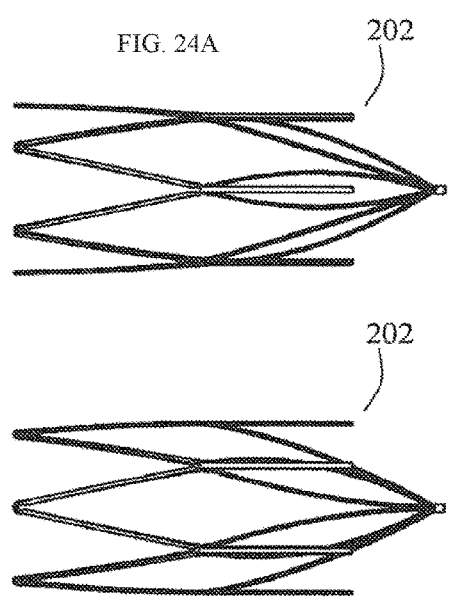
FIG. 24A
FIG. 24C
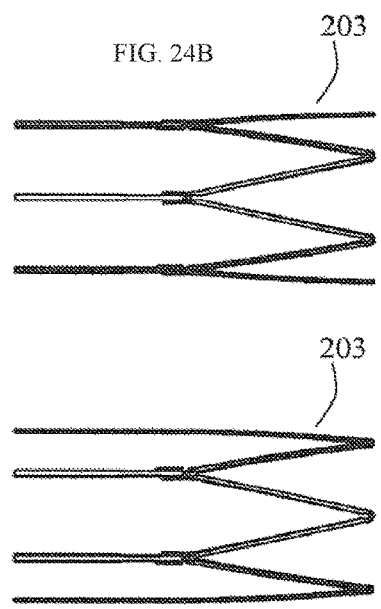
FIG. 24B
FIG. 24D

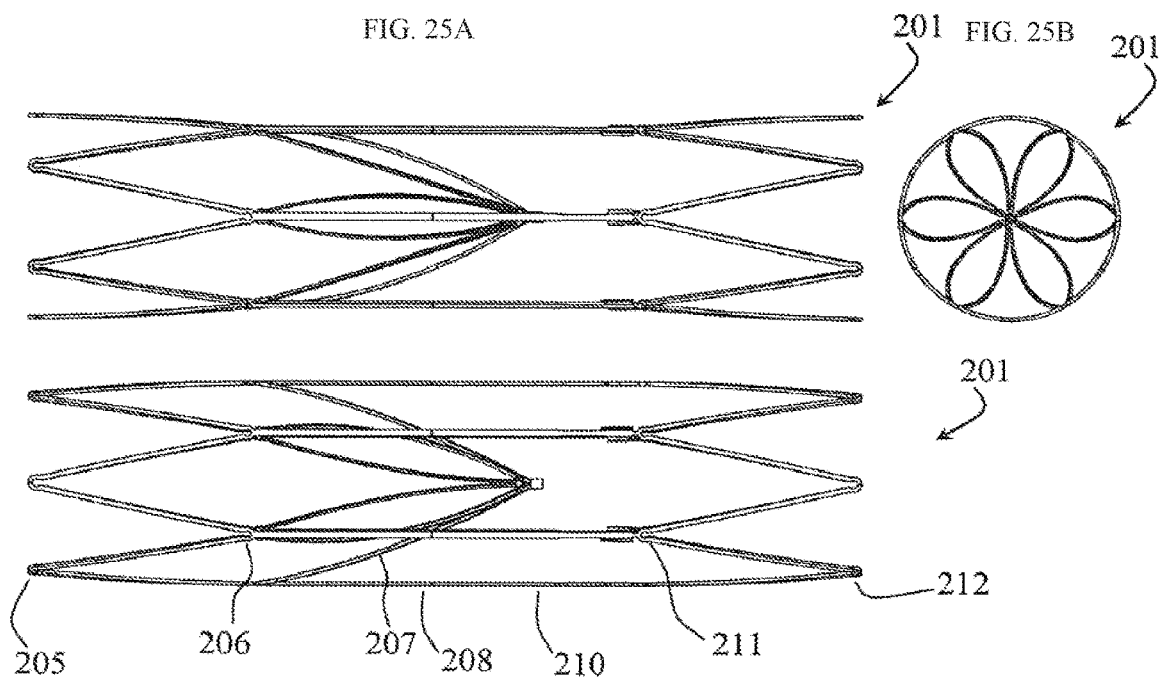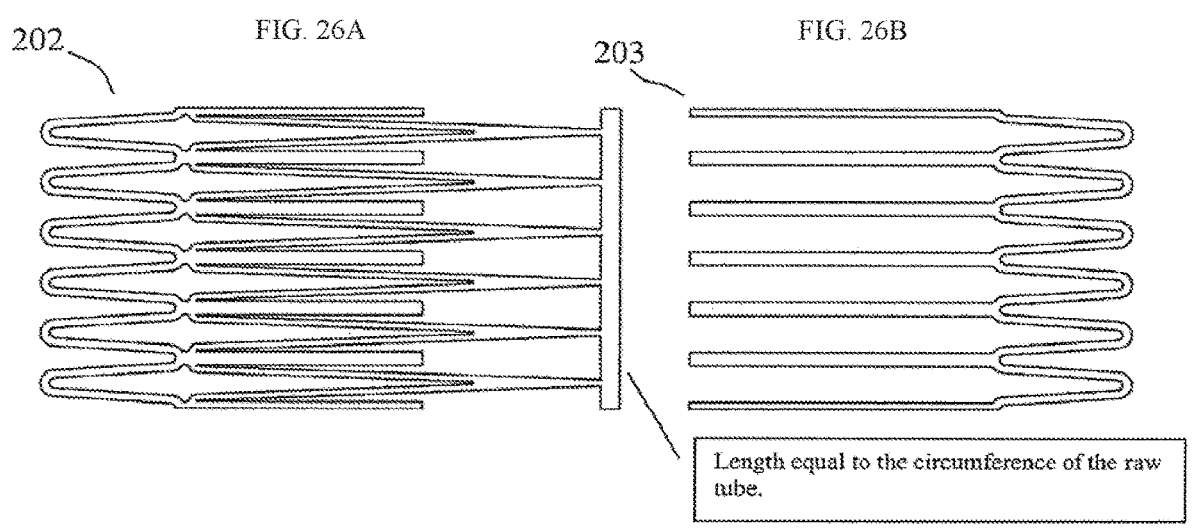

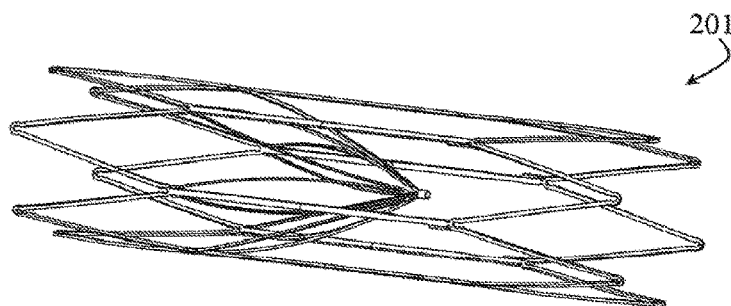
FIG. 27A
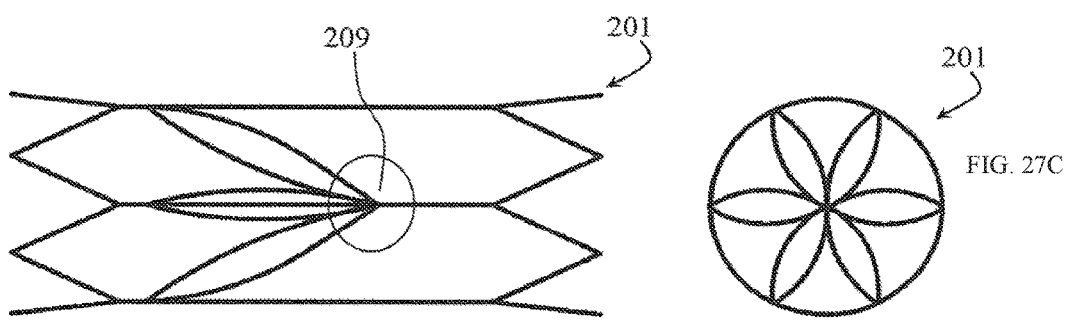
FIG. 27B
FIG. 27C
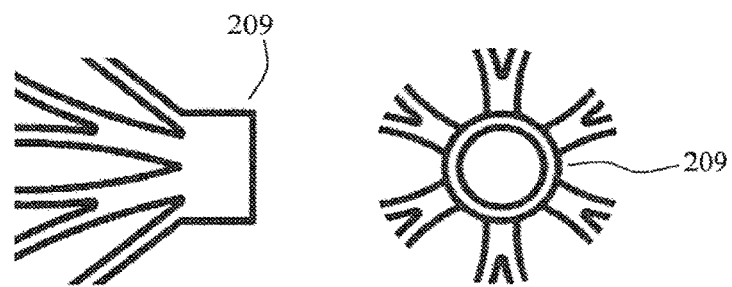
FIG. 27D
FIG. 27E
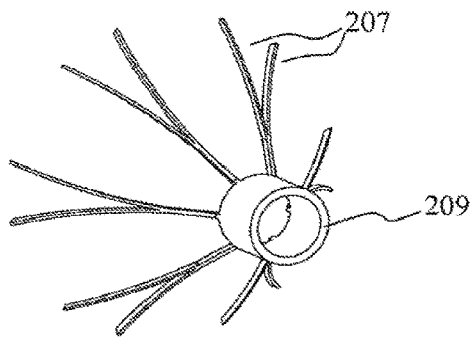
FIG. 27F

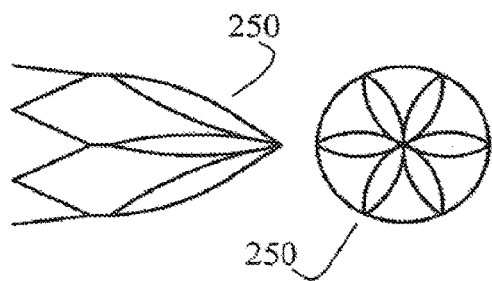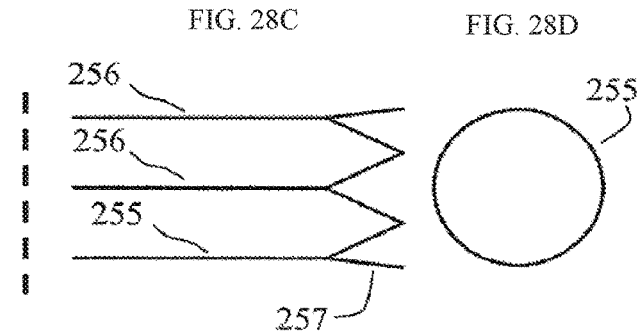
FIG. 28A  FIG. 28B  FIG. 28C  FIG. 28D
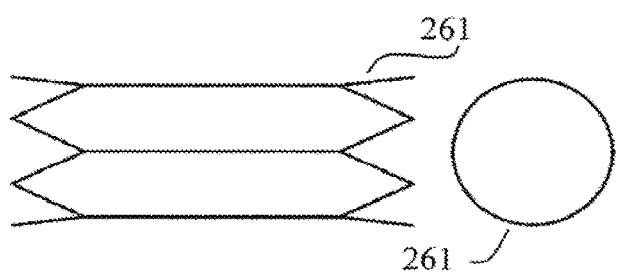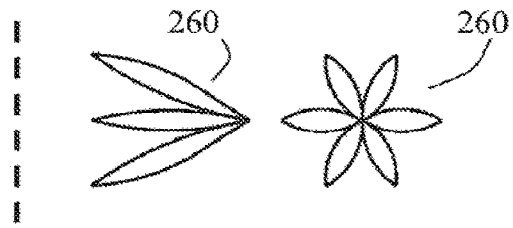
FIG. 28E  FIG. 28F  FIG. 28G  FIG. 28H
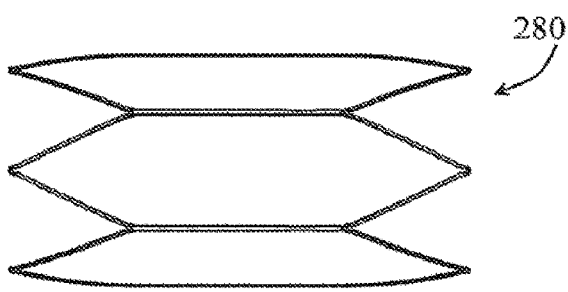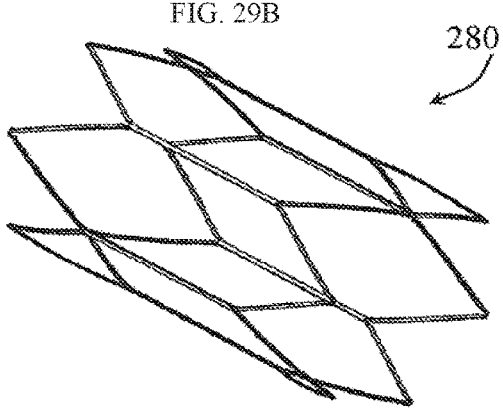
FIG. 29A  FIG. 29B
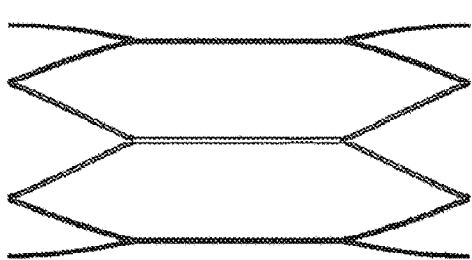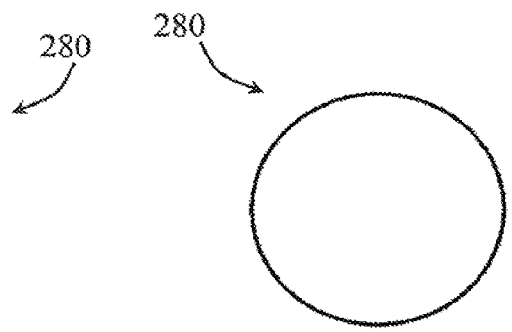
FIG. 29C  FIG. 29D

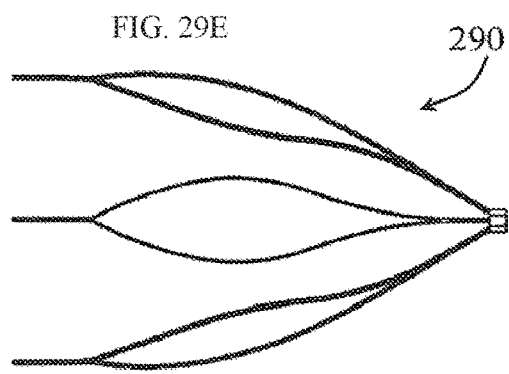
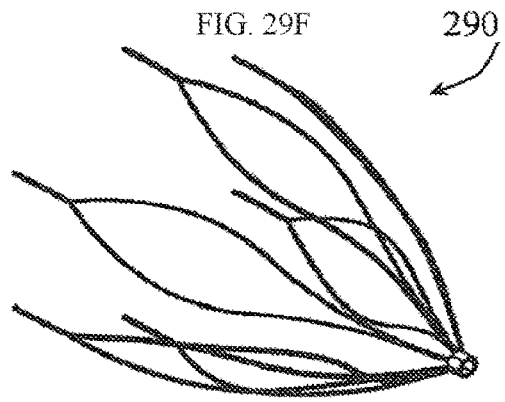
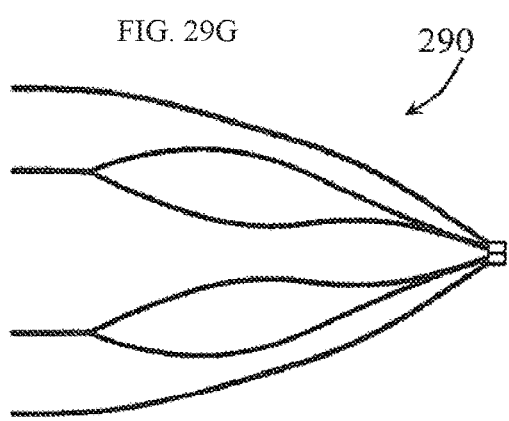
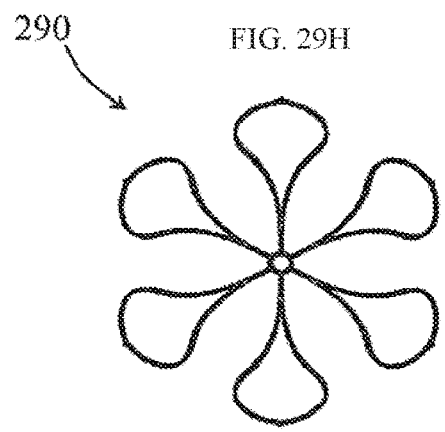
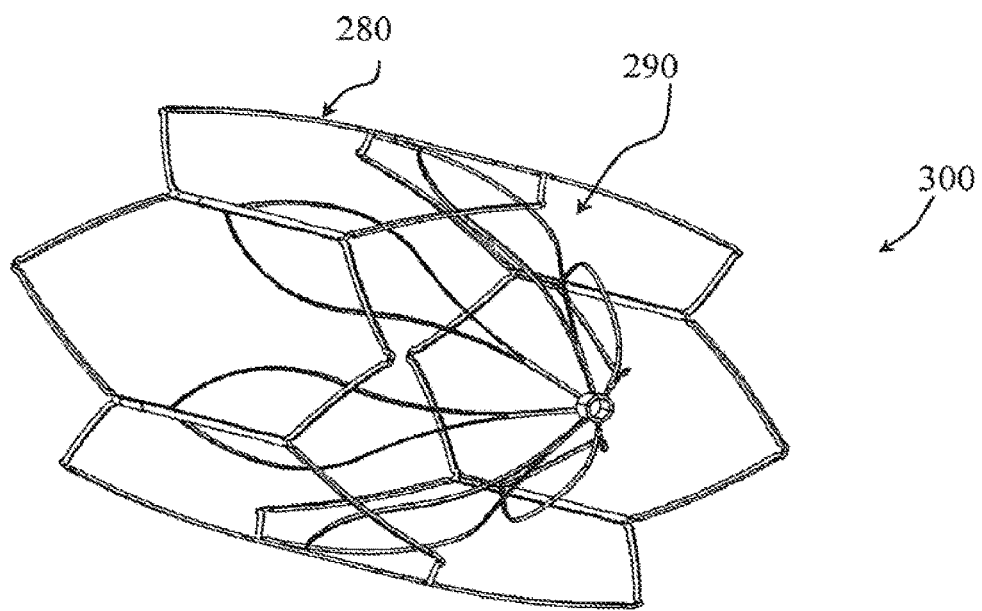
Fig. 30

FIG. 31A
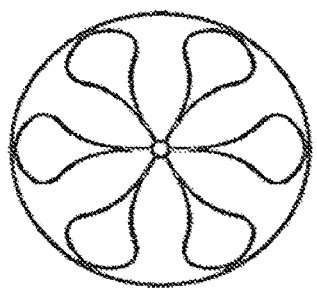
FIG. 31B
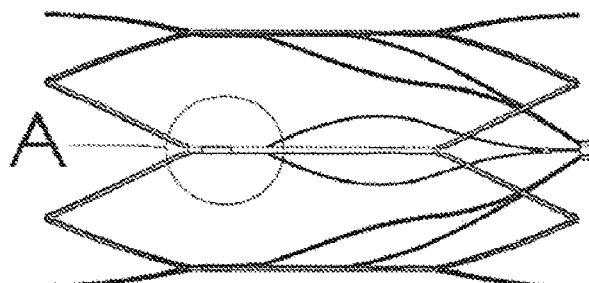
FIG. 31C
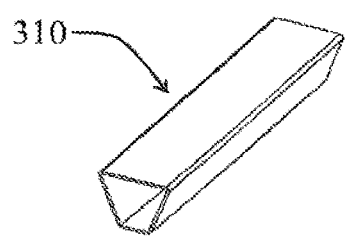
310
FIG. 31D
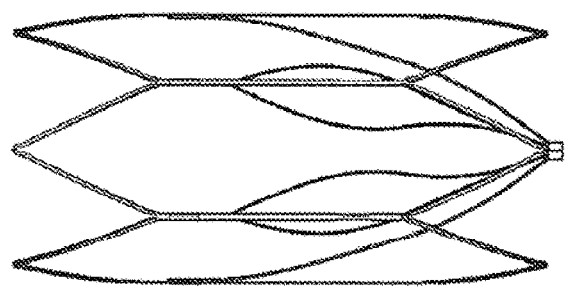
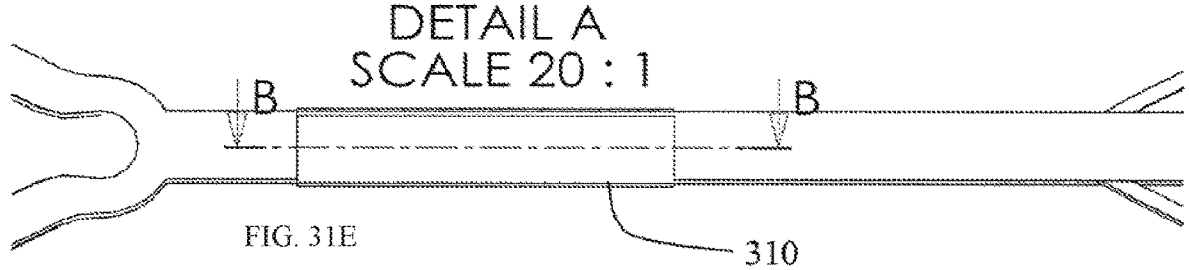
DETAIL A
SCALE 20 : 1
FIG. 31E
310
SECTION B-B
SCALE 20 : 1
FIG. 31F

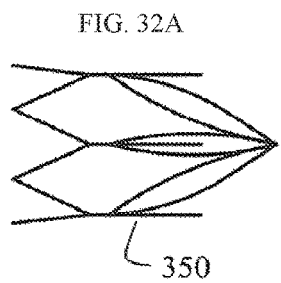 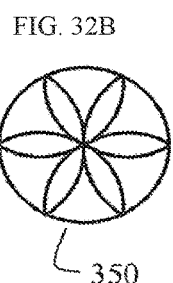 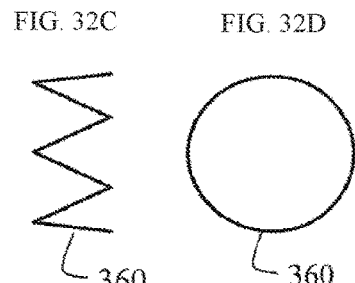 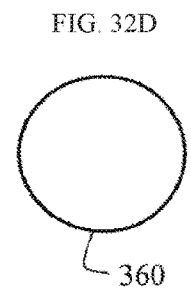
FIG. 32A  FIG. 32B  FIG. 32C  FIG. 32D
Fig. 32
 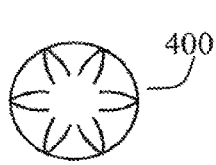  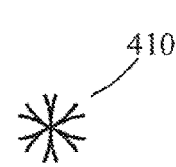
FIG. 33A  FIG. 33B  FIG. 33C  FIG. 33D
FIG. 34A 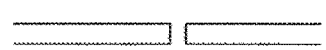  FIG. 34G
FIG. 34B  FIG. 34H
FIG. 34C   FIG. 34I
FIG. 34D  FIG. 34J
FIG. 34E 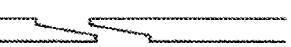 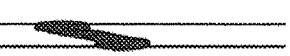 FIG. 34K
FIG. 34F  FIG. 34L

Fig. 43
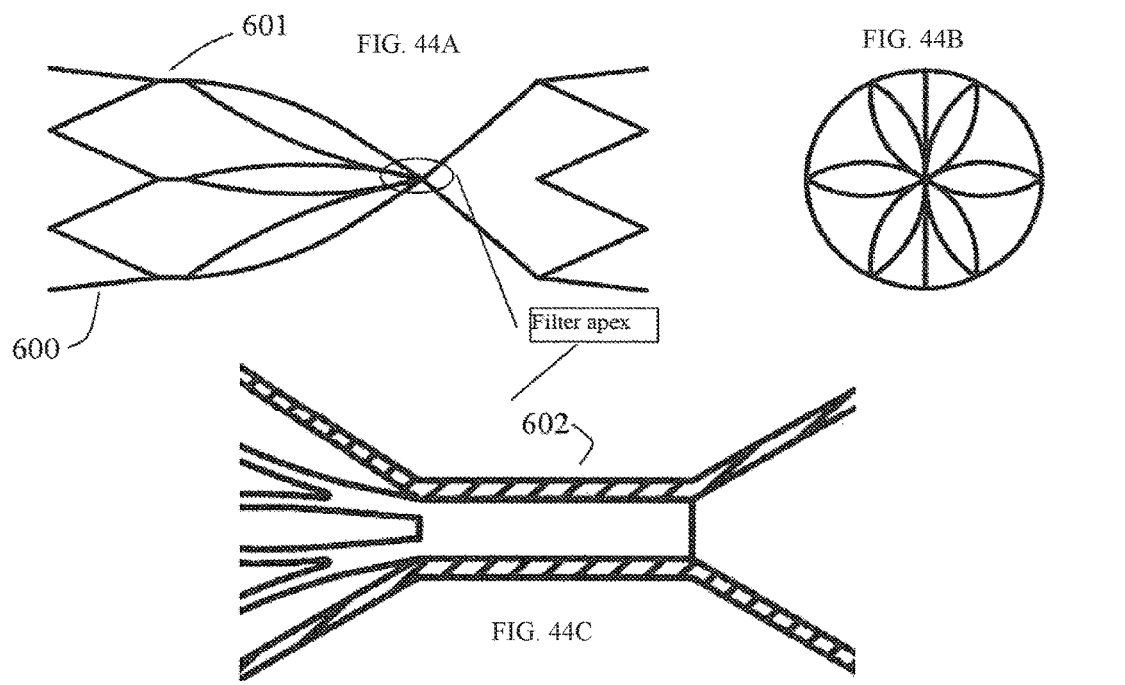
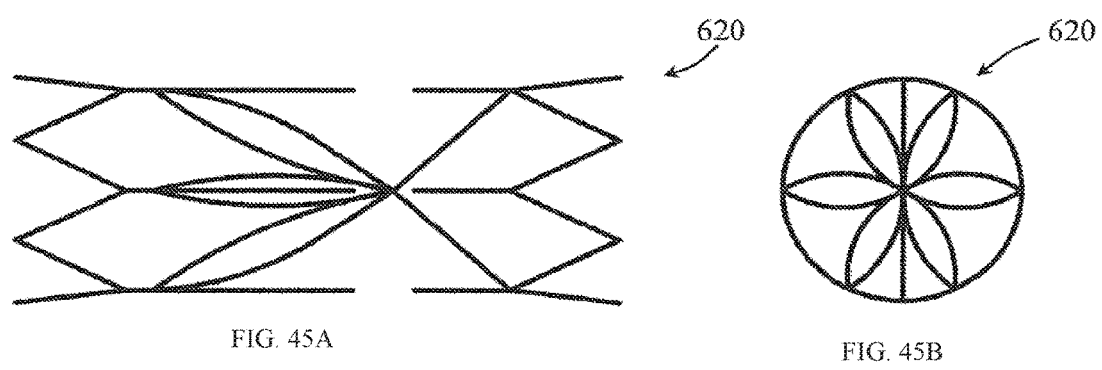

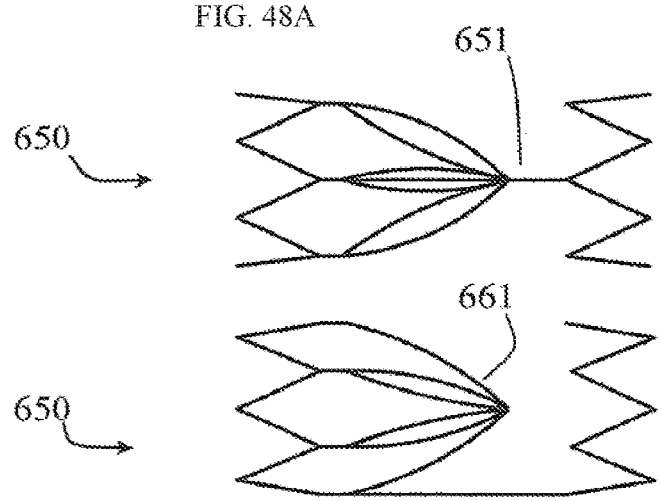
FIG. 48A
FIG. 48C
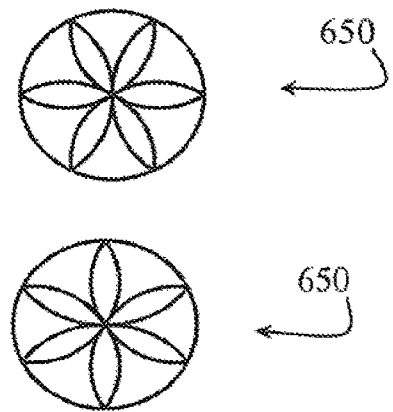
FIG. 48B
FIG. 48D
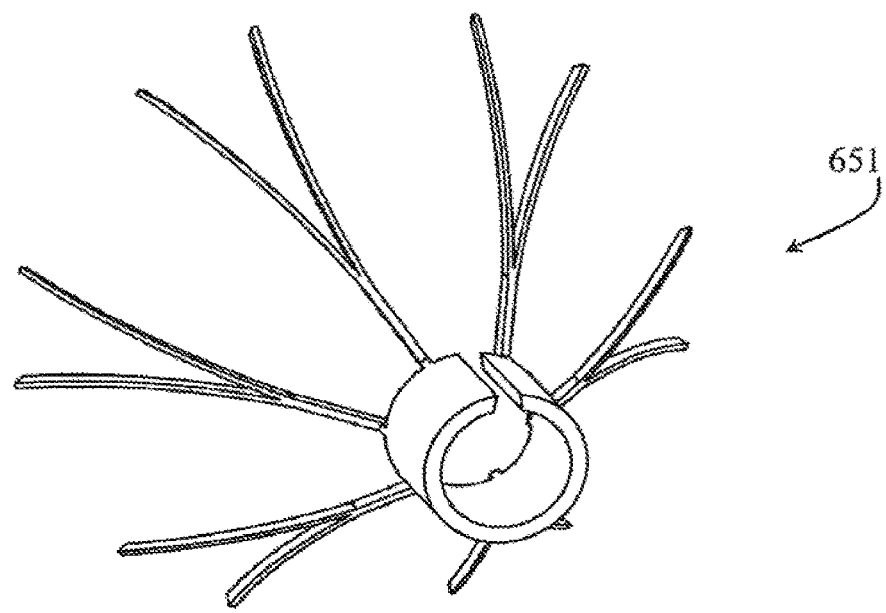
FIG. 48E FIG. 49A 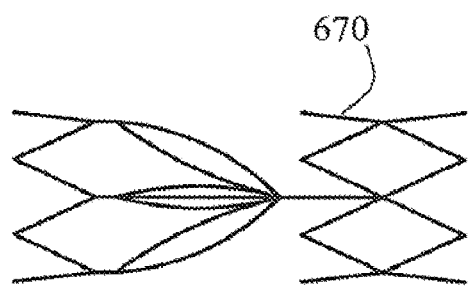 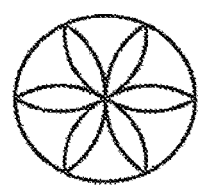 FIG. 49B
FIG. 49C 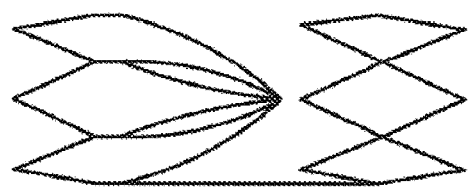 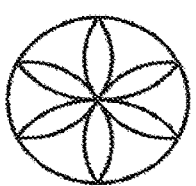 FIG. 49D
FIG. 50A
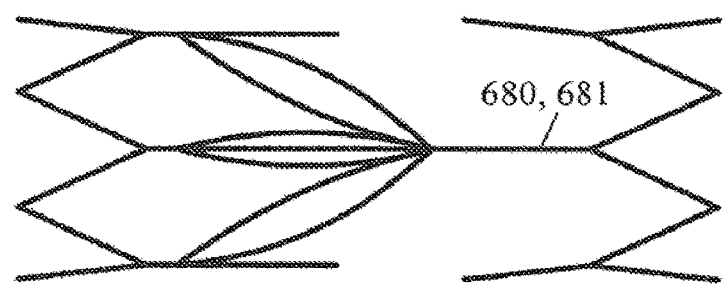 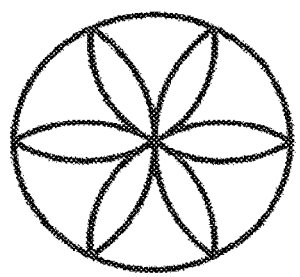
FIG. 50B
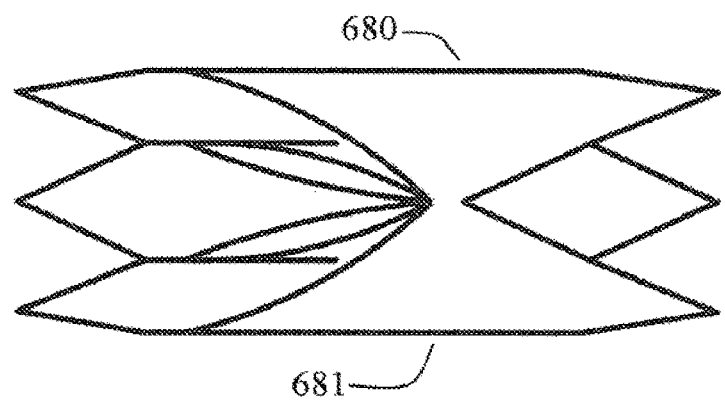 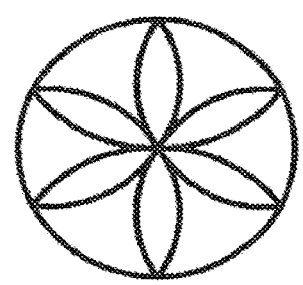
FIG. 50C
FIG. 50D

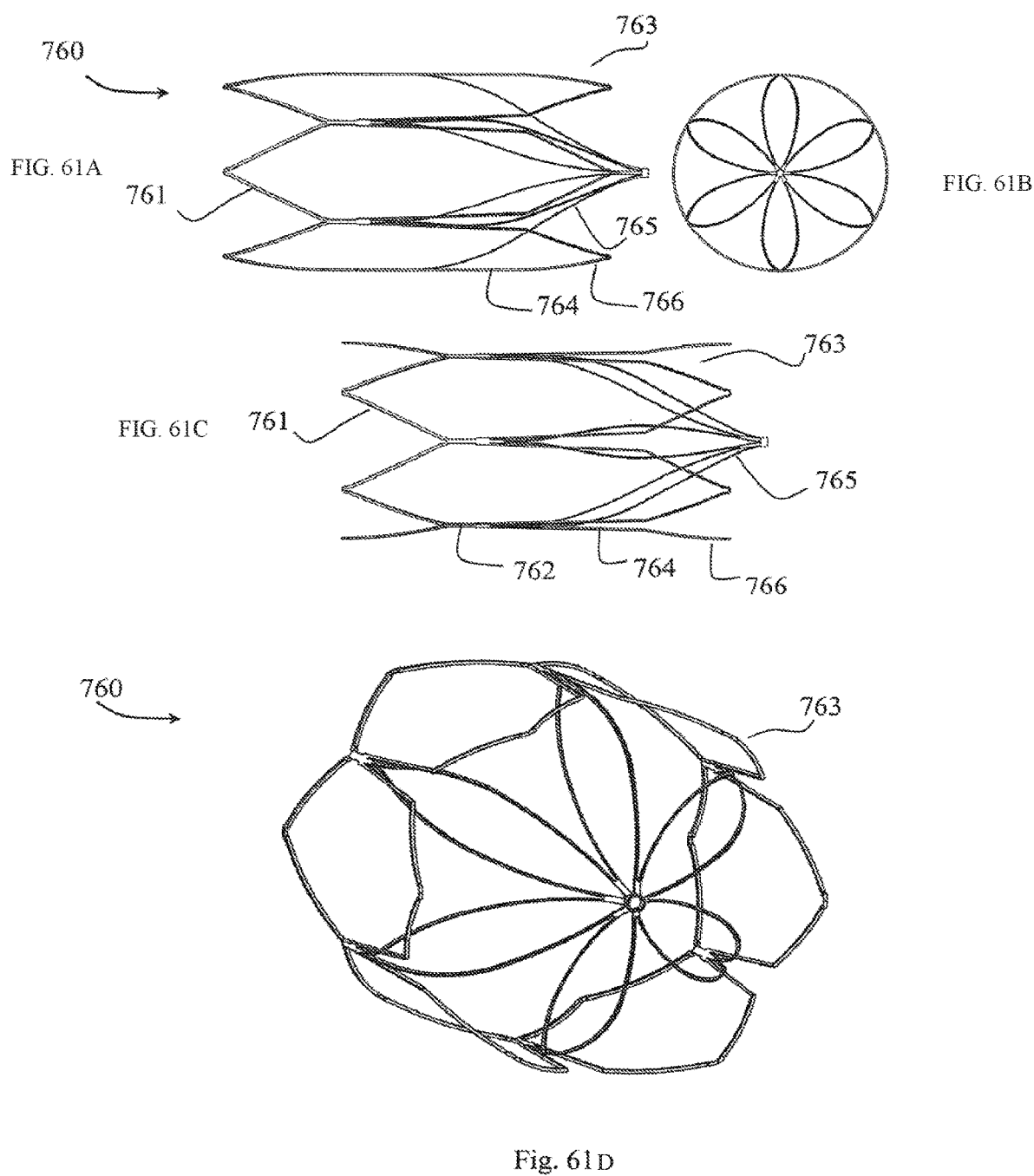

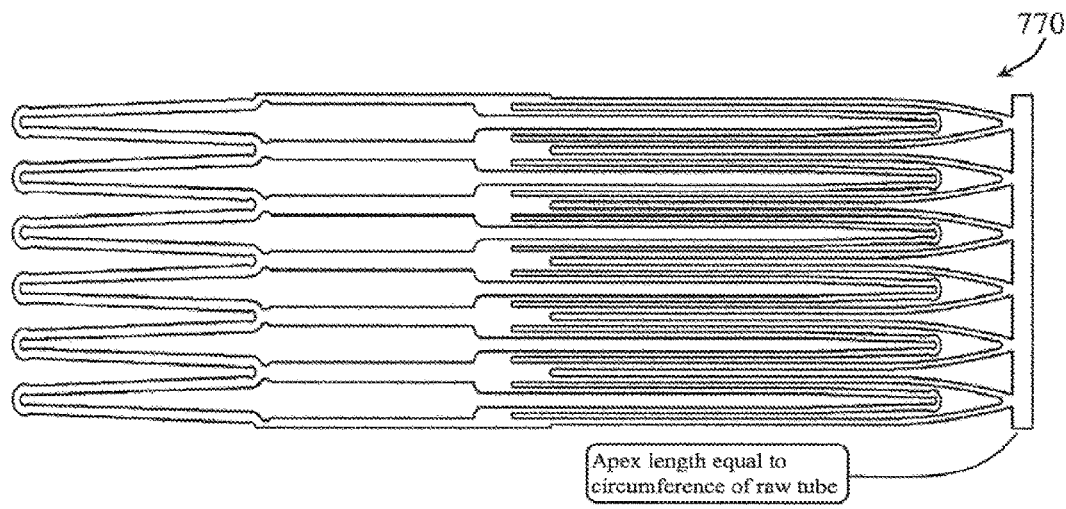
Fig. 63
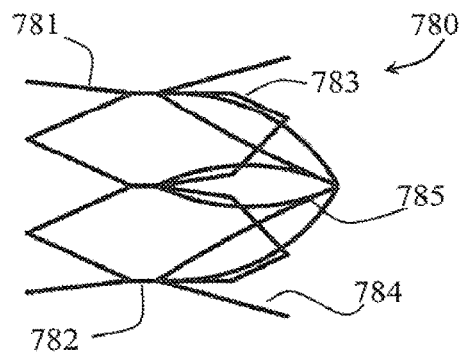
FIG. 64A
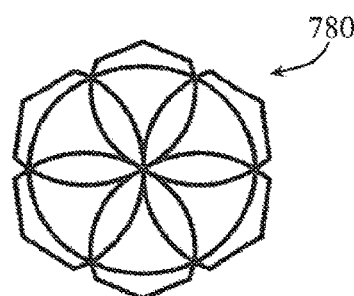
FIG. 64B
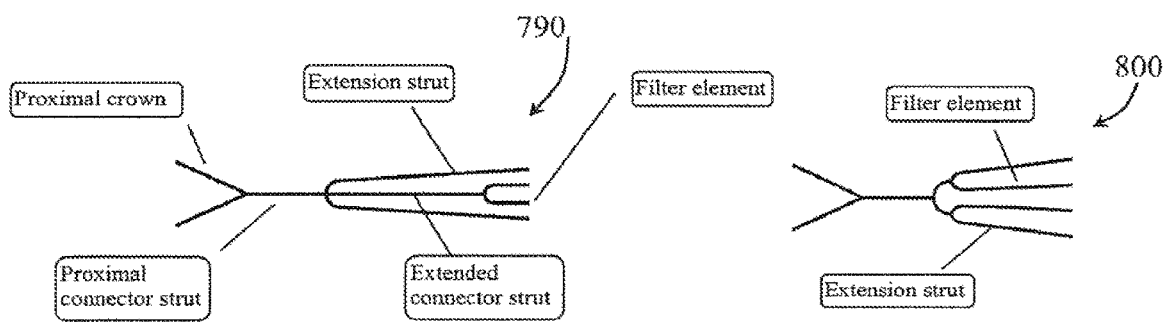
FIG. 65A
FIG. 65B

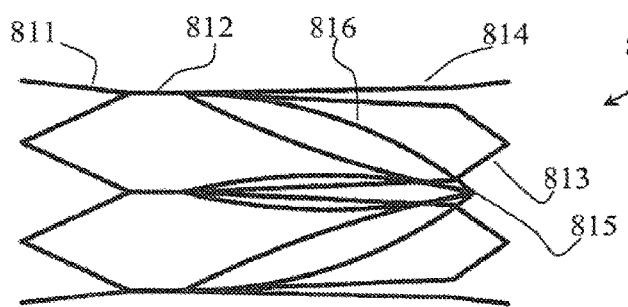
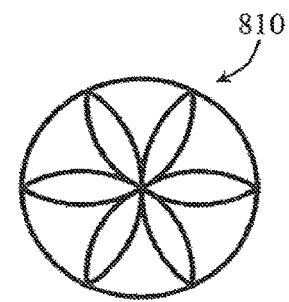
FIG. 66A  FIG. 66B
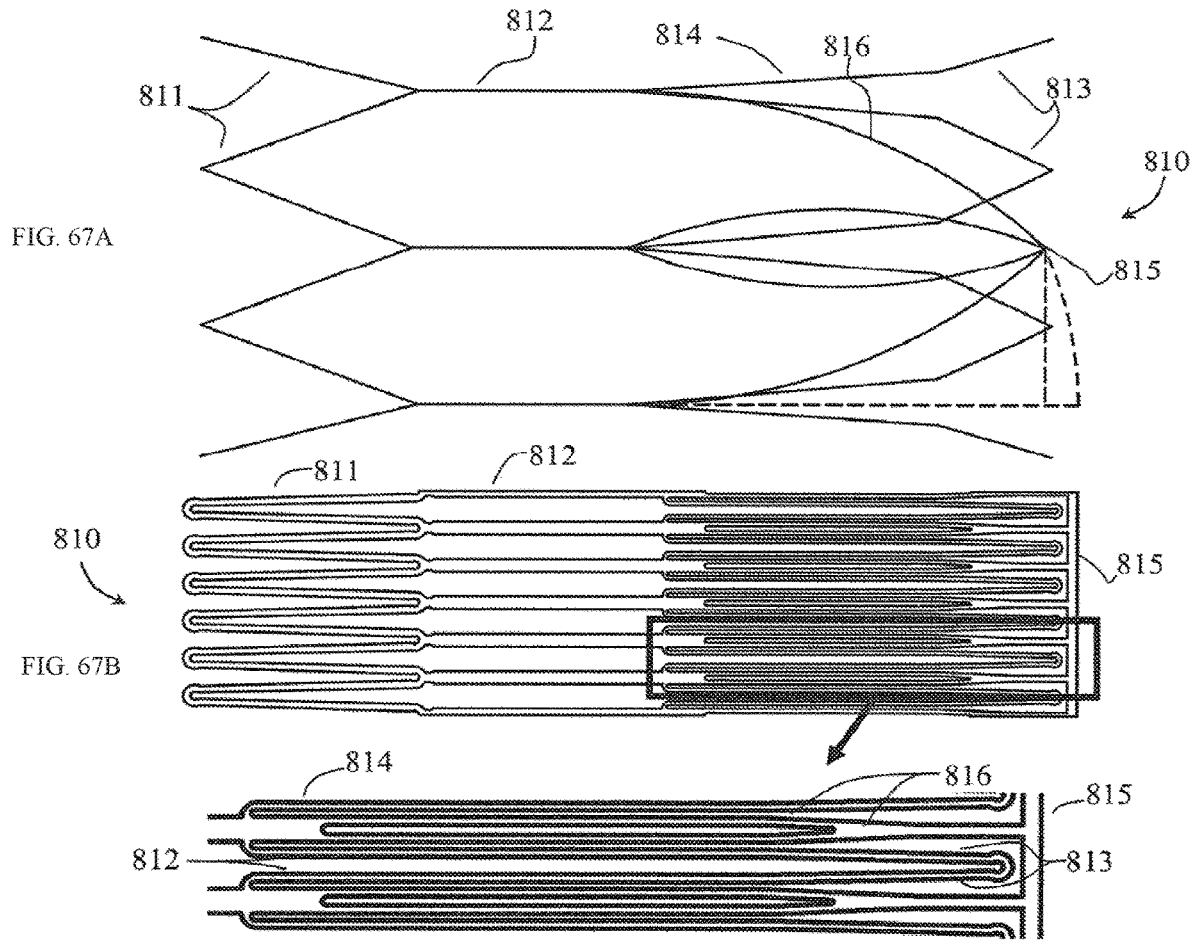
FIG. 67A
FIG. 67B
Fig. 67C

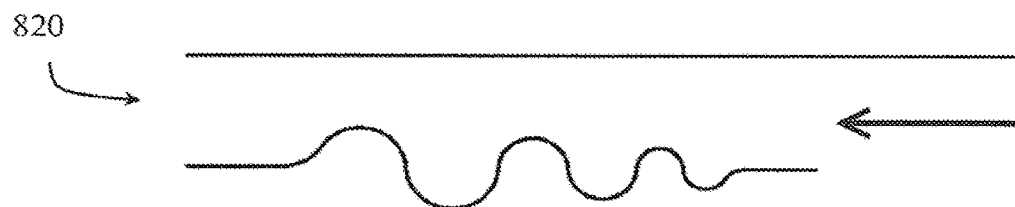
Fig. 68
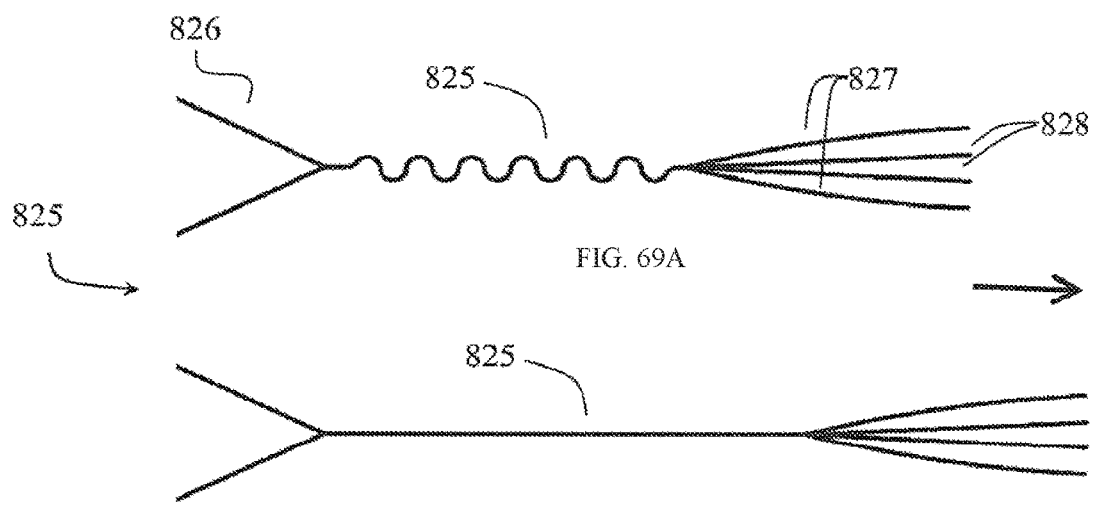
FIG. 69A
Fig. 69 B
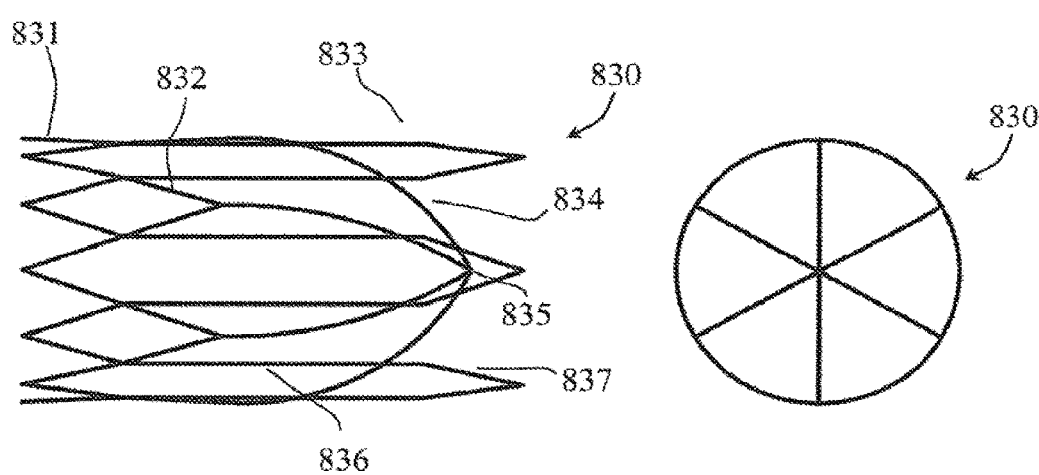
FIG. 70A
FIG. 70B

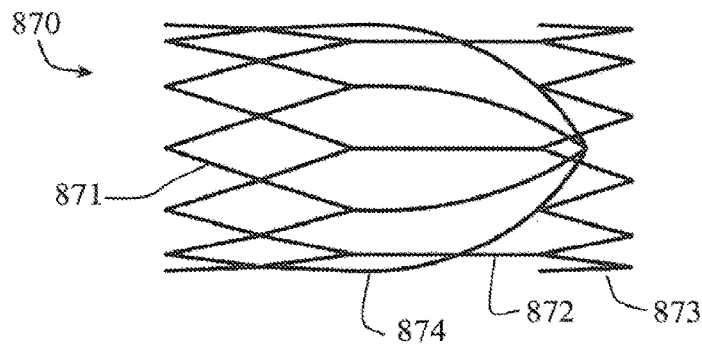
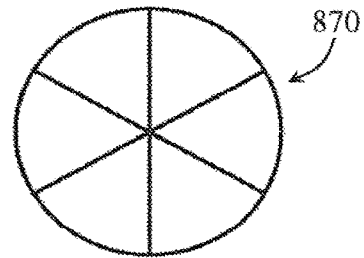
FIG. 74A
FIG. 74B
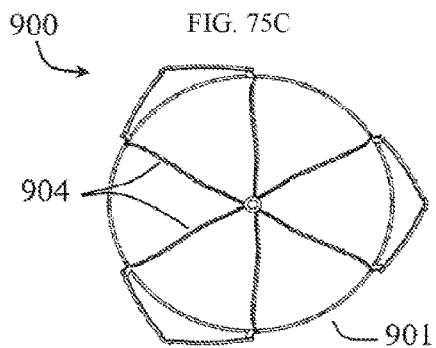
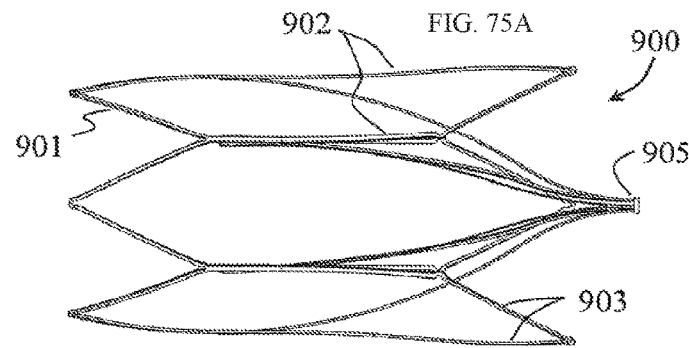
FIG. 75C
FIG. 75A
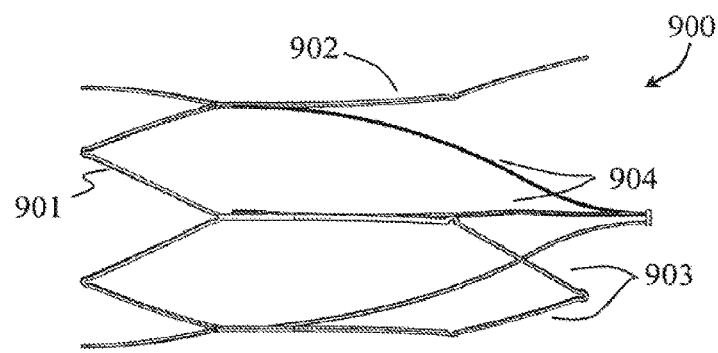
Fig. 75B ized patent application Ser. No. 14/416,562, filed on Jan. 22, 2015, which is a National Stage Entry of International Application No. PCT/EP2013/065666, filed on Jul. 24, 2013, which claims priority to U.S. Provisional Patent Application No. 61/675,515, filed on Jul. 25, 2012, the entireties of each of which is incorporated herein by reference.

VASCULAR FILTER DEVICE

CROSS REFERENCE TO RELATED APPLICATION(S)

This patent application is a continuation of U.S. Nonprovisional patent application Ser. No. 14/416,562, filed on Jan. 22, 2015, which is a National Stage Entry of International Application No. PCT/EP2013/065666, filed on Jul. 24, 2013, which claims priority to U.S. Provisional Patent Application No. 61/675,515, filed on Jul. 25, 2012, the entireties of each of which is incorporated herein by reference.

INTRODUCTION

The invention relates to a vascular filter of the type comprising a support and a filter with filter elements connected at one end to the support and being interconnected at the other end. A typical example is convergence of the filter elements in an apex. Examples are described in our prior patent specification numbers WO2008/010197, EP2208479, WO2010/082187, and US20100185227. In these examples the support comprises a proximal hoop and a distal hoop and interconnecting struts between the hoops.

Many currently available devices are variations of a conical filter design that are prone to tilting as they have limited longitudinal support. Other variations include a design where a conical filter is supported caudally with an annular ring, such a design is also prone to tilting as it has limited longitudinal support. This understanding is supported in clinical literature; reference Rogers, F. B., et al, Five-year follow-up of prophylactic vena cava filters in high-risk trauma patients. Arch Surg, 1998. 133(4): p. 406-11; discussion 412. Upon advancement from a femoral approach, vascular geometry forces the delivery catheter tip against the wall of the vena cava. During deployment, the apex of the conical filter is released first and is free to point into or along the vessel wall (i.e. the filter is in a tilted position during deployment). The filter does not expand until its most caudal end is released from the catheter. This instantaneous expansion causes the filter to assume the tilted position of the delivery catheter. FIGS. 1A and 1B show a representation of a prior art device (70) such as that illustrated in FIG. 52(j) of WO2008/010197. It has a support (72) and filter elements (73) which are formed to extend longitudinally. The filter elements (73) are pulled radially inwardly and are interconnected through the use of a holder. Prior art device in FIG. 4 of US20100185227 is also similar with proximal support, distal support, a plurality of support struts extending between the proximal and distal supports, and a plurality of filter elements interconnected with a holder. The filter elements are cantilevers and strain is produced at their connection to the support when pulled radially inwardly. The filter element strain is highest when the filter is constrained in the largest indicated vessel and reduces when constrained in smaller diameter vessels. The invention is directed towards reducing strain between the filter elements and the support.

Another object is to reduce risk of fibrin growth and/or thrombus formation at the filter element interconnection.

SUMMARY OF THE INVENTION

In the invention, the vascular filter device has a support structure which is preferably stent-like in overall configuration, and preferably has proximal and distal supports linked by connecting struts. The device preferably has a filter with filter elements connected to the support at one end and converging at the other end. In some embodiments they converge at an apex. The area of convergence may be interconnected using a variety of coupling means or the area of convergence may be integral with at least some of the filter elements.

In one embodiment the support and filter elements may be integral wherein the filter elements are interconnected at the area of convergence using a coupling means such as pins, caps, rings, welds, ties or snap fitting arrangements. This induces strain in the cantilevered filter elements during use in a blood vessel that is distributed where the filter elements are connected to the filter frame. The invention addresses this problem using shape setting and/or annealing steps to improve durability, referred to as fatigue performance in this document, and teaches methods to provide a more streamlined profile of the apex to enhance blood flow characteristics. This embodiment is referred to as 'Shape Set Filter Elements' in this document.

In another embodiment the support and/or filter elements may not be integral wherein the filter apex is integral with at least some of the filter elements. The integral apex enhances blood flow characteristics at the apex by providing a more streamlined profile while providing increased manufacturing efficiency and reduced manufacturing costs through elimination of joints at the apex. The invention also includes shape setting and/or annealing steps to reduce strain where the filter elements are connected to the support frame. This embodiment is referred to as 'Integral Apex' in this document.

In a further embodiment the support frame, filter, and filter apex are integral wherein the device is formed from a single piece. The integral apex provides a more streamlined profile to enhance blood flow characteristics at the apex while the single piece design provides increased manufacturing efficiency, reduced manufacturing costs and improved durability, referred to in this document as fatigue performance, as no joints are required in the device. Shape setting and/or annealing steps are also taught to reduce strain where the filter elements are connected to the support frame. This embodiment is referred to as 'Integral Filter' in this document. In this specification the terms "proximal" and "distal" are with reference to the direction of blood flow, the proximal parts being upstream of the distal parts.

A vascular filter comprises:

one or more filter elements for capturing thrombus passing through a blood vessel, and one or more support members for supporting the one or more filter elements relative to a wall of the blood vessel.

By capturing the thrombus, the filter prevents the thrombus from passing to the heart or lungs, which may cause pulmonary embolism. By supporting the capture members this ensures that the filter elements are maintained in the desired location in the blood vessel.

The invention provides means to eliminate and/or reduce tilting, perforation and migration.

The present invention overcomes tilting through application of a longitudinal support structure.

In order to provide an effective filter, the longitudinal support is designed to include minimum implant length. The term "implant length" refers to the length of vessel required to implant a device. A device with less implant length is desirable as it will be suitable for patients with shorter vessels. Referring to FIG. 77, excessive filter length in a vena cava is unfavourable as it can lead to obstruction of the renal vein, which in time may lead to thrombosis. Also, some patients have shorter vena cavae than average which would prevent the use of a filter with excessive implant length. The longitudinal support structure of the present invention is designed to expand immediately as it is unsheathed when deployed from a femoral or jugular approach. For example, when deploying from a femoral approach, a portion of the longitudinal support is expanded and pressed against the vessel wall when the cranial half of the device is uncovered, this step actively pushes the cranial end of the delivery catheter (with the caudal end of the device sheathed) away from the vessel wall to remove delivery induced tilting. As the proximal end of the device is unsheathed, it is now located centrally in the vessel and the immediate expansion of the proximal support ring assumes its cylindrical configuration. Tilting is a well known complication of IVC filters and is associated with complications including IVC perforation, migration and reduced capture efficiency. Perforating filters can cause injury to nearby organs leading to severe discomfort, injury, and/or death of the patient. Tilted filters have a tendency to perforate as the apex of the conical filter or other free ended struts point into the vessel wall. When a filter is tilted, not only are its barbs out of contact with the vessel wall, its radial force is unevenly distributed against the vessel wall. The filter is operating without adequate vessel securing means and is at high risk for migration. Migration of a filter to the heart can cause massive pulmonary embolism. The uneven force distribution also leads to fatigue and fracture of the device as it is subjected to increased localised strains. Vena cava filters experience deflections at a rate of 70/min radially and 20/min longitudinally due to pulsatile blood flow and respiration respectively—these deflections exacerbate the risks of perforation, migration, and fracture of a tilted filter.

Reduced capture efficiency is a consequence of tilted filters as the apex of the filter cone drifts off centre. Peak flow velocities are in the centre of the vessel for uniform blood flow and it is through these peak velocities that blood clots flow. Therefore, vena cava filters are designed to have higher filter efficiency at the centre of the vessel. As the apex of a tilted filter moves to one side of the vessel, larger openings (designed to be positioned at the periphery of the device) move towards the centre of the vessel and reduce the capture efficiency of the device. Tilting of the filter is also expected to reduce the effectiveness of lysis which is the physiological process in which the captured clots are broken down in the body. This expectation is due to captured clots being directed to the vessel wall, away from peak flow velocities in the centre of the vessel. Holding the clot centrally in the vena cava is understood to provide optimal conditions for lysis. The ratio of filter length to vessel diameter should range from 1:1 to 2.3:1 when deployed in the filters maximum indicated vessel diameter to prevent tilting. More preferably, the ratio of filter length to vessel diameter should range from 1.5:1 to 2:1. The longitudinal support is designed to press against the vessel wall with sufficient radial force to prevent migration in the vessel. The support may also be fitted with barbs or protrusions to aid in anchoring it to the vessel wall.

The filter elements connect to the apex in a way that minimises obstruction to the blood flow, for instance, it is preferred that two or more filter elements merge into one filter element in close proximity to the apex in order to provide a streamlined connection (refer to FIGS. 2A, 2B, 7A, 7B, 27A-27F, 29A-29H, 30, 47A, 47B, 48A-48D, 61A-61D, 62A-62C, 67A-67C and 76A to 76C). The proximity of the merging point to the apex should range from 1 to 10 mm; a range of 3 to 6 mm is preferred.

In another aspect, a vascular filter comprises:
a support frame and an array of filter elements,
the filter elements extending from the support frame towards a central apex,
the filter element ends being located between the support frame and a central axis of the filter, wherein the filter element ends are interconnected. The invention affords improvements to the art by disclosing a filter that enhances fatigue resistance of a vena cava filter.

The invention also provides an interconnected filter apex with a more streamlined profile to improve blood flow characteristics. Refer to FIGS. 5, 12A to 19E, and 80 to 139. The streamlined profile reduces irregular flow patterns to prevent the formation of fibrin growth and blood clots. The formation of blood clots on permanent filters is well known in the art to occur after implantation. Additional antithrombogenicity can be achieved by including an antithrombogenic coating on at least part of the surface of the filter elements and apex. Such coatings include but are not limited to hydrophilic, hydrophobic, heparin or other thrombo-resistant pharmacological coatings.

Durability, referred to as fatigue resistance in this document, is enhanced by reducing the deflection and consequent loading/strain of the filter elements relative to the support frame. The deflection prior to loading can be reduced for a filter designed for a particular vessel size by shape setting the filter elements to form a central apex when constrained in the indicated vessel size without interconnection between the filter element ends. This is advantageous for support frame designs that include a hoop distal to the filter element ends as in most cases, the filter element ends will be free to move relative to each other and need to be pulled radially inwardly in order to form a central apex. The force required to form the central apex results in strain where the filter elements connect to the support frame. Reducing the deflection required to form a central apex reduces the force and resultant strain.

In another embodiment, the filter is indicated across a vessel size range, preferably from 16 to 32 mm internal diameter. For this embodiment, deflection is relative to the vessel that the filter is constrained in. Taking a filter that is indicated for blood vessels ranging from 16 to 32 mm internal diameter, it is preferred that the filter elements are shape set to form a central apex when constrained in a vessel midway (24 mm) across the vessel size range. Then, the deflection of the interconnected filter element ends is equal when constrained in the lower (16 mm) and upper (32 mm) vessel sizes, the filter elements bending radially outwardly in the lower vessel size and the filter elements bending radially inwardly in the upper vessel size. Another way of describing this embodiment is that the filter element ends will be positioned a quarter way between a central axis and the support frame when constrained by the upper vessel size of 32 mm. Similarly, filters for other vascular applications may be sized for vessels in the range of 3 mm to 12 mm.

A preferred embodiment is indicated across a vessel size range, preferably from 16 to 32 mm internal diameter, sized in this example to suit the vena cava, with filter elements that extend radially inwardly so that their ends are positioned at a point radially outwardly of a quarter way position between a central axis and the support frame when constrained in the upper vessel size of 32 mm. This embodiment balances tensile strain between the upper and lower vessel sizes and accounts for the influences of the filter element centroid.

These embodiments are advantageous for support frame designs with and without distal support hoops as all marketed filter devices are indicated across a vessel size range and hence devices including support frames with filter elements interconnected at a central apex tend to have maximum strains in the upper vessel size and minimum strains in the lower vessel size due to the filter elements bending radially inwardly relative to the support frame. This is because their form must favor the upper vessel size unconstrained in order to apply sufficient radial force against the vessel wall. It is appreciated that this may be reversed in that the filter element ends may be heat set with their ends forming a central apex and the filter elements are deflected radially outwardly relative to the support frame in the lower vessel size including support frame designs with and without distal support hoops. The embodiments disclosed are advantageous for these designs in that they tend to have max strains in the upper vessel size and minimum strains in the lower vessel size as their form must favor the upper vessel size unconstrained.

The interconnection between the filter element ends may be supplied by way of a holder or by interlocking features attached to or part of the filter element ends.

In another aspect, a vascular filter comprises: one or more filter elements for capturing thrombus passing through a blood vessel, and one or more support members for supporting the one or more filter elements relative to a wall of the blood vessel, wherein at least one of the filter elements is integral with the filter apex.

The invention reduces fibrin formation and clot build up through improved blood flow characteristics by providing an integral filter apex that eliminates filter element joints at the filter apex. Such a construction minimizes obstruction to blood flow by providing a streamlined profile and reduces irregular flow patterns to prevent the formation of fibrin growth and blood clots. Refer to FIGS. 27A-27F and 62A-62C. The formation of blood clots on permanent filters is well known in the art to occur after implantation. Additional antitrombogenicity can be achieved by including an antithrombogenic coating on at least part of the surface of the filter elements and apex. Such coatings include but are not limited to hydrophilic, hydrophobic, heparin or other thrombo-resistant pharmacological coatings.

In another aspect, a vascular filter comprises:
one or more filter elements for capturing thrombus passing through a blood vessel, and one or more support members for supporting the one or more filter elements relative to a wall of the blood vessel, wherein the device is manufactured from a single piece.

The present invention discloses a blood filter that is manufactured in one piece to provide an integral filter. Advantages of an integral filter include increased manufacturing efficiency, reduced manufacturing costs and improved durability, referred to in this document as fatigue performance, as no joints are required in the device. The locations of joints frequently coincide with failure locations when devices are subject to cyclical loading.

According to another aspect, the invention provides a vascular filter device comprising a support frame and filter elements, the filter elements extending from the support frame towards filter element ends forming an apex at which they are interconnected, wherein said apex is located at or near a central axis of the vascular filter device; and wherein the filter elements are biased such that if unconnected the filter element ends are located between the support frame and said central axis when the vascular filter device is unconstrained. The filter elements thus have a natural position which leads to little stress in use while they are interconnected at the apex. This is particularly advantageous in light of the conditions with high frequency expansion and contraction as set out above in the introduction. In one embodiment, the support frame and the filter elements are formed integrally. In one embodiment, the support frame and the filter elements are formed from NiTi.

In one embodiment, the filter element unconnected positions are provided by the filter element shapes and the angles at which they extend from the support frame.

In one embodiment, the filter elements have positions if unconnected such that the filter element ends are located approximately 10% to 50% of the distance from the central axis to the support frame. In one embodiment, the position is approximately 15% to 40% of said distance. In one embodiment, the vascular filter device has an indicated vessel size range, and wherein the filter elements are biased to have positions if unconnected such that:

(a) when the device is constrained in a vessel which lies in an upper sub-range of said indicated range, the filter element ends are between the central axis and the support, (b) when the device is constrained in a vessel which lies in a central sub-range of said indicated range the filter element ends are approximately on the central axis, and (c) when the device is constrained in a vessel which lies in a lower sub-range of said indicated range the filter element ends extend through said central axis.

In one embodiment, the filter elements have similar maximum strains in situations (a) and (c) when the filter element ends are interconnected. In one embodiment, the filter elements have approximately equal maximum tensile strains in situations (a) and (c) when the filter element ends are interconnected.

In one embodiment, the support frame comprises a proximal hoop, a distal hoop, and interconnecting struts. In one embodiment, the proximal hoop has peaks and the filter elements are connected to the support at or adjacent distal peaks of the proximal hoop.

In one embodiment, the filter element ends, the filter elements, and the support frame are formed integrally from one piece.

In one embodiment, the filter element ends are formed integrally to provide an integral apex.

In one embodiment, the filter element ends are interconnected, by a holder.

In one embodiment, at least some filter elements have eyelets and the holder is trained through the eyelets.

In one embodiment, the holder has an integral fastener.

In one embodiment, the holder is in the form of a spiral in which spiral turns are in contact or in close proximity with each other to provide the integral fastener.

In one embodiment, the holder is in the form of a planar spiral in which the spiral turns overlap in the radial direction.

In one embodiment, the holder is in the form of a three-dimensional spiral in which the spiral turns overlap at least partly in the axial direction. In one embodiment, the outer diameter of the holder is tapered axially.

In one embodiment, the spiral has between 1 and 2 turns.

In one embodiment, the spiral is formed from a length of material having tapered ends.

In one embodiment, the holder comprises a clip formed from a body having one end which fits into the other end.

In one embodiment, the holder comprises a length of material forming a loop at one end and free ends of the length form a hook extending through the loop.

In one embodiment, the free ends are tied in a knot or are welded to prevent release of the holder. In one embodiment, the free ends are engaged through at least one filter element end eyelet at least twice.

In one embodiment, the holder comprises a plurality of prongs which are directed radially inwardly and are arranged to engage with filter element eyelets.

In one embodiment, the prongs and filter element ends are arranged to be crimped together for fastening the filter element ends. In one embodiment, the prongs are directed distally at their ends.

In one embodiment, the prongs have features for snap-fitting into the filter element eyelets.

In one embodiment, the holder comprises at least one hook engaging filter element eyelets.

In one embodiment, said hooks are mounted on a ring or disk-shaped holder base.

In one embodiment, there is a pair of hooks on opposed sides of the central axis, each arranged to engage a plurality of filter element eyelets.

In one embodiment, said hooks extend in a radial plane only.

In one embodiment, the holder is S-shaped. In one embodiment, the holder is in the form of a split ring.

In one embodiment, the split ring has ends forming a non-reentrant opening.

In one embodiment, the holder includes at least one abutment to prevent the filter elements from dislodging.

In one embodiment, the holder includes a sacrificial length arranged to aid entrainment through the filter element eyelets and wherein the sacrificial length is removed after assembly. In one embodiment, the holder comprises a central hub with slots to accommodate filter elements and a clamping ring to retain the filter elements in said slots.

In one embodiment, the filter elements are interconnected by interlocking features, such as slots and ridges or dovetail features. In one embodiment, the filter elements are magnetically interconnected.

In one embodiment, the interlocking features are integral with the filter elements.

In one embodiment, the holder has one or more annular sockets to receive the ends of the filter elements.

In one embodiment, the holder is crimped.

In one embodiment, the device comprises two parts which are connected together at a connection.

In one embodiment, the connection is in the struts.

In one embodiment, the connection is at the proximal end, at the distal end, or between said ends.

In one embodiment, the connection is between the filter and the support. In one embodiment, the connection is within the filter.

In one embodiment, the parts are connected by a connector including a sleeve which receives two members. In one embodiment, the connection comprises device members butt-joined together. In one embodiment, the connection comprises overlapping device members. In one embodiment, the connection comprises male and female connectors.

In one embodiment, the connection comprises a joint allowing mutual pivoting.

In one embodiment, the sleeve comprises formations to engage with members inserted into the sleeve. In one embodiment, the formations are arranged for snap-fitting of the members within the sleeve.

In one embodiment, the filter elements extend towards two or more filter apexes.

In one embodiment, the filter apexes are joined.

In one embodiment, the device is formed from laser-cut tubing and the diameter of the joined filter apexes is less than that of the tubing.

In one embodiment, the filter apex interconnection is arranged to provide flexibility in the axial direction and/or the radial direction.

In one embodiment, the filter apex interconnection is C-shaped in axial view.

In one embodiment, the filter apex interconnection is formed to receive an array of connector struts when the device is compressed before delivery.

In one embodiment, the device is formed from laser-cut tubing and the tubing diameter is greater than the diameter of the filter apex interconnection.

In one embodiment, the filter apex interconnection is formed from a necked-down region of the tubing. In one embodiment, the two parts are cut from a single tube.

In another aspect, the invention provides a vascular filter device manufactured from a single piece of raw material. In one embodiment, the filter or the support is inverted from a natural position during manufacture so that the filter lies within a space encompassed by the support frame.

In one embodiment, at least some filter elements are connected to the distal hoop. In one embodiment, the proximal and distal hoops comprise at least one sinusoid, crown, or zigzag pattern. In one embodiment, the distal hoop comprises an array of V-shaped struts and wherein the V-shaped struts are not directly interconnected.

In one embodiment, the distal hoop comprises an array of V-shaped struts and extension struts connecting the array of said V-shaped struts to the connector struts.

In one embodiment, the distal hoop comprises an array of M-shaped struts.

In one embodiment, the distal hoop comprises an array of closed cells.

In one embodiment, an array of twin connector struts interconnect said hoops.

In one embodiment, each twin connector strut is not connected at the distal and proximal ends forming an opening in the array of cells between the struts of the twin connector strut and separating the proximal support hoop into an array of v-shaped or m-shaped struts.

In one embodiment, the proximal hoop comprises an array of cells and wherein an array of twin connector struts interconnect said hoops, wherein each twin connector strut is not connected at the distal and proximal ends forming an opening in the array of cells between the struts of the twin connector strut and separating the distal support hoop into an array of V-shaped or M-shaped struts, and wherein the filter elements extend between the struts of the twin connector strut.

In one embodiment, the filter elements are connected to the support frame via an array of distally pointing V-shaped struts.

In one embodiment, the proximal hoop comprises two crowns, and wherein the filter elements are connected to the distal peaks of the proximal hoop. In one embodiment, the V-shaped struts of the distal hoop point distally, and wherein each V-shaped strut is connected to the proximal hoop via two connector struts.

In one embodiment, an array of V-shaped filter elements extend to an integral apex between adjacent V-shaped struts of the distal hoop.

In one embodiment, the V-shaped struts of the distal hoop point proximally and wherein each V-shaped strut is connected to the proximal hoop via one connector strut. In one embodiment, the filter elements are connected to the connector struts at points distally of the extension strut connection.

In one embodiment, the filter elements are connected to the connector struts at positions proximally of the extension strut connection.

In one embodiment, there are two extension struts for every connector strut.

In one embodiment, there is one connector strut for every M-shaped strut and wherein the ends of adjacent M-shaped struts are joined.

In one embodiment, the closed cell is diamond shaped and the array of connector struts are connected to the proximal peaks of the diamonds. In one embodiment, the cells are diamond shaped and an array of twin connector struts are connected to the distal peaks of said cells.

In one embodiment, some of said filter elements are supported only by other filter elements. In one embodiment, additional filter elements extend from the apex interconnection and are not connected at their proximal ends.

In one embodiment, at least some of the support struts have free distal ends. In one embodiment, the support frame comprises longitudinal struts which are not straight in configuration.

In one embodiment, the filter elements are formed to have a length-reducing shape or at least part of the support can be lengthened so that the apex interconnection lies between the most proximal and distal ends of the support when in the expanded state.

In one embodiment, the ratio of filter length to support frame diameter ranges from 1:1 to 2.3:1 when the device is unconstrained. In one embodiment, the ratio of filter length to support diameter ranges from 1.5:1 to 2:1 when the device is unconstrained. In one embodiment, a portion of the support is flared outwardly.

In another aspect, the invention provides a method of manufacturing a vascular filter device comprising a support frame and filter elements, the filter elements extending from the support frame towards filter element ends forming an apex at which they are interconnected, wherein said apex is located at or near a central axis of the vascular filter device; wherein the filter elements are biased such that if unconnected the filter element ends are located between the support frame and said central axis when the vascular filter device is unconstrained, wherein the method comprises the steps of:
providing a tubing, cutting the tubing, and expanding the tubing.

In one embodiment, the filter elements are heat-treated to provide said positions. In one embodiment, the support frame comprises a proximal hoop and a distal hoop and said hoops are interconnected by longitudinal support struts, and said hoops and struts are formed by cutting of said tubing.

In one embodiment, the cut tubing is expanded to form the filter and heat set to remember a permanent shape.

In one embodiment, the tubing is expanded after cutting to provide a new shape and is constrained in a fixture or on a mandrel for heat treatment. In one embodiment, the device is crimped down to a diameter that is greater than, equal to, or less than that of the tubing and loaded into a delivery sheath for low profile delivery to the implant site.

In one embodiment, the tubing is of a shape-memory material so that when deployed into an environment that is above an Af temperature, the device will revert to its expanded form provided by the shape setting step.

In one embodiment, the material is annealed to remove stresses raised through work hardening.

In one embodiment, the tubing diameter is greater than the radial dimension of the apex interconnection. In one embodiment, the filter apex interconnection is formed from a necked-down region of the tubing. In one embodiment, the tubing is cut to provide two parts which are subsequently interconnected at a connection.

In one embodiment, the filter or the support is inverted from a natural position during manufacture so that the filter lies within a space encompassed by the support.

DETAILED DESCRIPTION OF THE INVENTION

The invention will be more clearly understood from the following description of some embodiments thereof, given by way of example only with reference to the accompanying drawings in which:

FIGS. 1A-1D include side views and an end views of a filter device of the prior art as discussed above, the top images (FIGS. 1A and 1B) illustrating the device with the filter element ends unconnected, the bottom images (FIGS. 1C and 1D) illustrating the filter element ends interconnected;

FIGS. 2A and 2B are a set of oblique views of a device of the invention, the left image (FIG. 2A) illustrating the device with the filter element ends unconnected, the right image (FIG. 2B) illustrating the filter element ends interconnected; FIGS. 3A-3C include a plan, elevation, and end view of a device of the invention unconstrained with filter element ends unconnected and converging towards an apex at early stages of manufacture;

FIGS. 4A-4C include a plan, elevation, and end view of a device of the invention unconstrained with the filter element ends interconnected to form an apex at early stages of manufacture;

FIG. 5 is an oblique view of the filter element ends interconnected to form an apex with a holder; FIGS. 6A-6D are a set of side and end views of a device of the invention at early stages of manufacture constrained in a 032 mm and 024 mm tube, and FIG. 6(E) is a diagram illustrating the preferred filter element end positions at an early stage of manufacture before assembly with a holder when constrained in vessels with different vessel diameters;

Figure 9A:
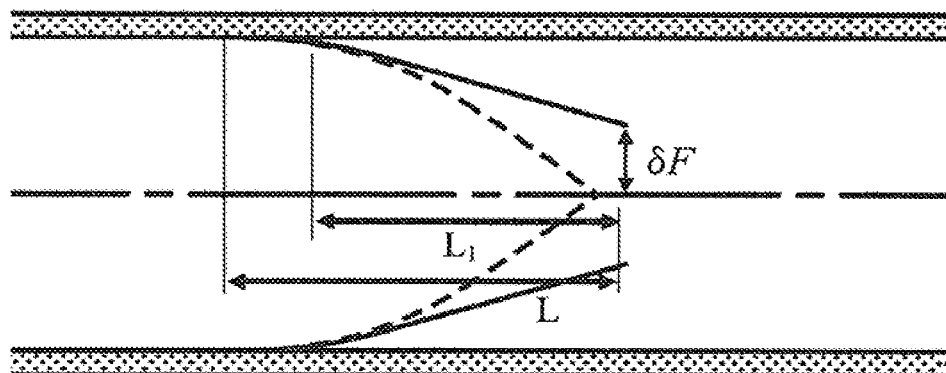
Figure 9B:
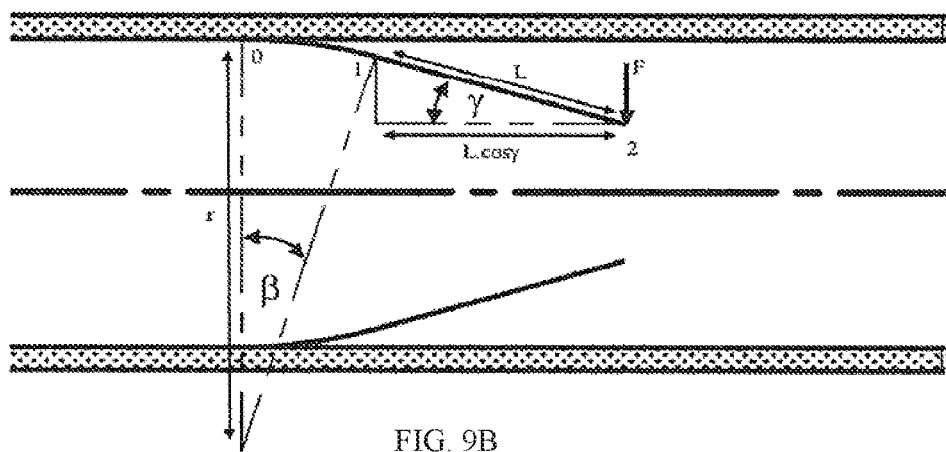
Figure 10A:
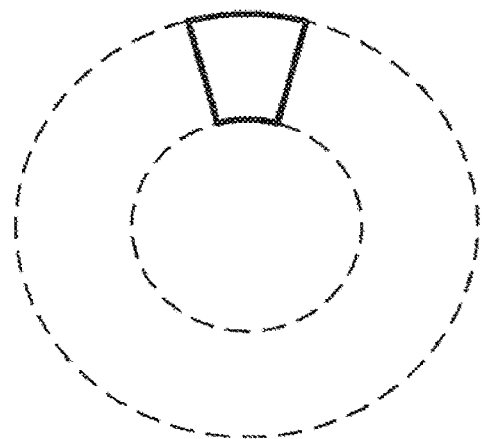
Figure 10B:
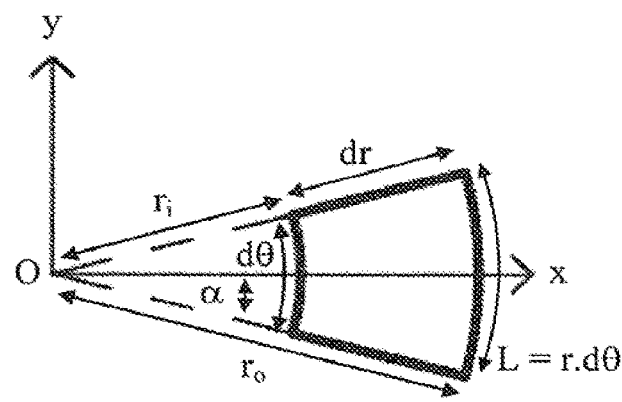
Figure 11:
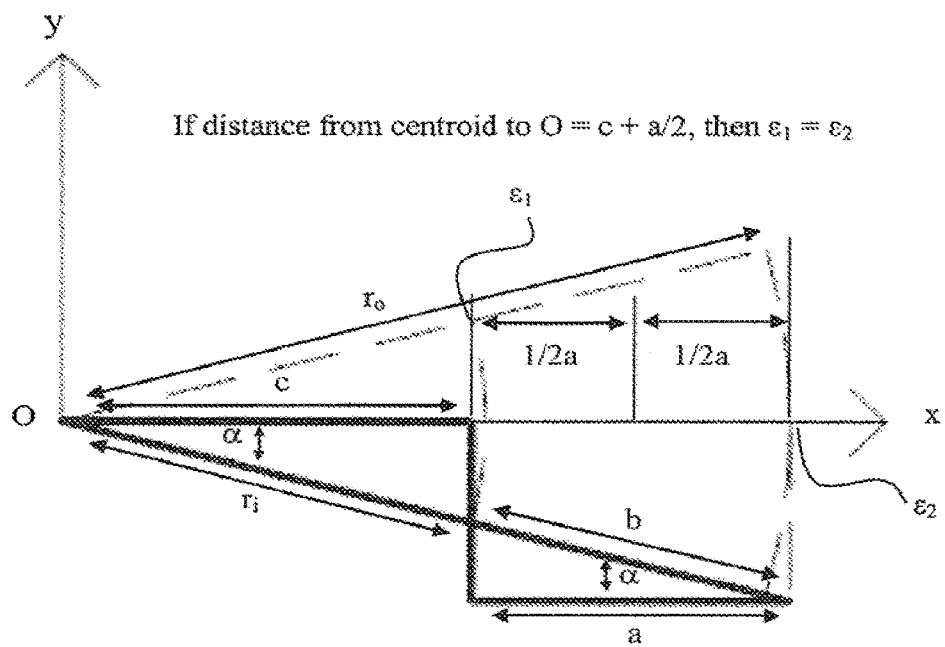
Figures 12A, 12B:
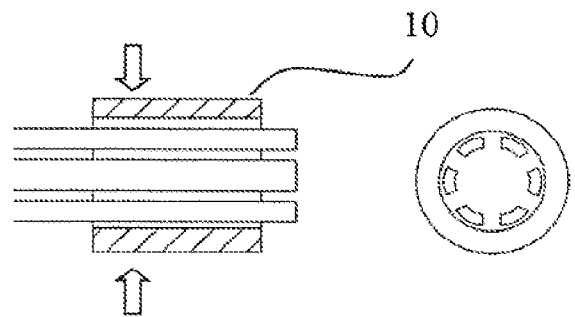
Figures 13A, 13B:
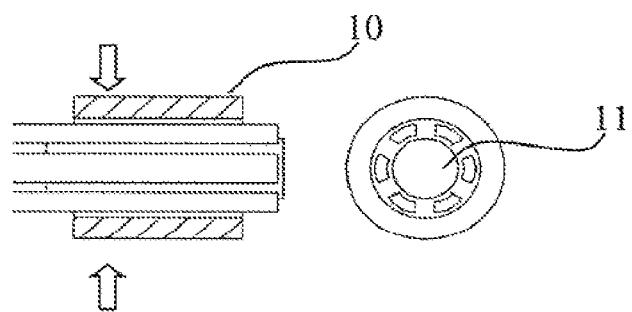
Figures 14A, 14B:
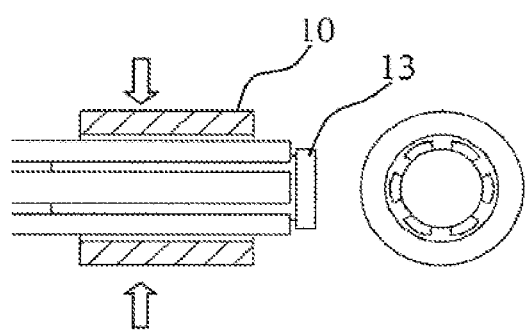
Figure 15:
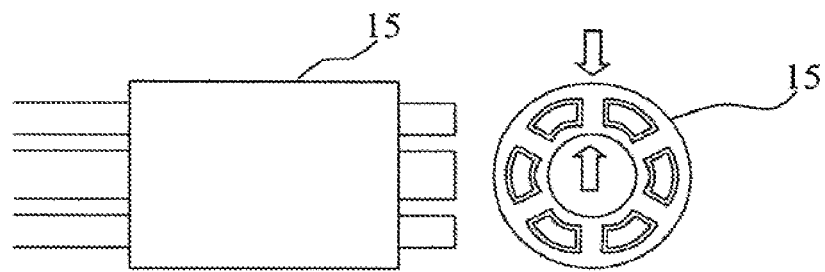
Figure 16A:
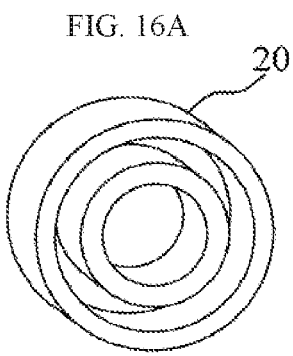
Figure 16B:
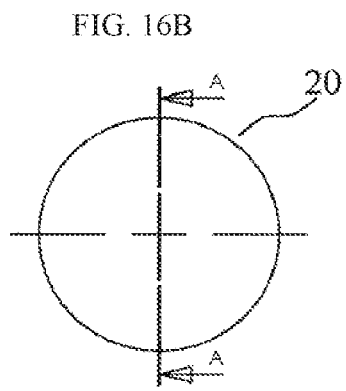
Figure 16C:
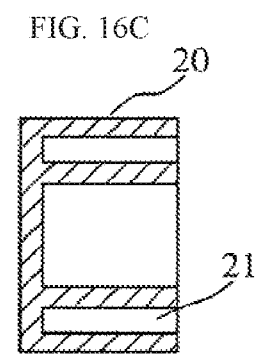
Figure 16D:
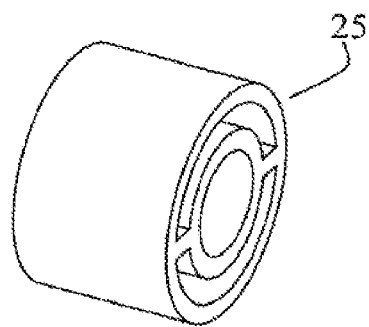
Figure 16E:
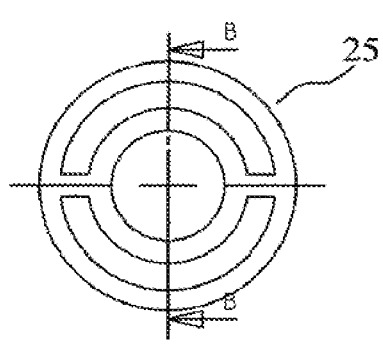
Figure 16F:
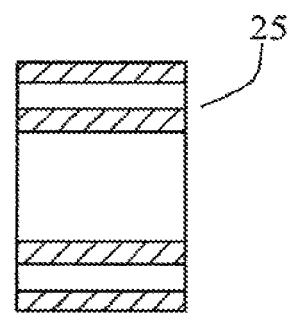
Figure 17:
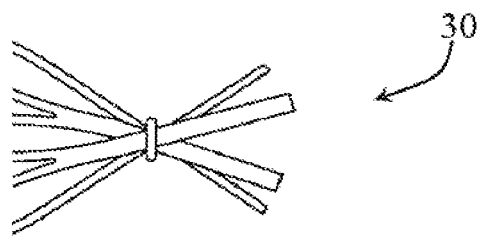
Figure 18A:
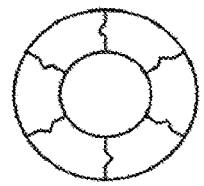
Figure 18B:
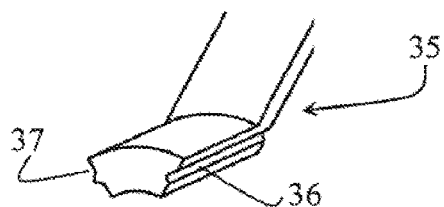
Figure 18C:
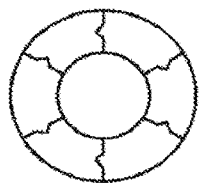
Figures 18D, 18E:
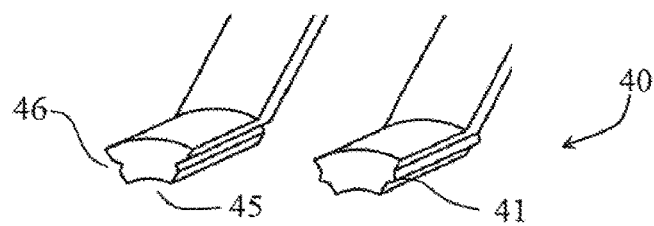
Figure 19A:
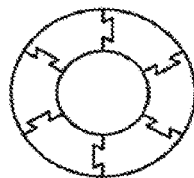
Figure 19B:
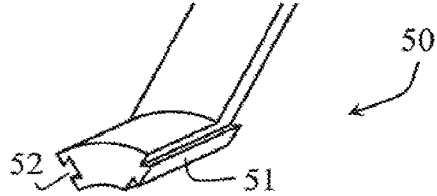
Figure 19C:
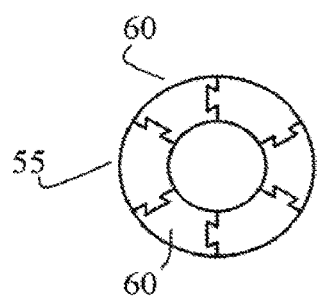
Figures 19D, 19E:
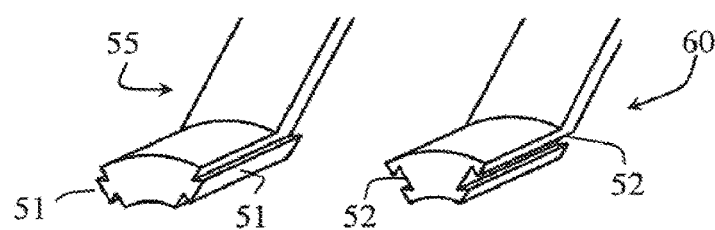
Figure 20:
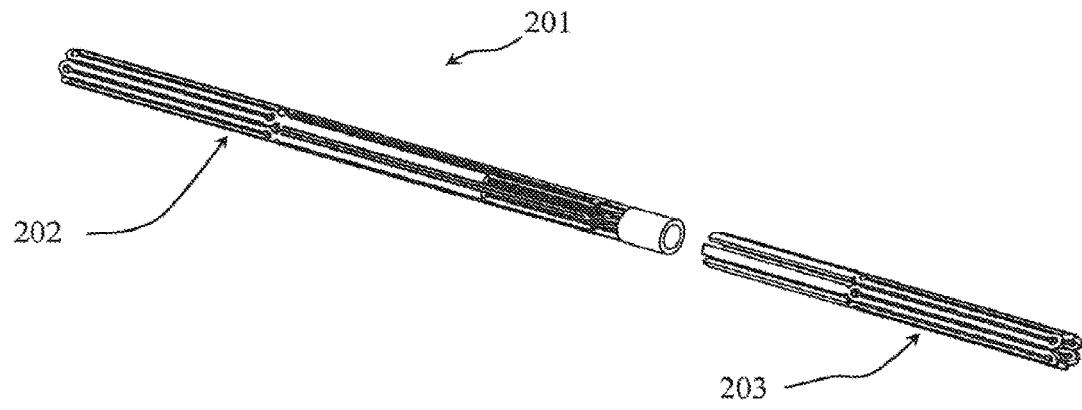
Figure 21A:
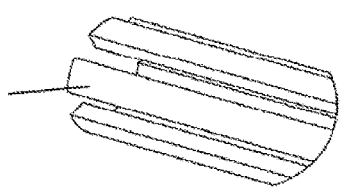
Figure 21B:
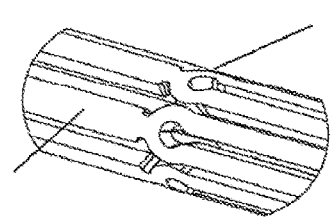
Figure 21C:
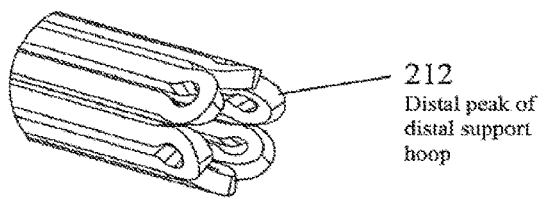
Figure 22A:
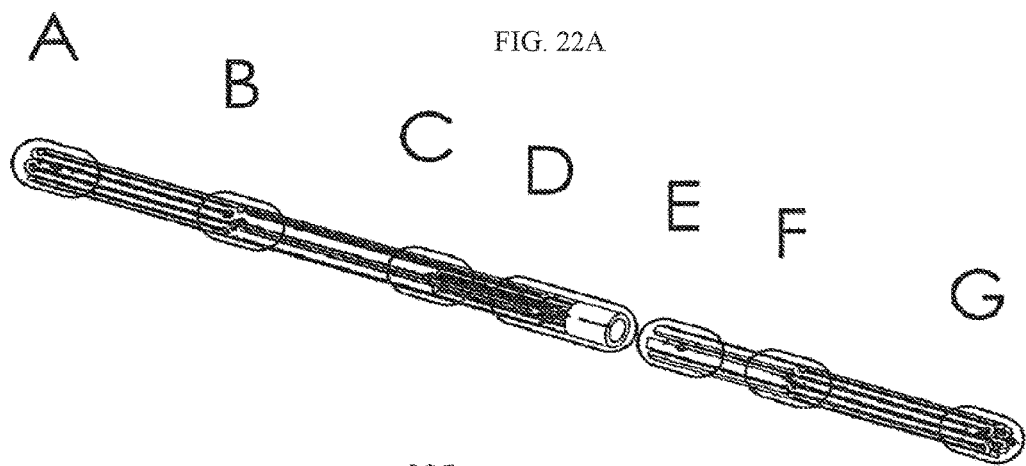
Figure 22B:
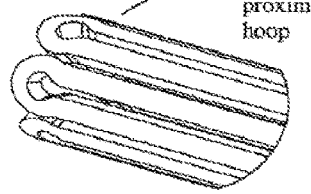
Figure 22C:
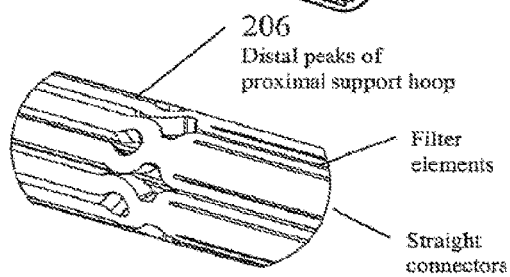
Figure 22D:
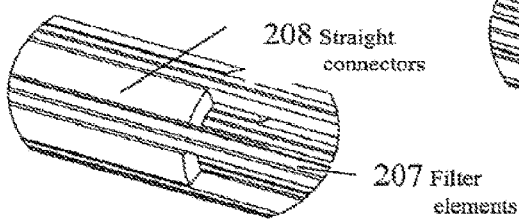
Figure 22E:
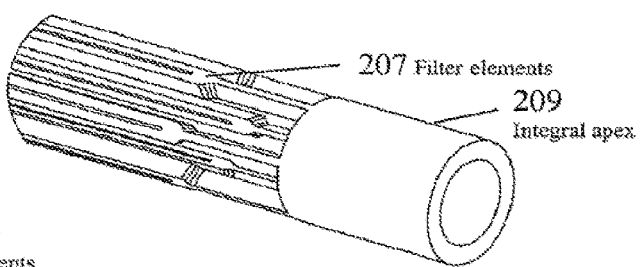
Figure 35A:
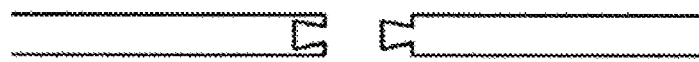
Figure 35B:
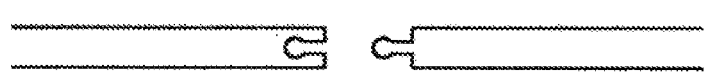
Figure 42:
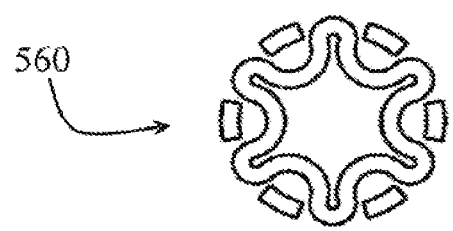
Figure 46A:
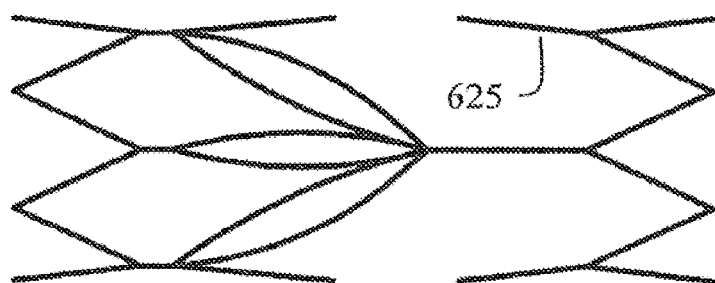
Figure 46B:
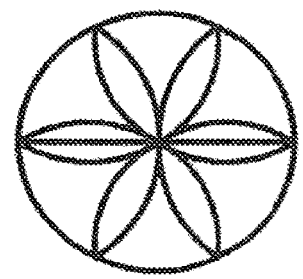
Figure 46C:
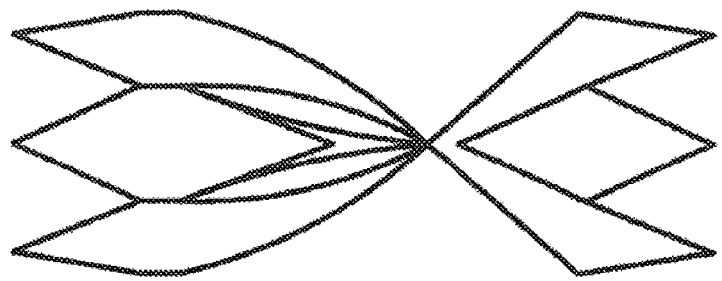
Figure 46D:
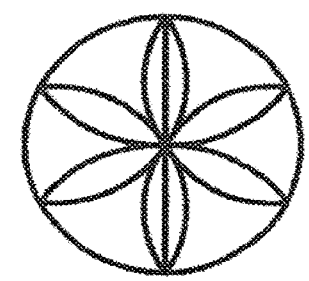
Figure 47A:
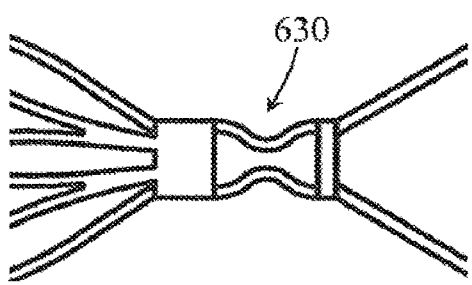
Figure 47B:
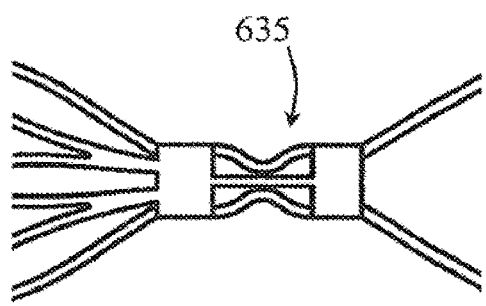
Figure 62A:
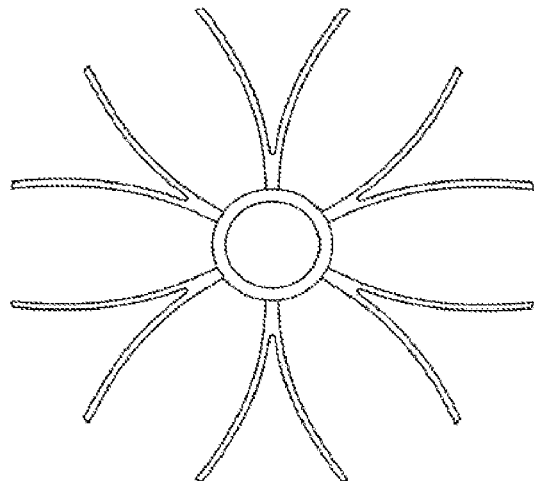
Figure 62B:
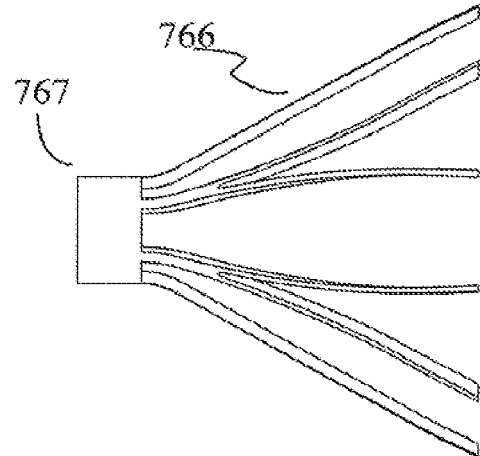
Figure 62C:
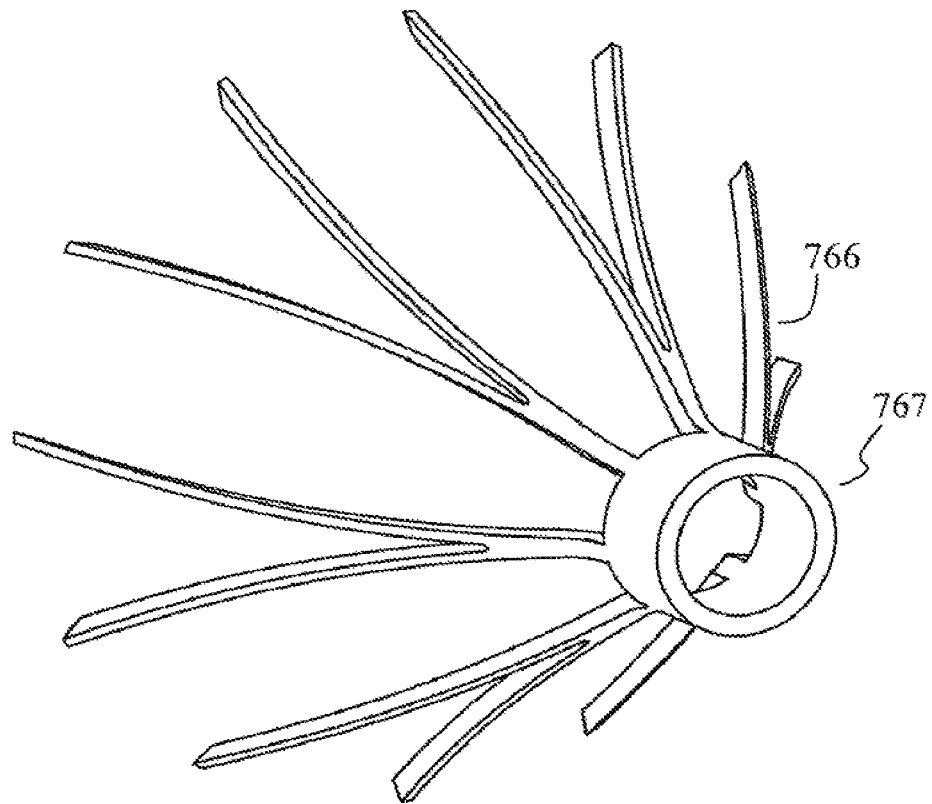
Figures 71A, 71B:
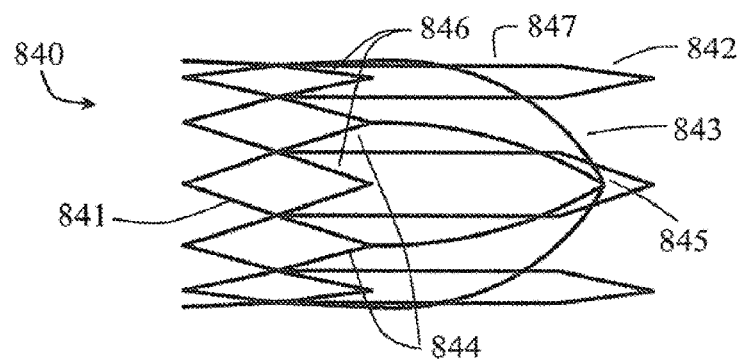
Figures 72A, 72B:
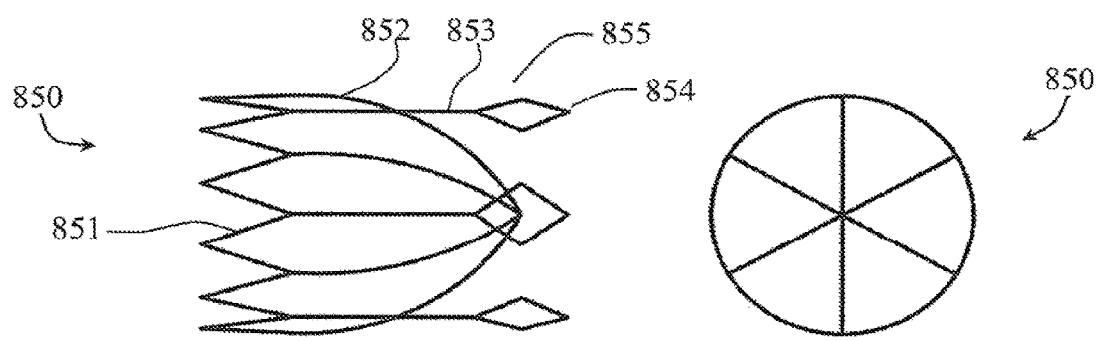
Figures 73A, 73B, 73C:
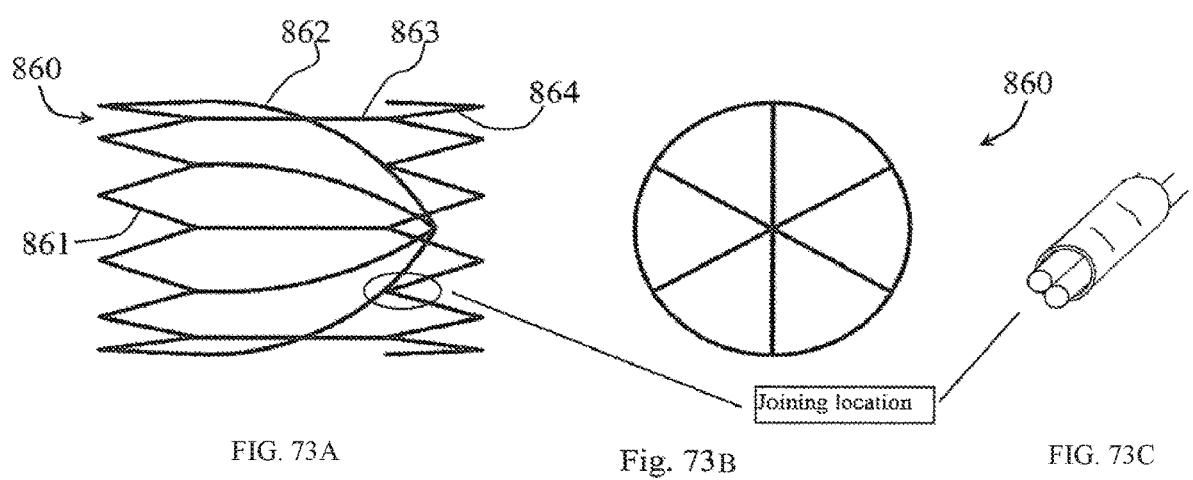
Figure 76A:
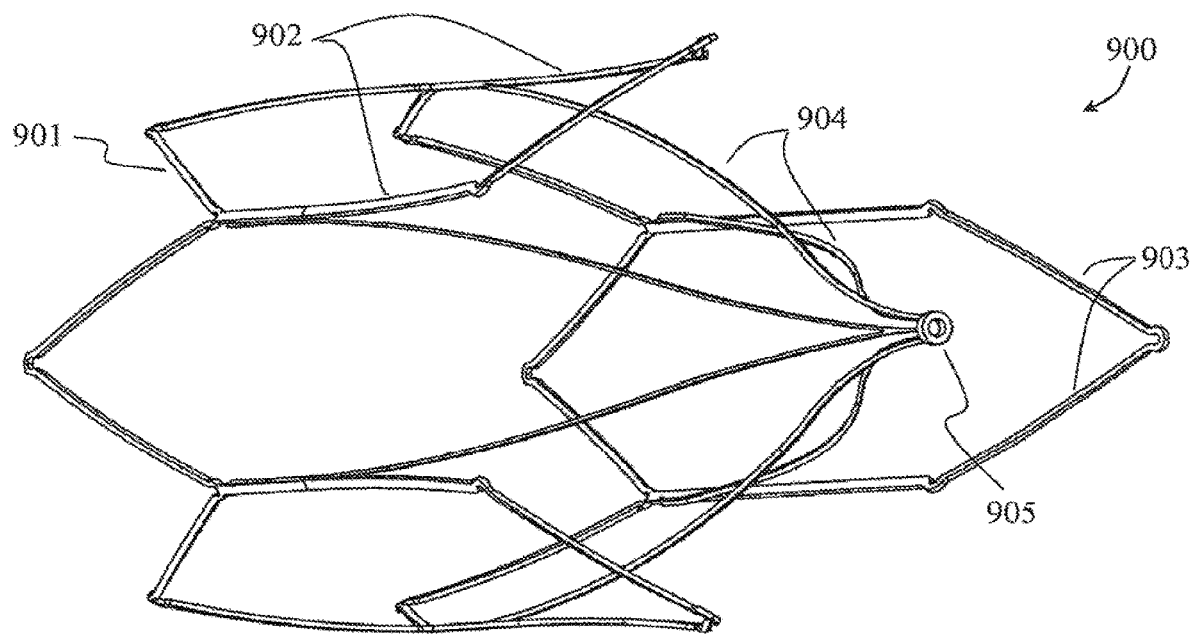
Figure 76B:
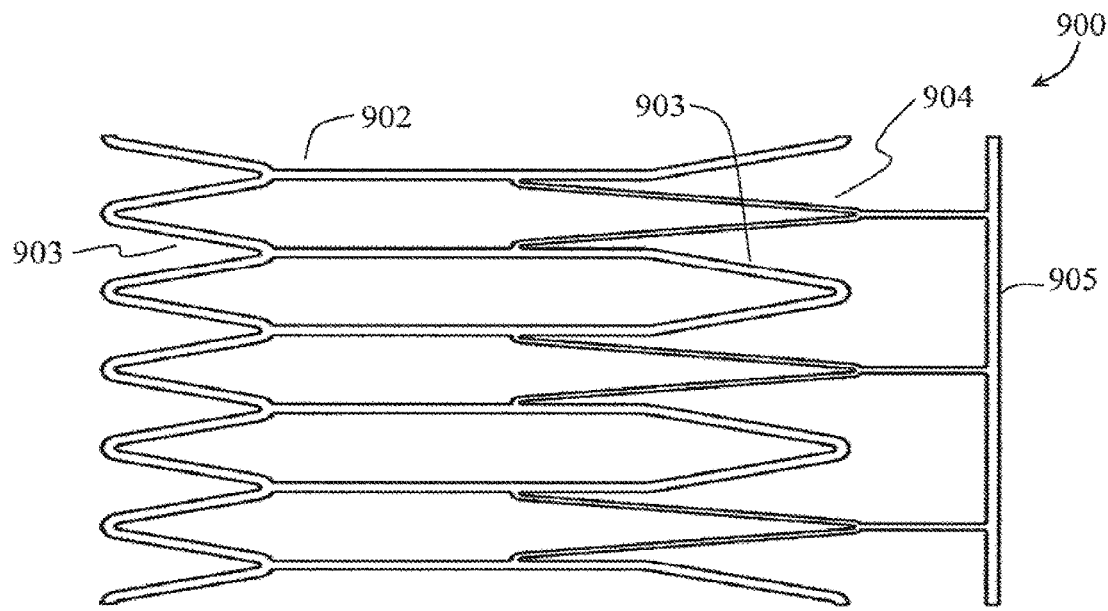
Figure 76C:
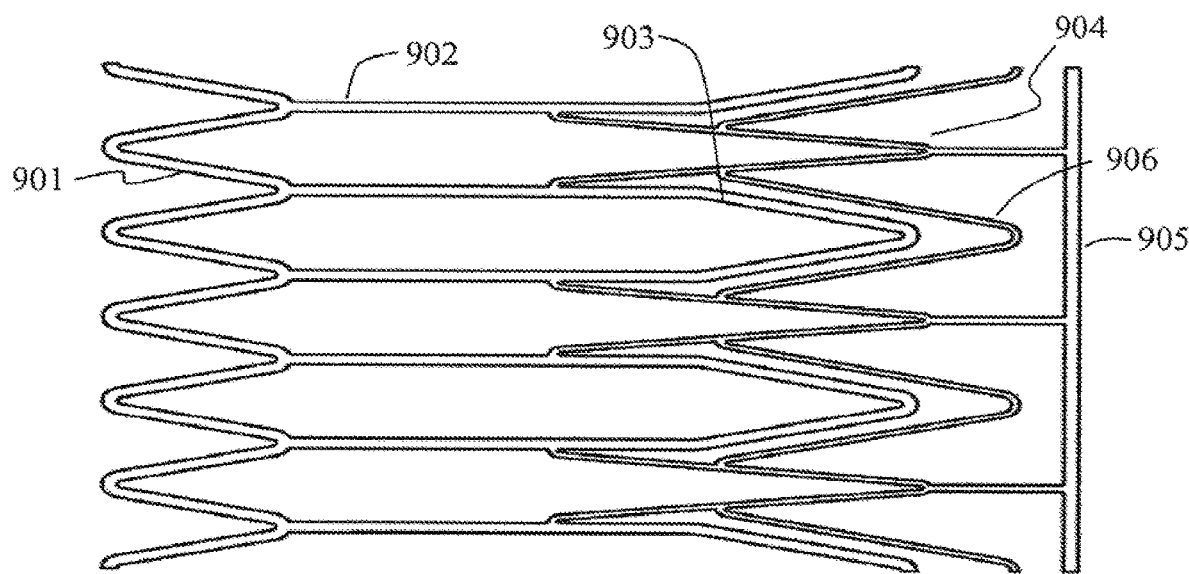
Figure 77:
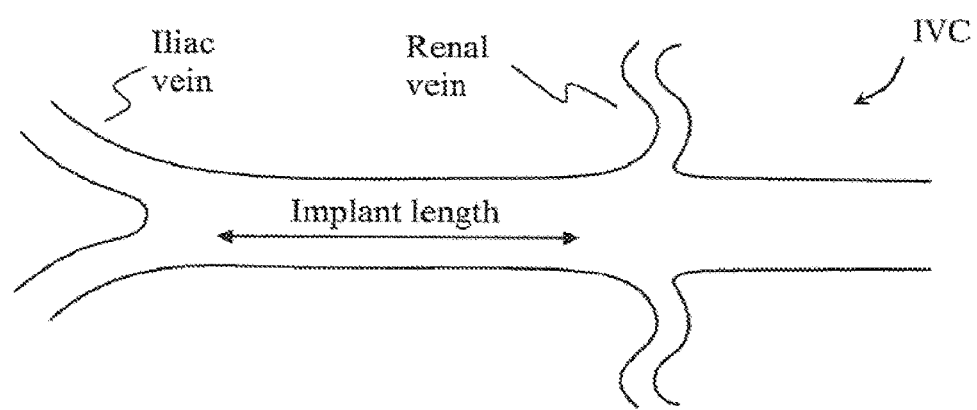
Figure 78A:
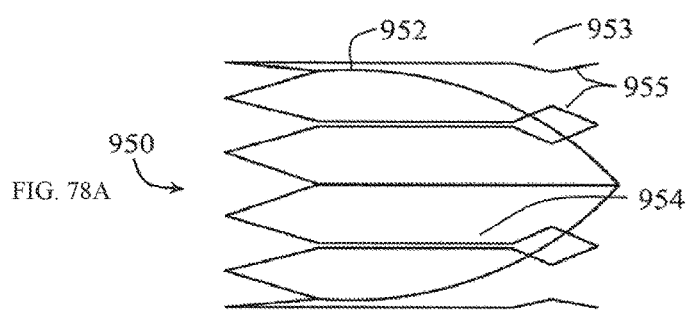
Figure 78B:
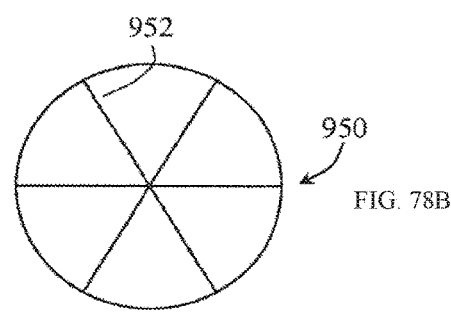
Figure 78C:
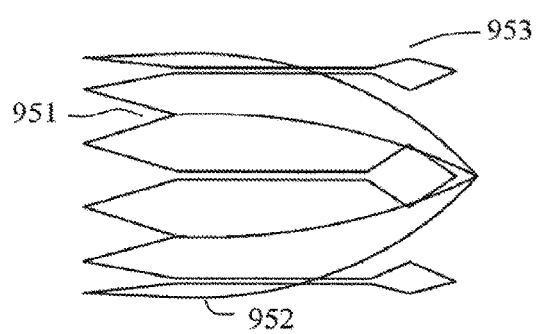
Figure 78D:
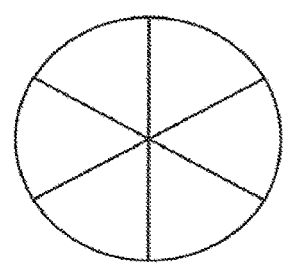
Figure 79A:
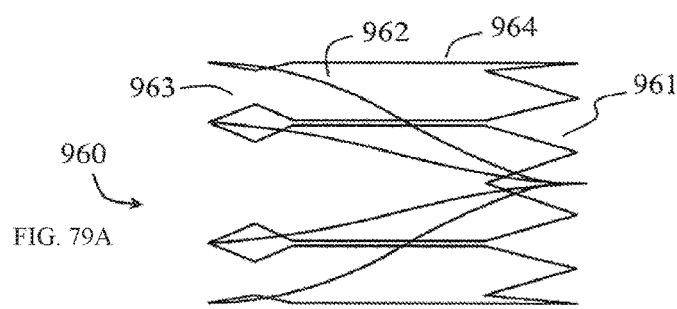
Figure 79B:
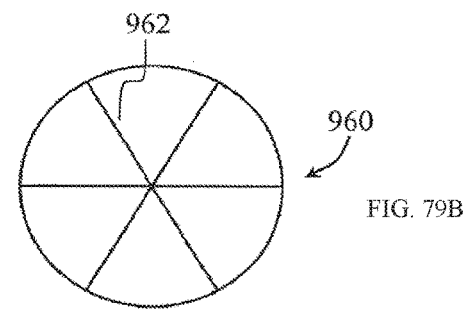
Figure 79C:
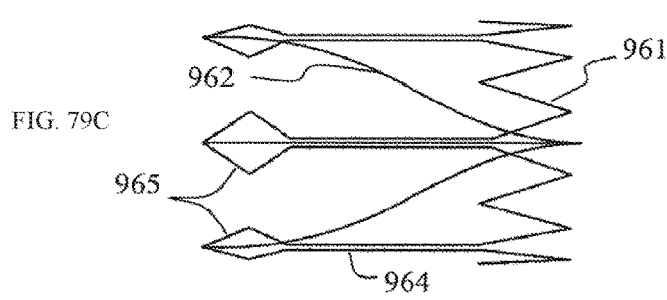
Figure 79D:
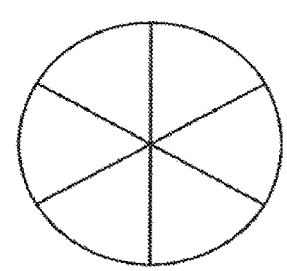
Figure 80:
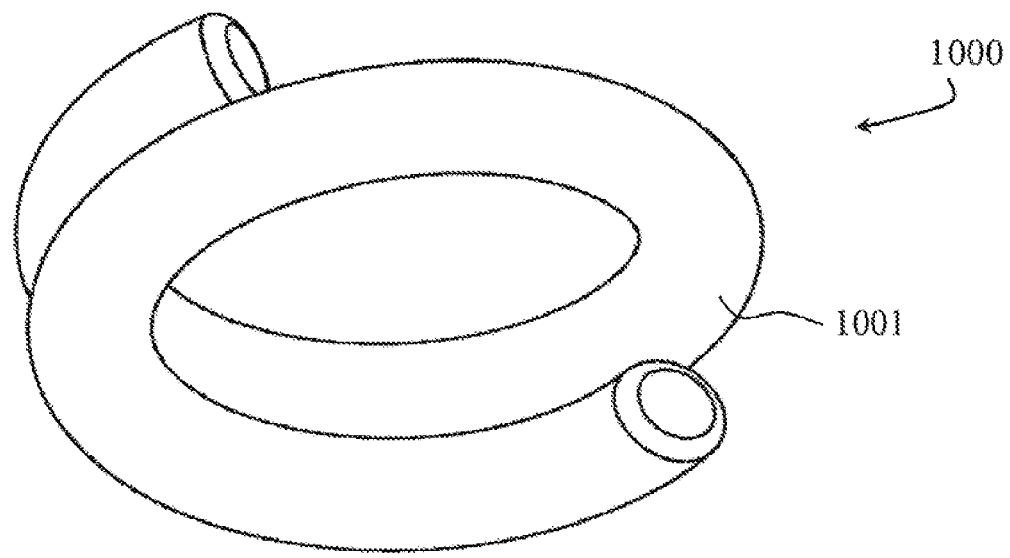
Figure 81A:
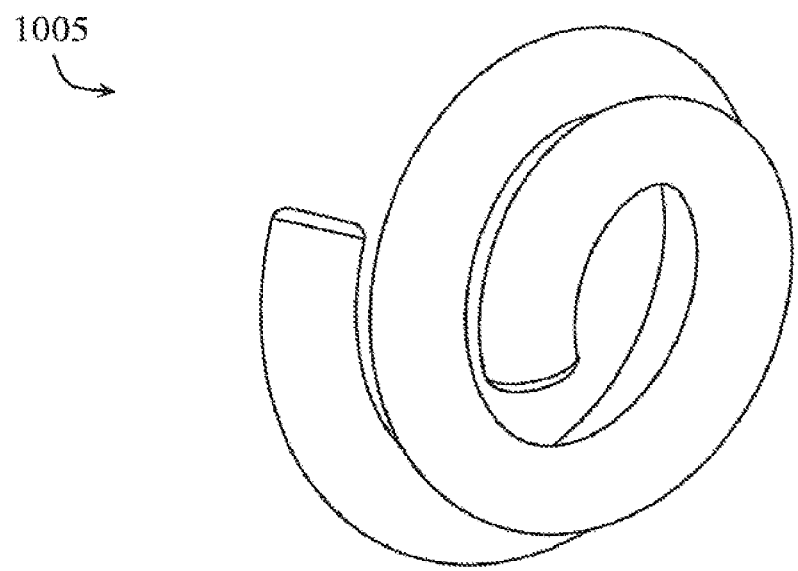
Figure 82:
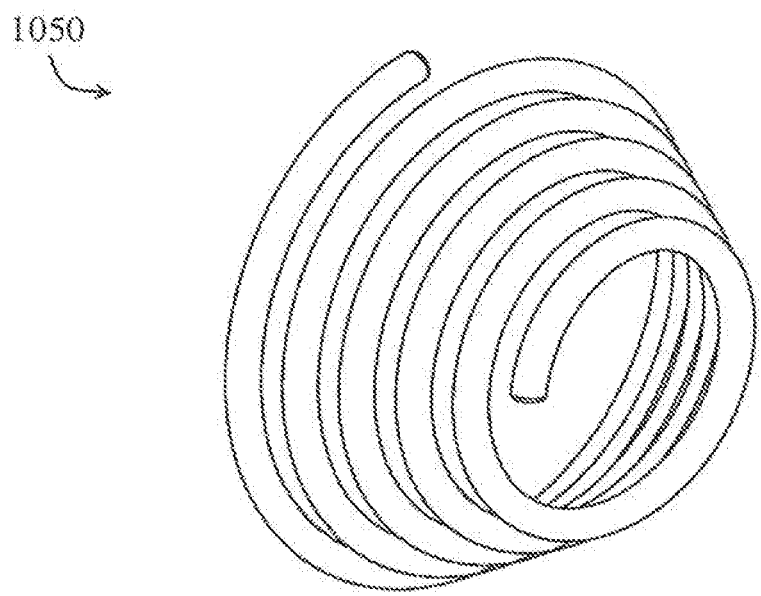
Figure 83:
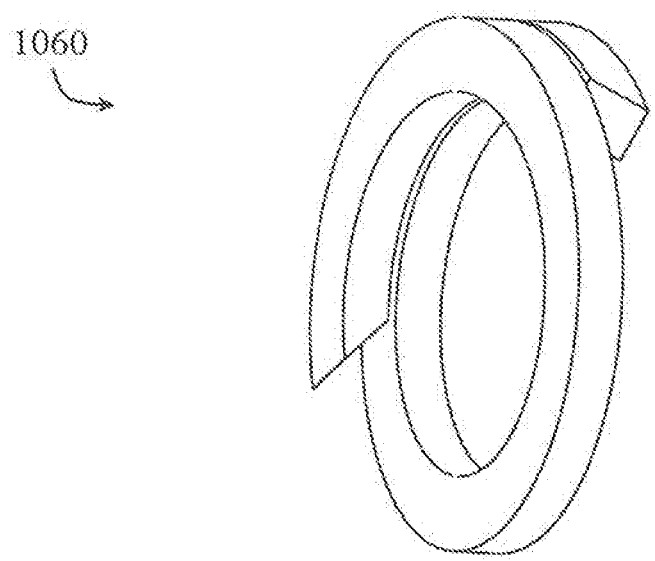
Figure 84:
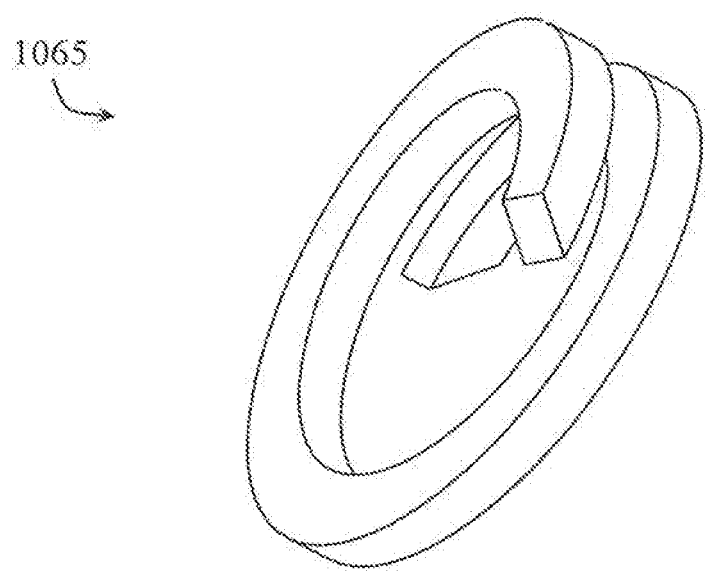
Figure 85:
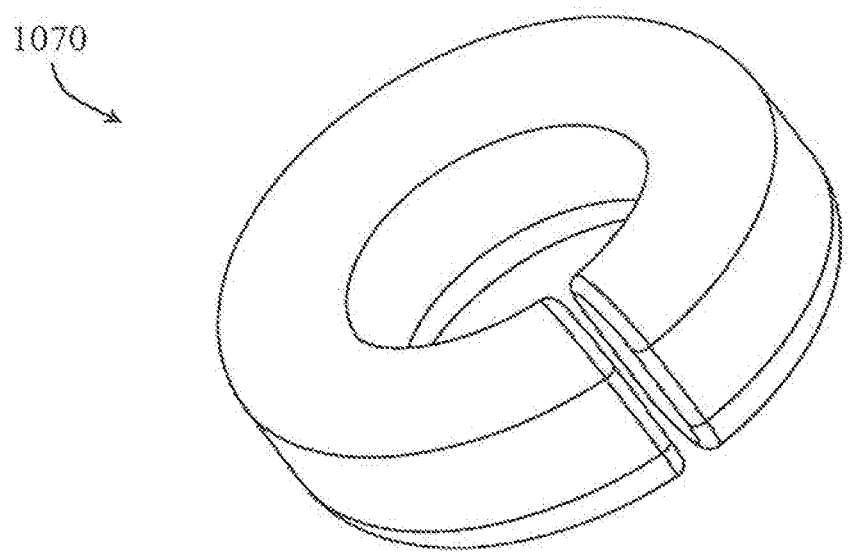
Figure 86:
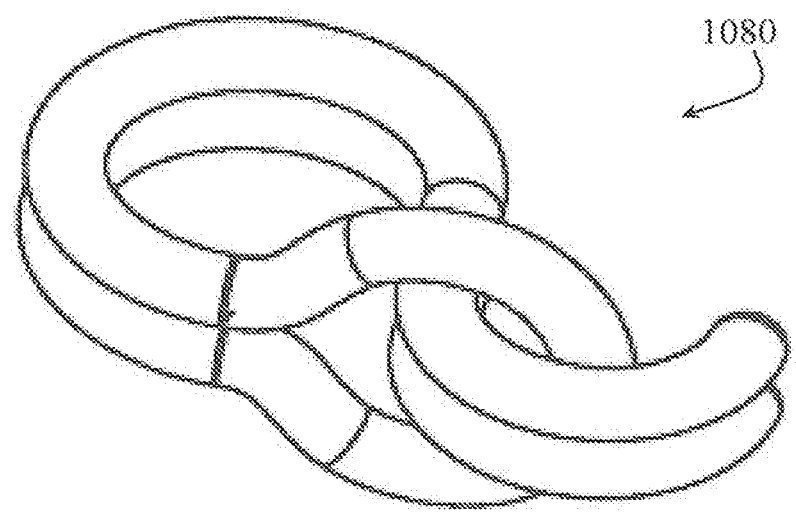
Figure 87:
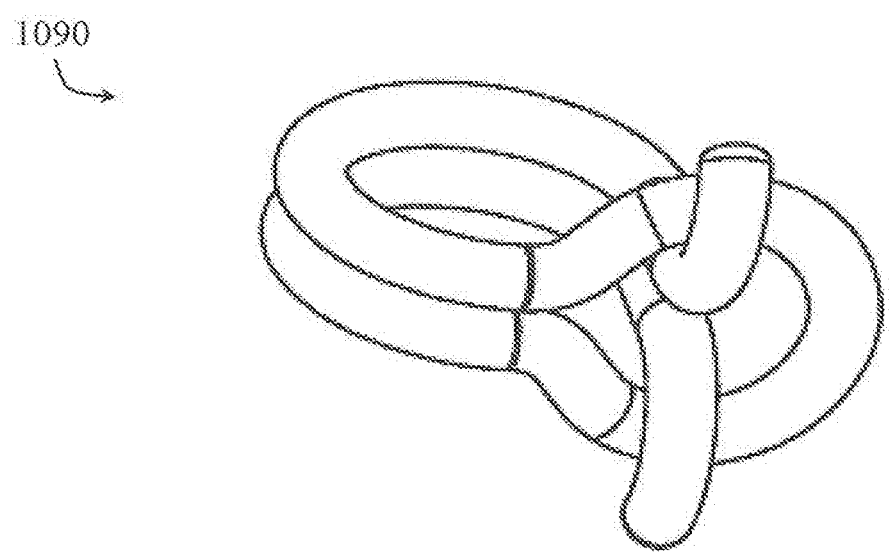
Figure 88:
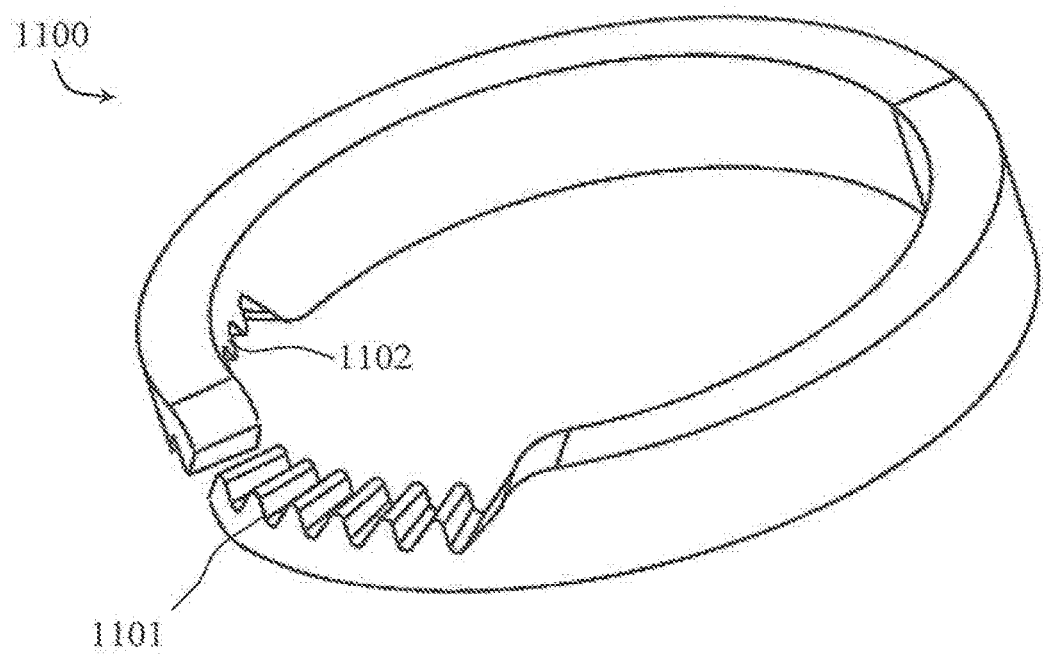
Figure 98:
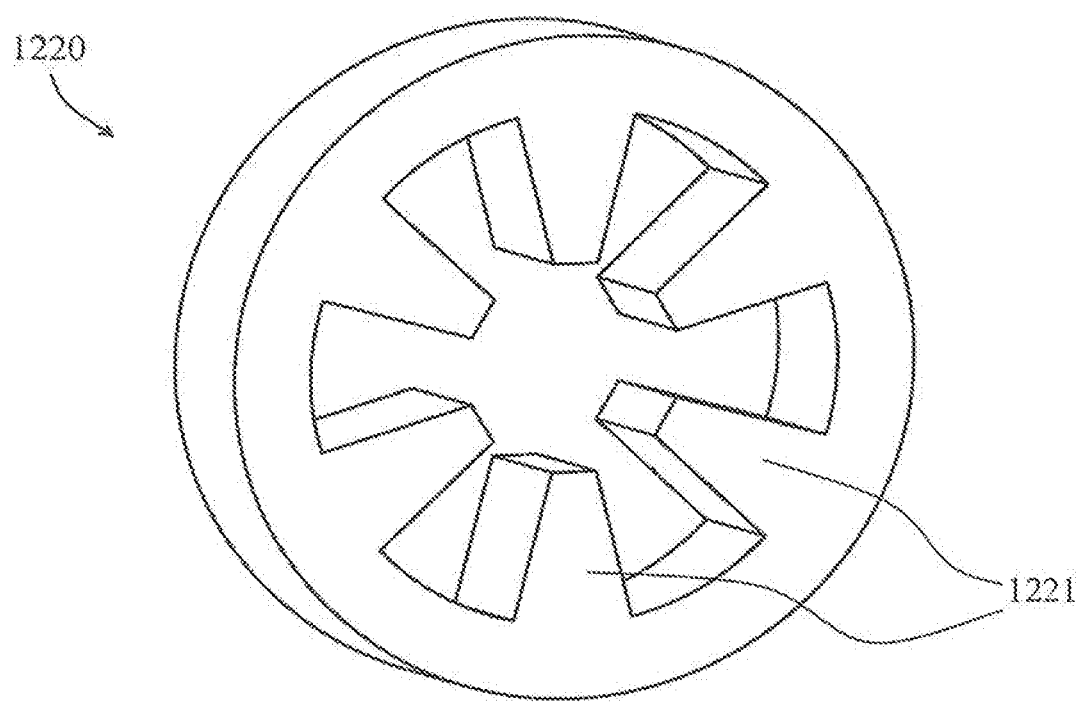
Figure 99:
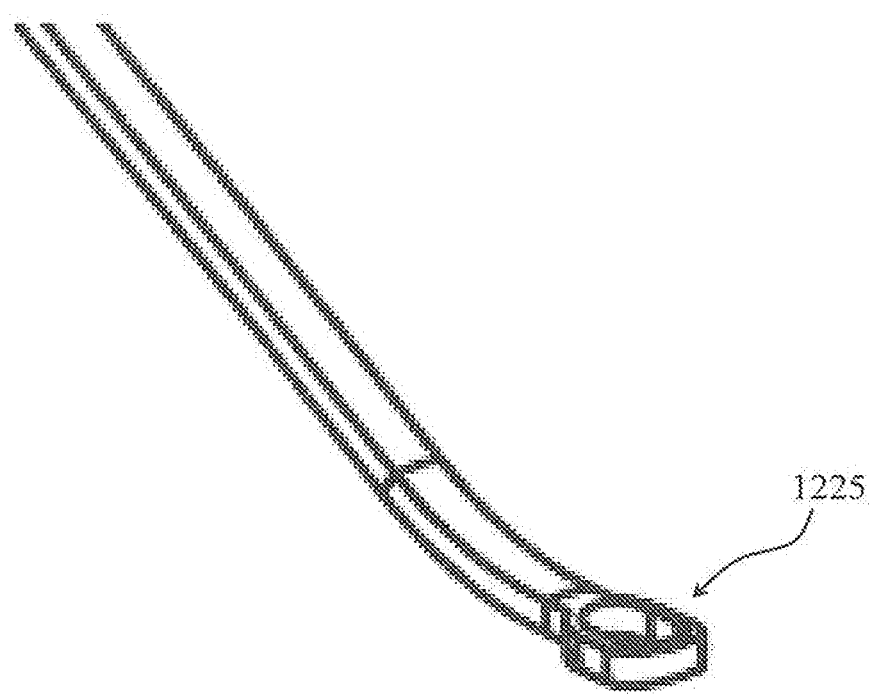
Figure 100:
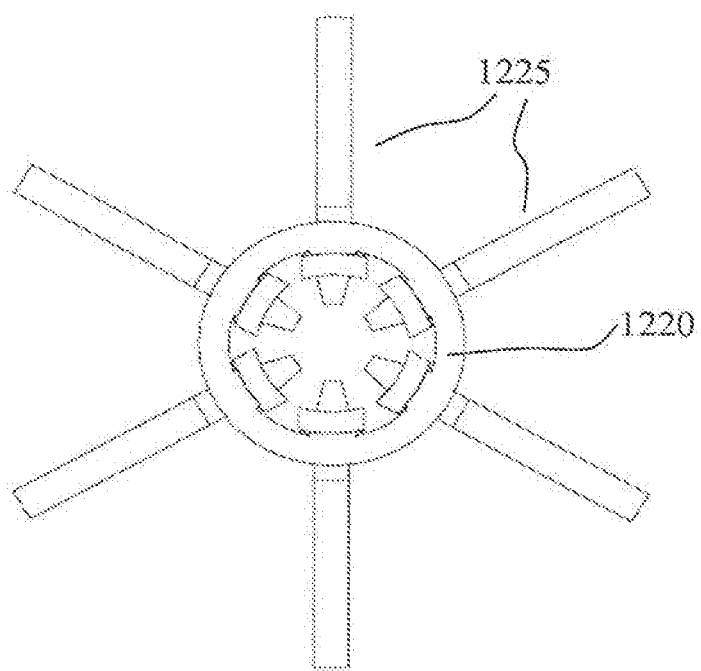
Figure 101:
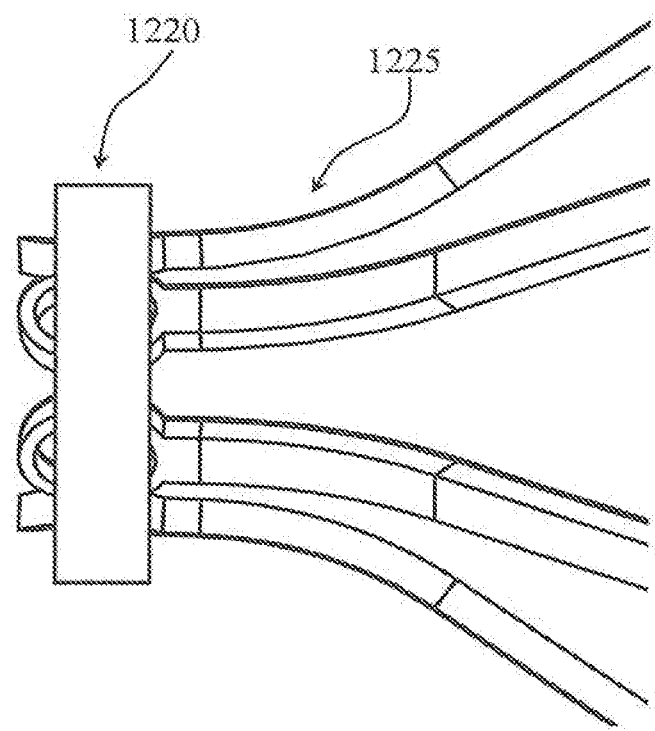
Figure 102:
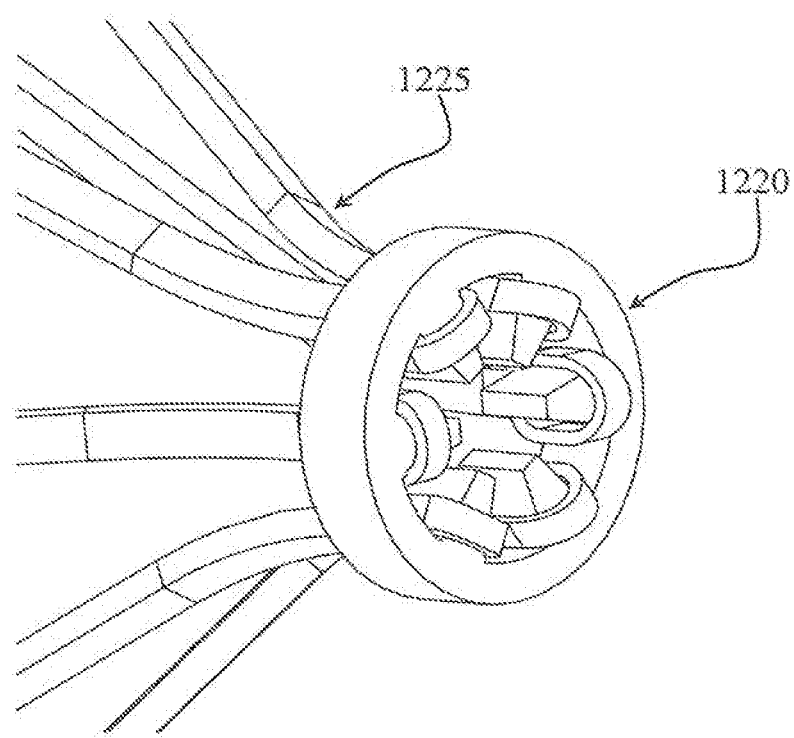
Figure 103:
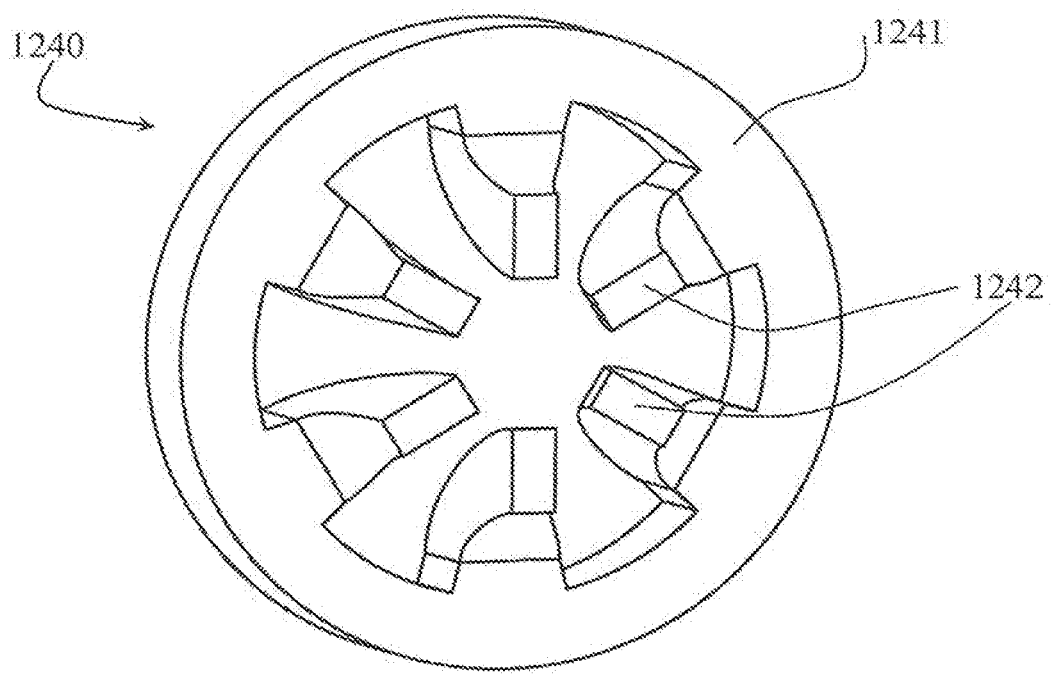
Figure 104:
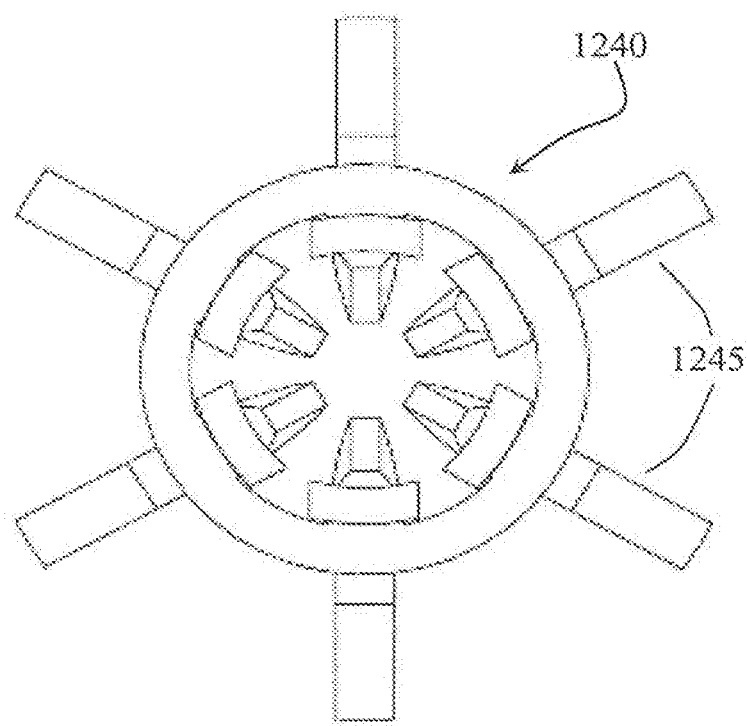
Figure 105:
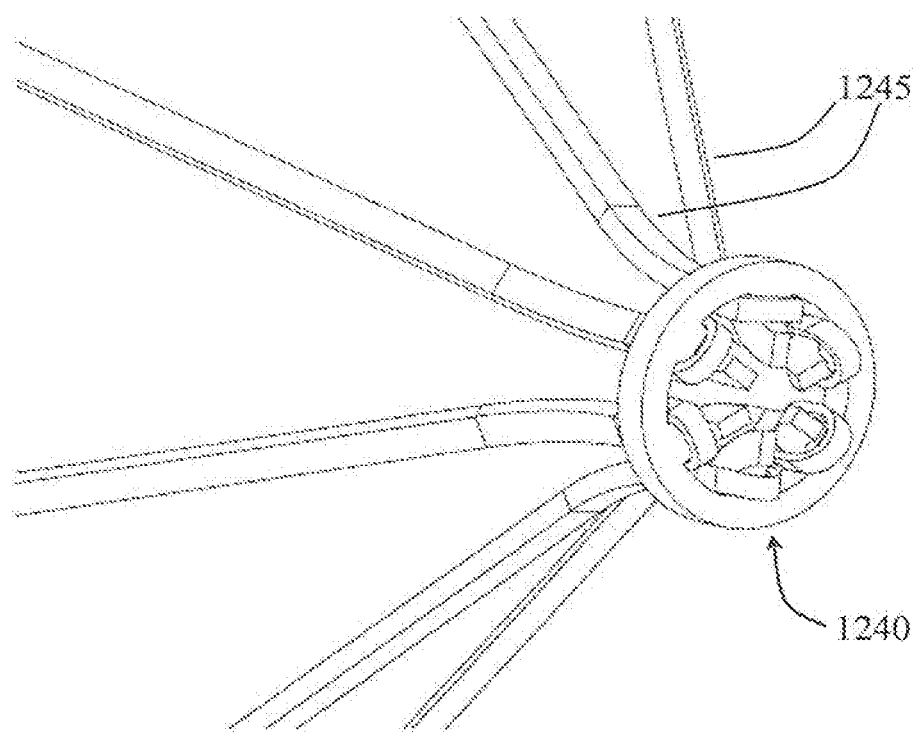
Figure 106:
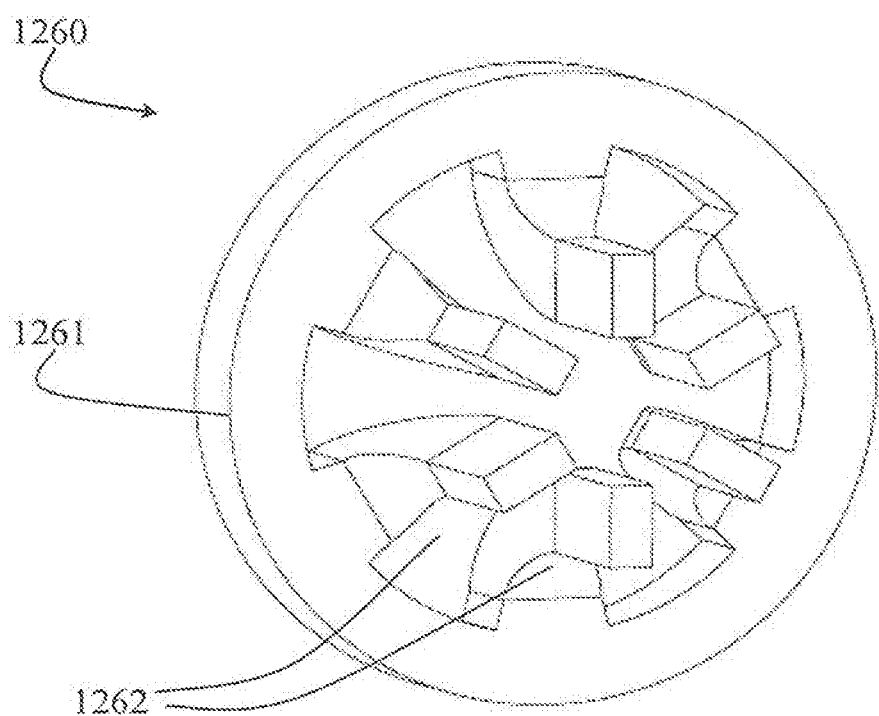
Figure 107:
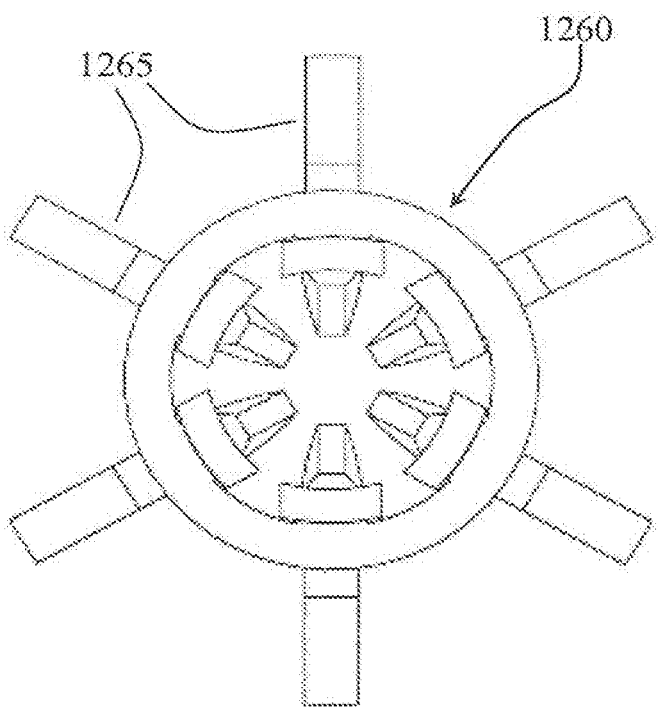
Figure 108:
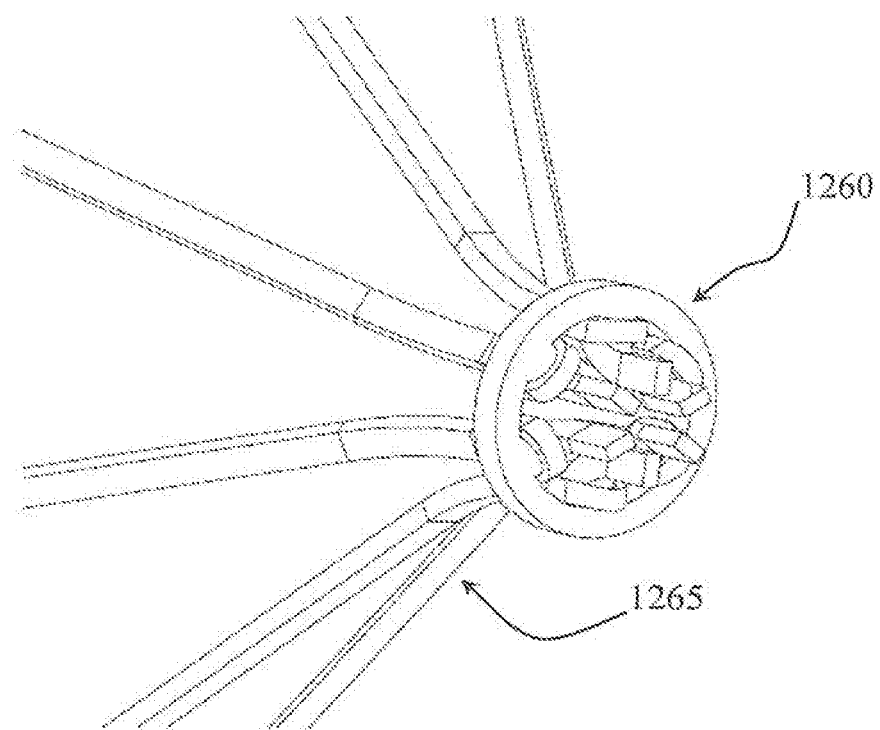
Figure 109:
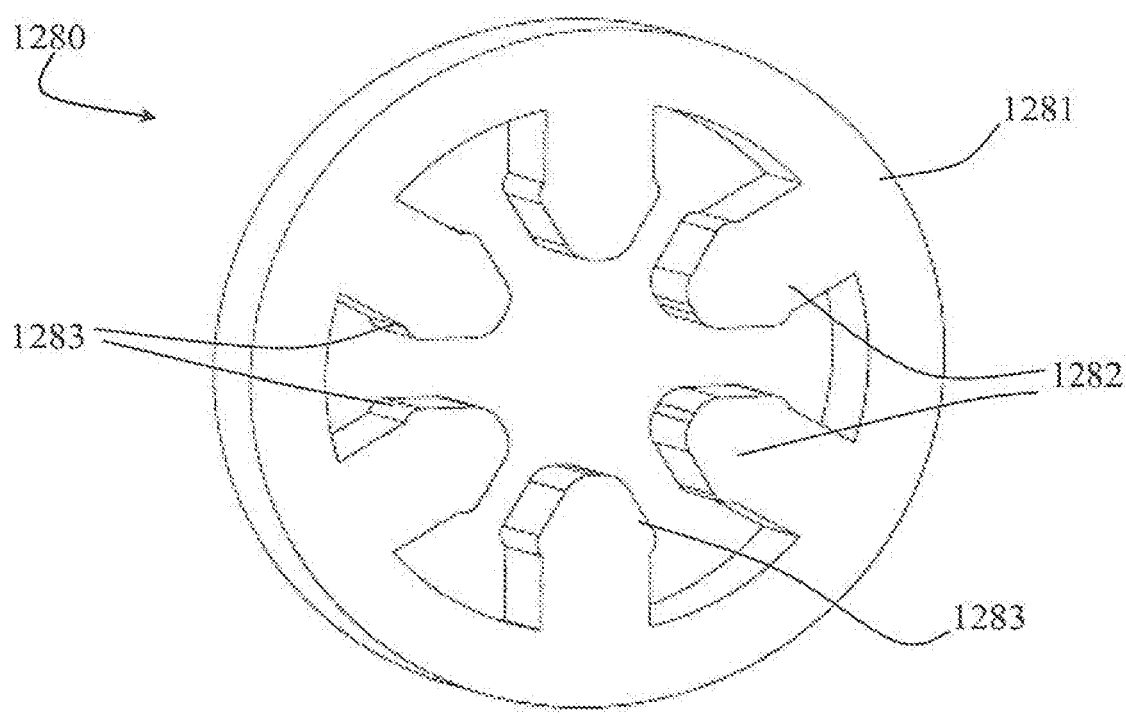
Figure 110:
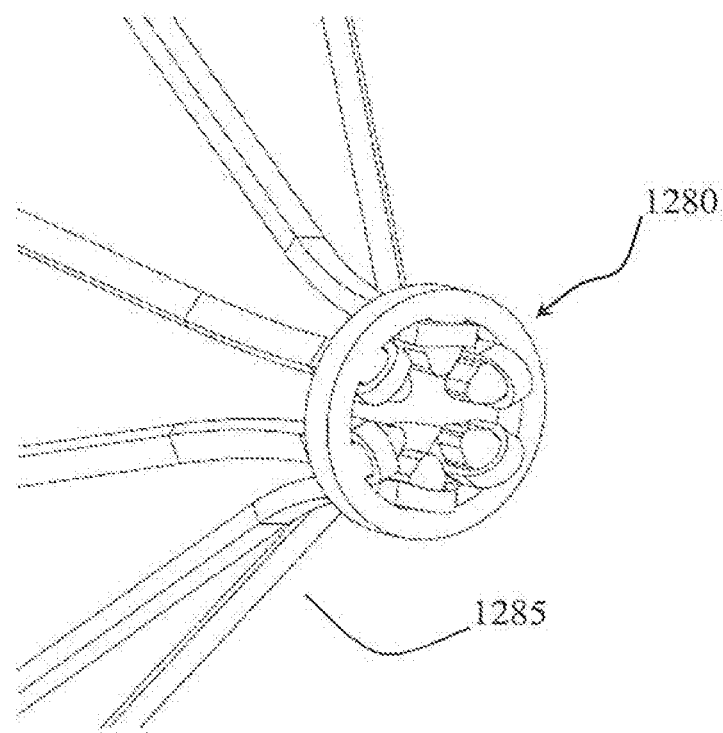
Figure 111:
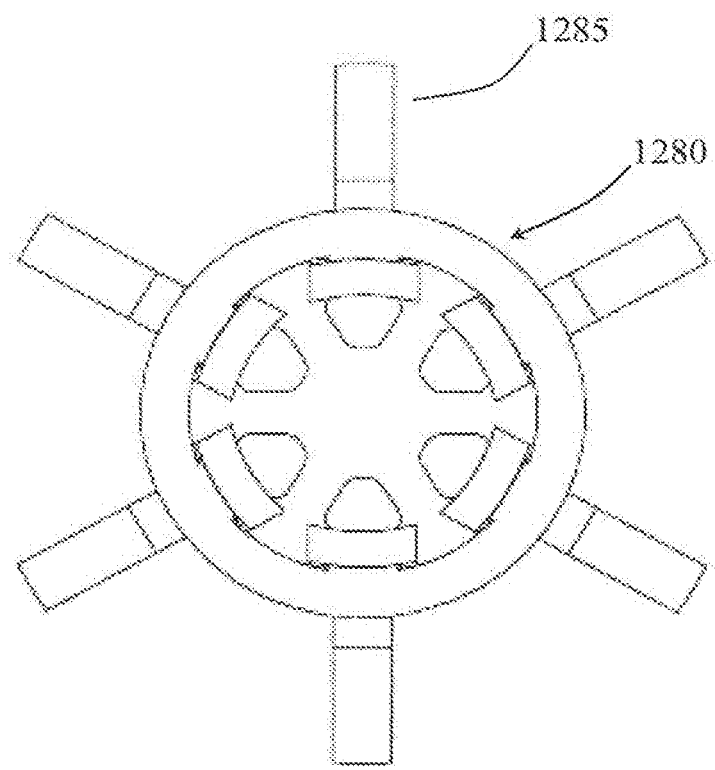
Figure 112:
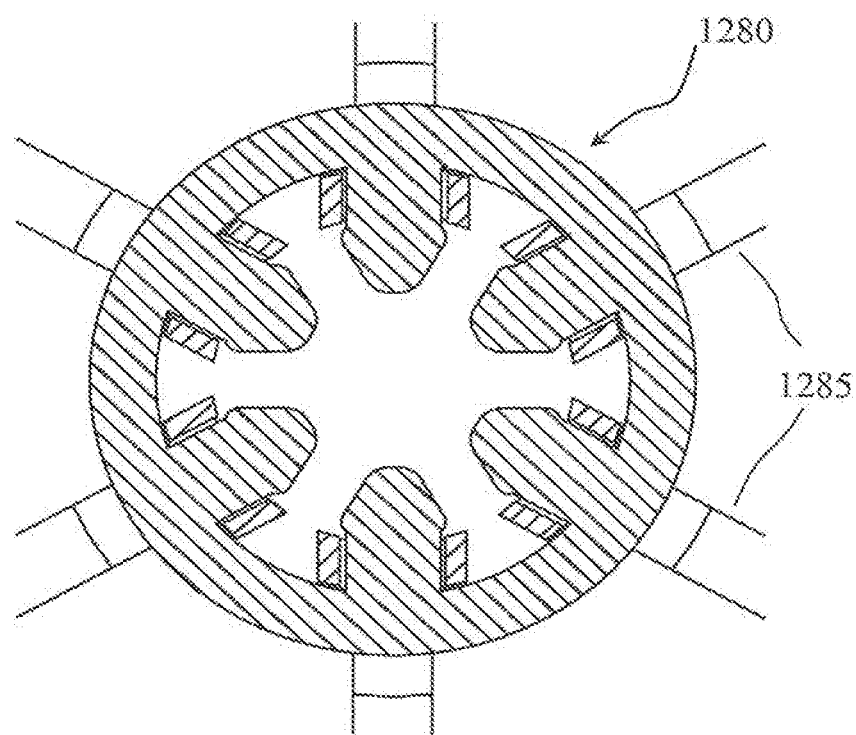
Figure 113:
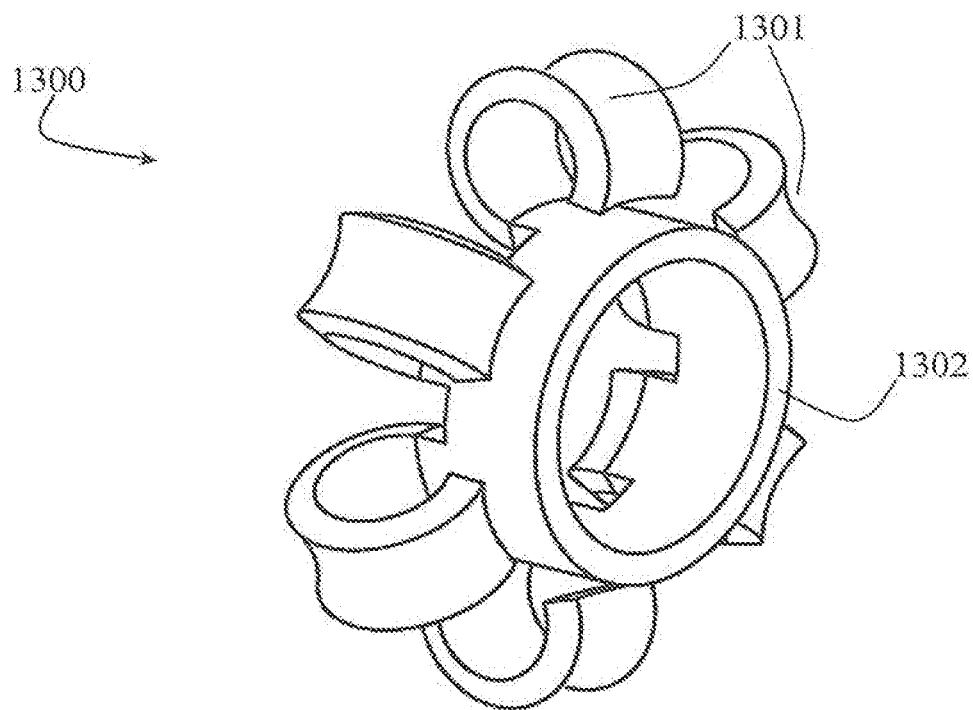
Figure 114:
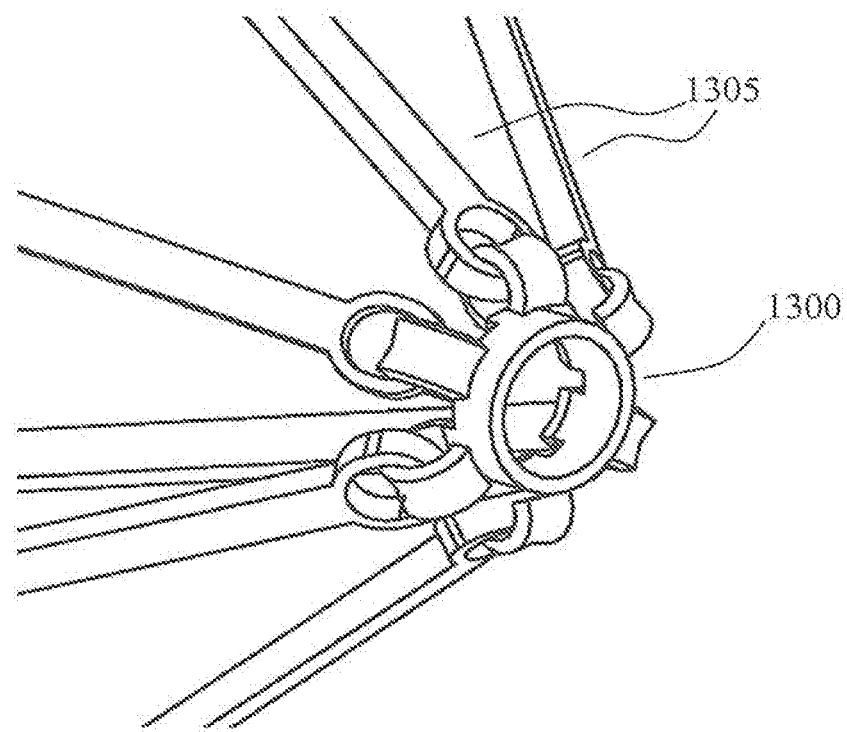
Figure 115:
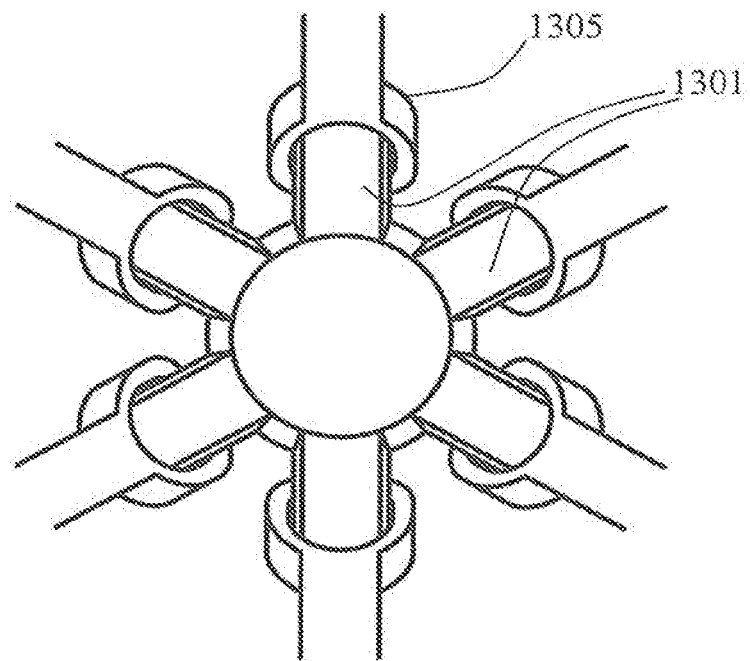
Figure 116:
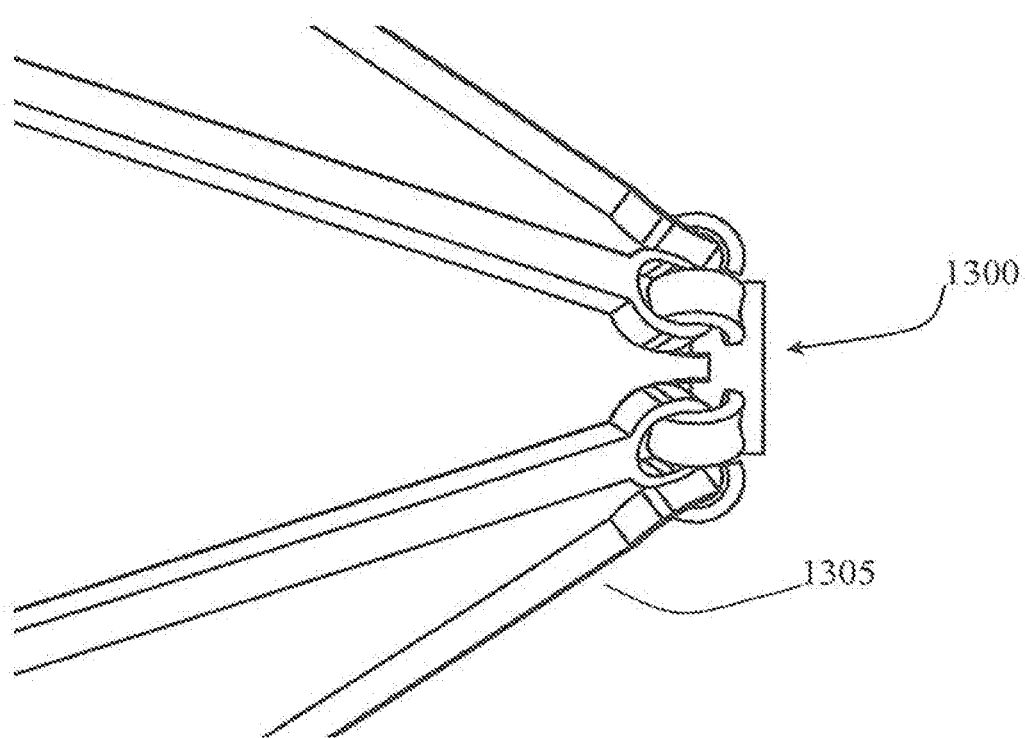
Figure 117:
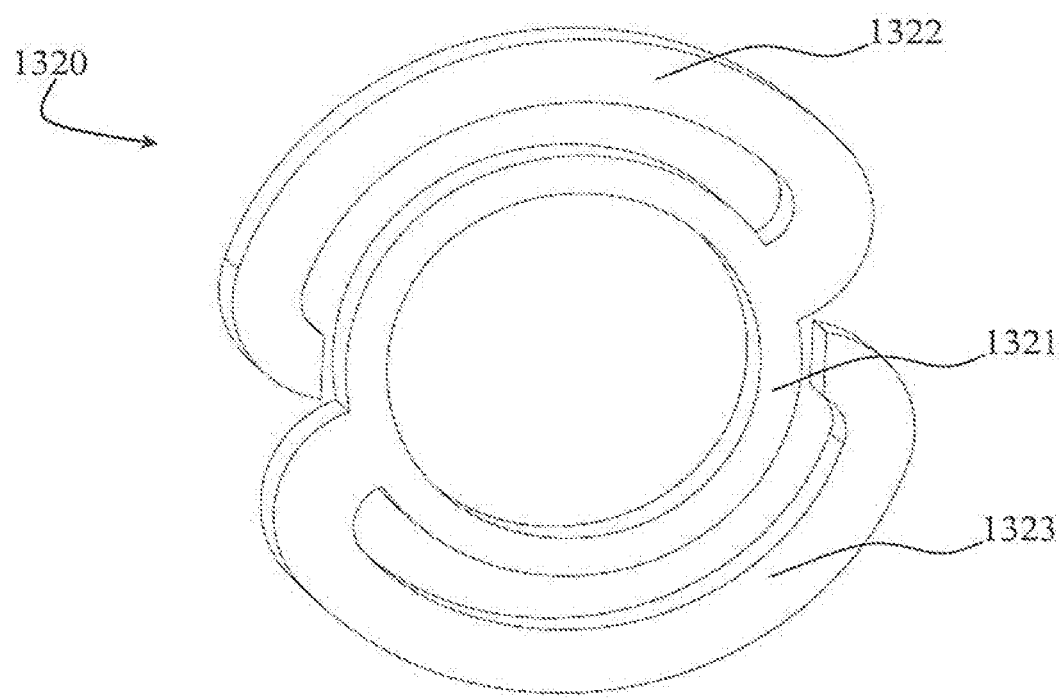
Figure 118:
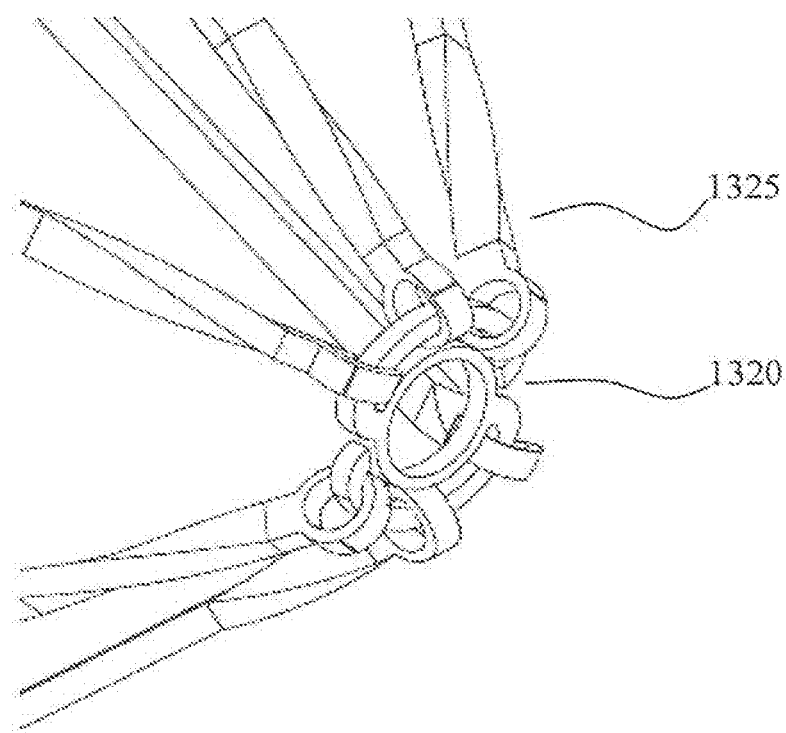
Figure 119:
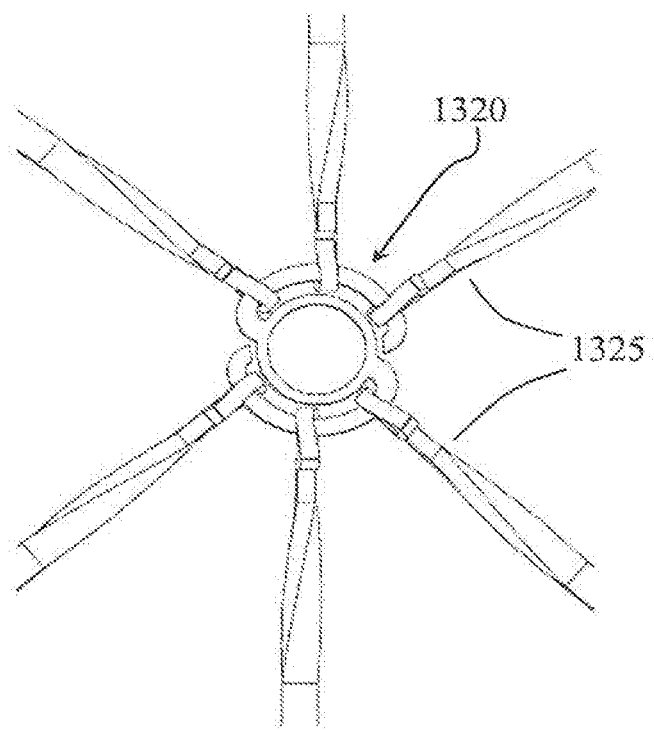
Figure 120:
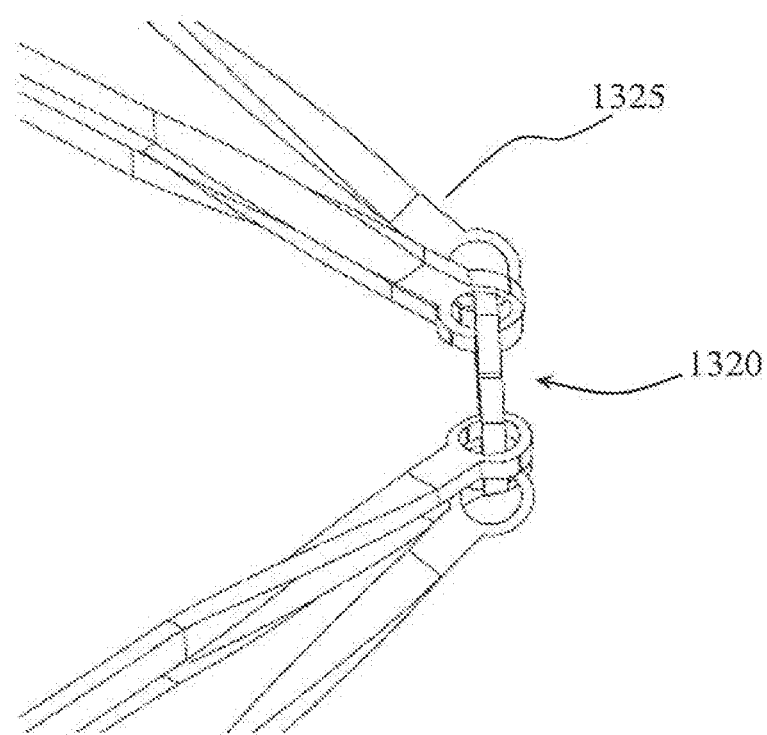
Figure 121:
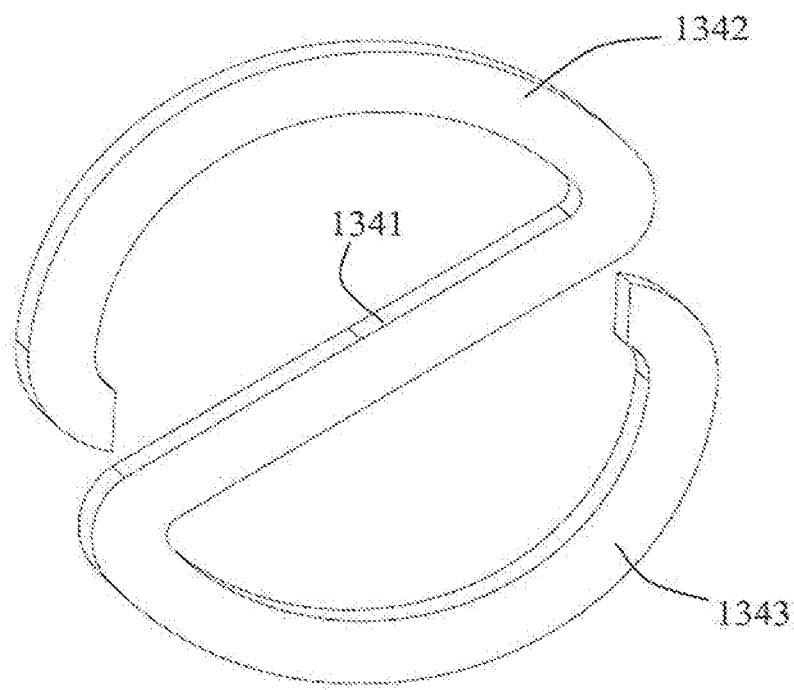
Figure 122:
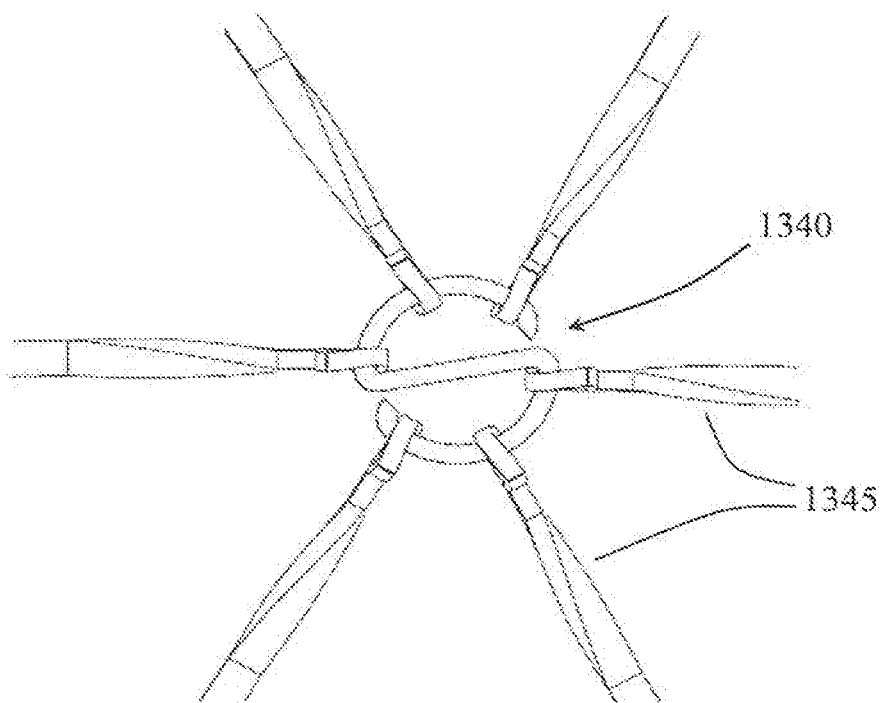
Figure 123:
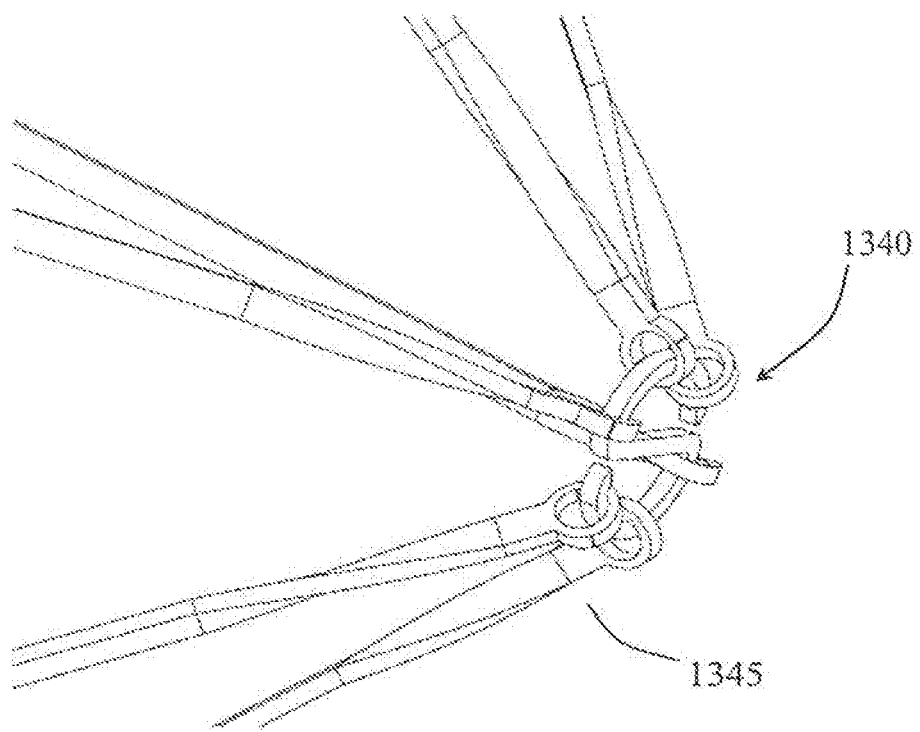
Figure 124:
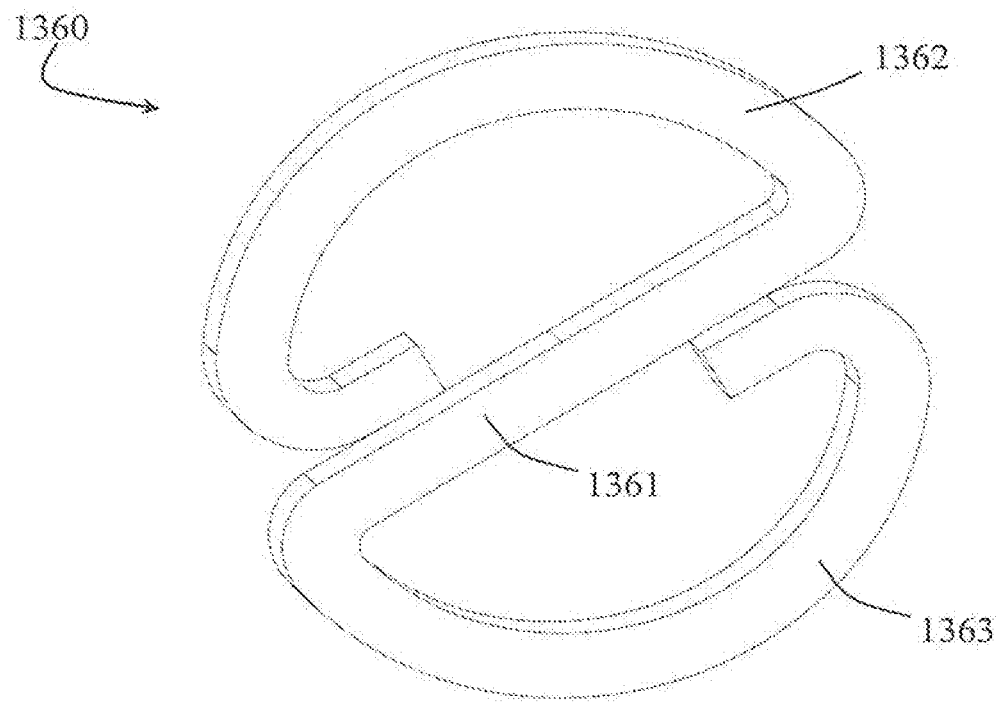
Figure 125:
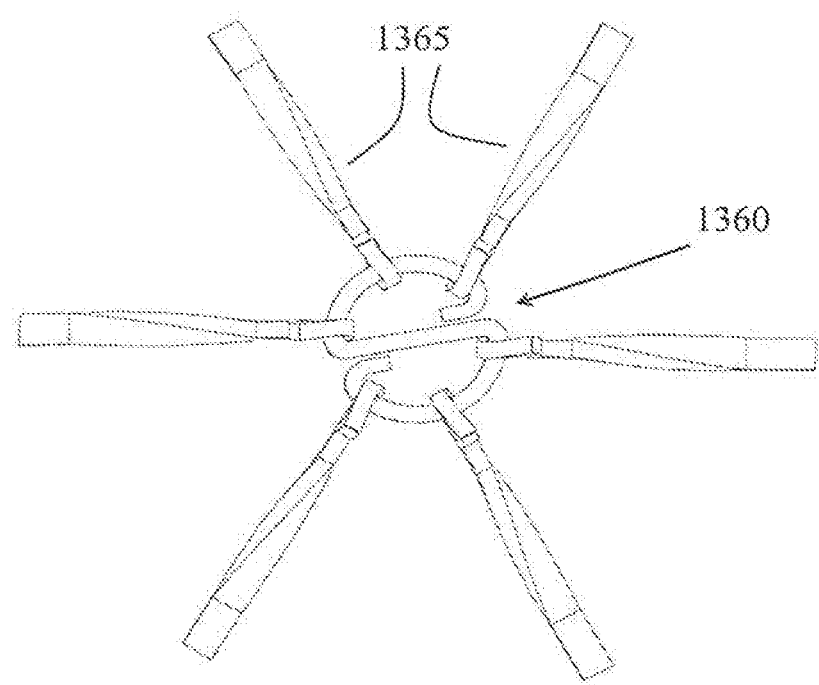
Figure 126:
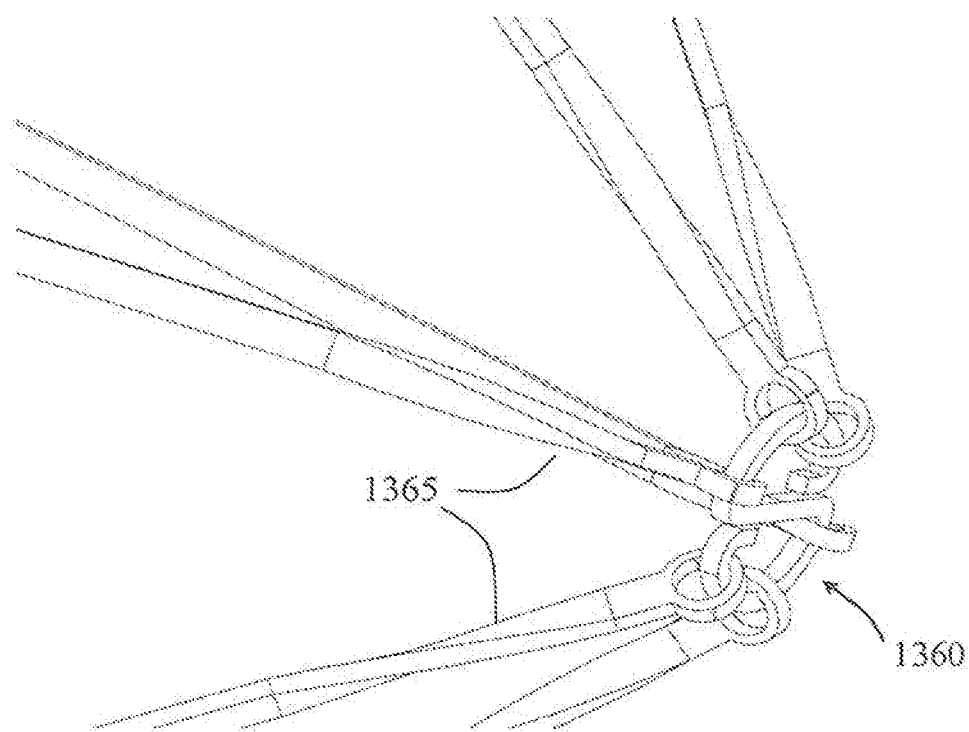
Figure 127:
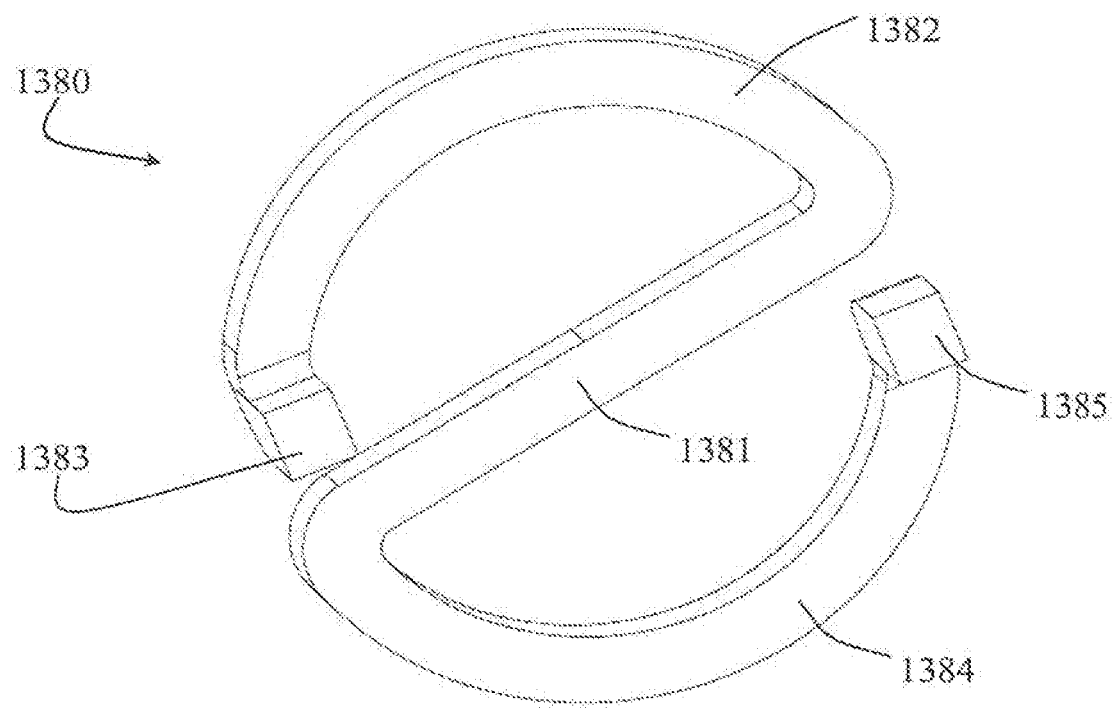
Figure 128:
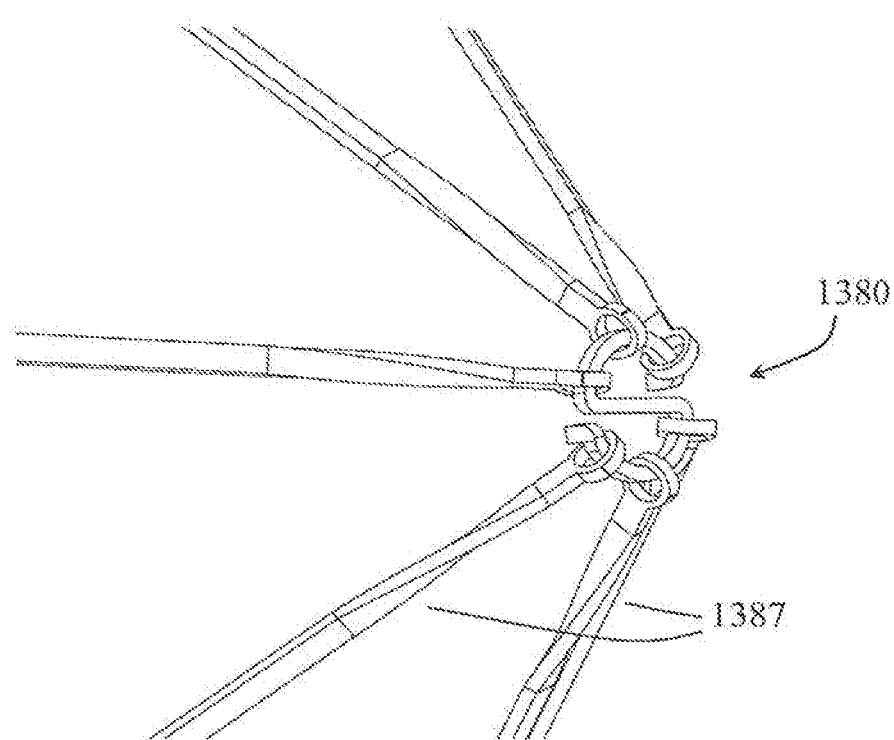
Figure 129:
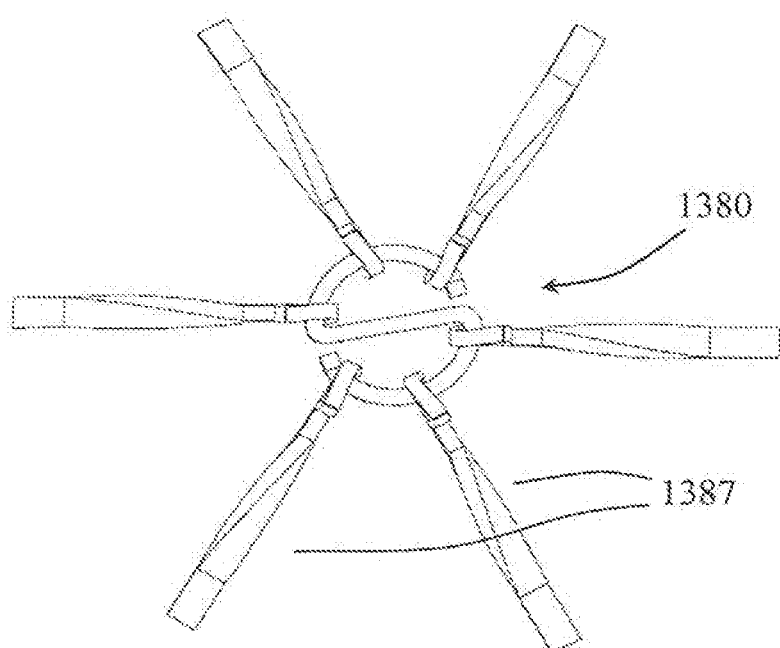
Figure 130:
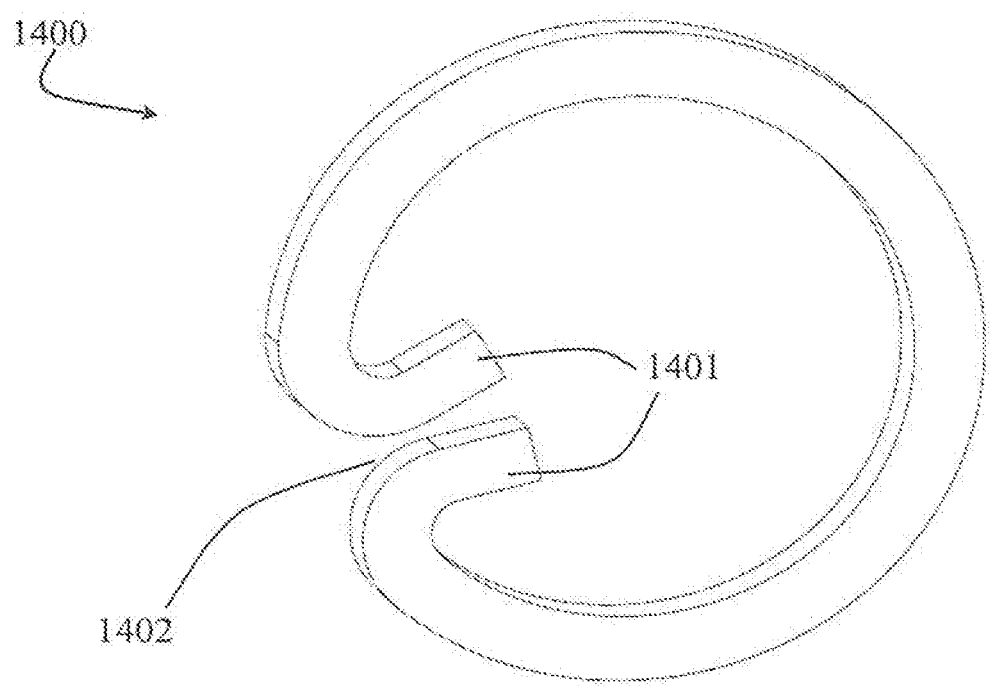
Figure 131:
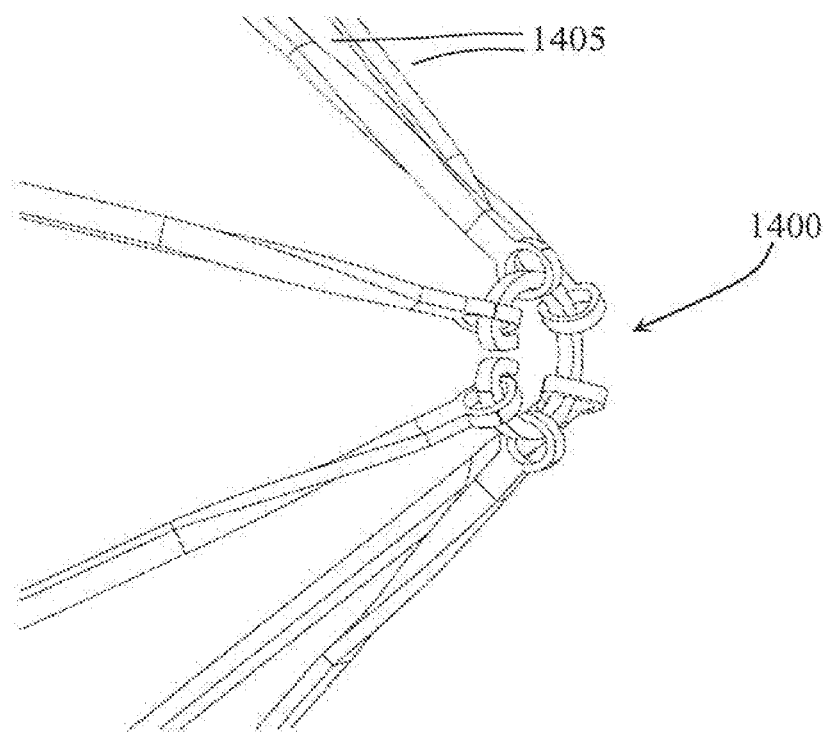
Figure 132:
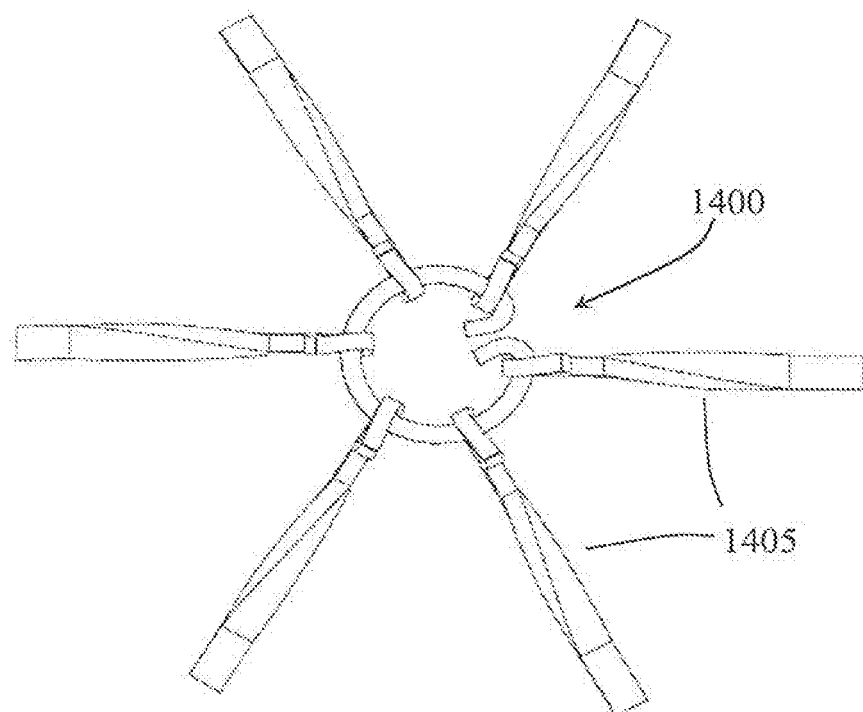
Figure 133:
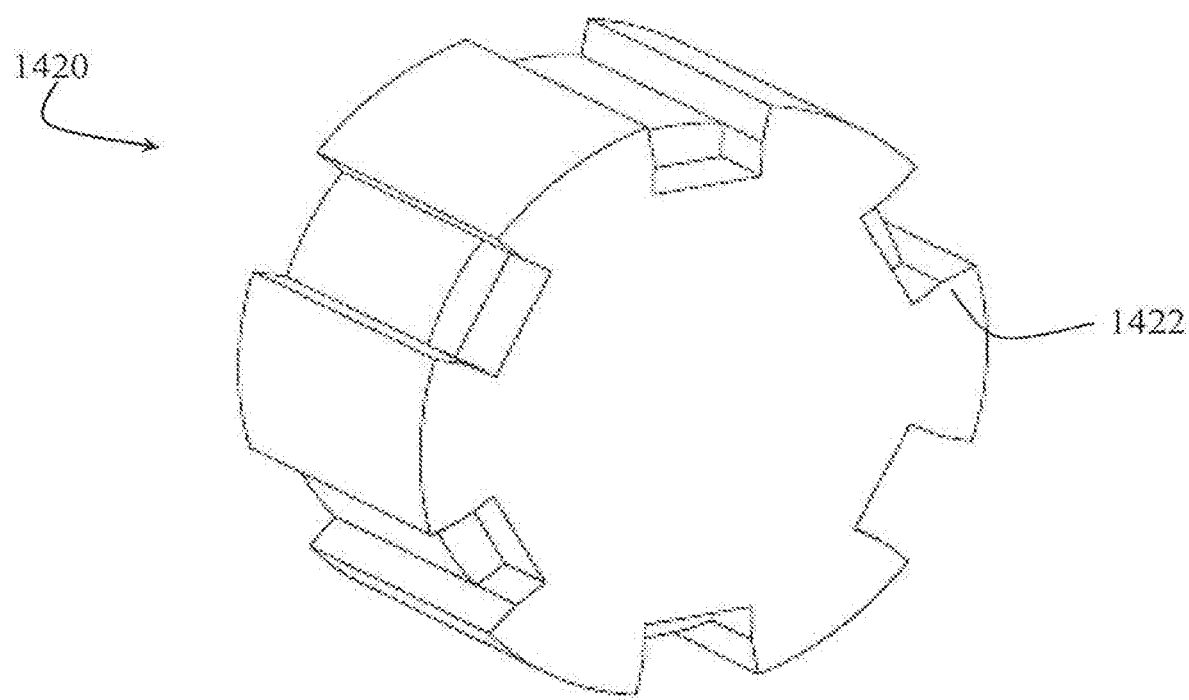
Figure 134:
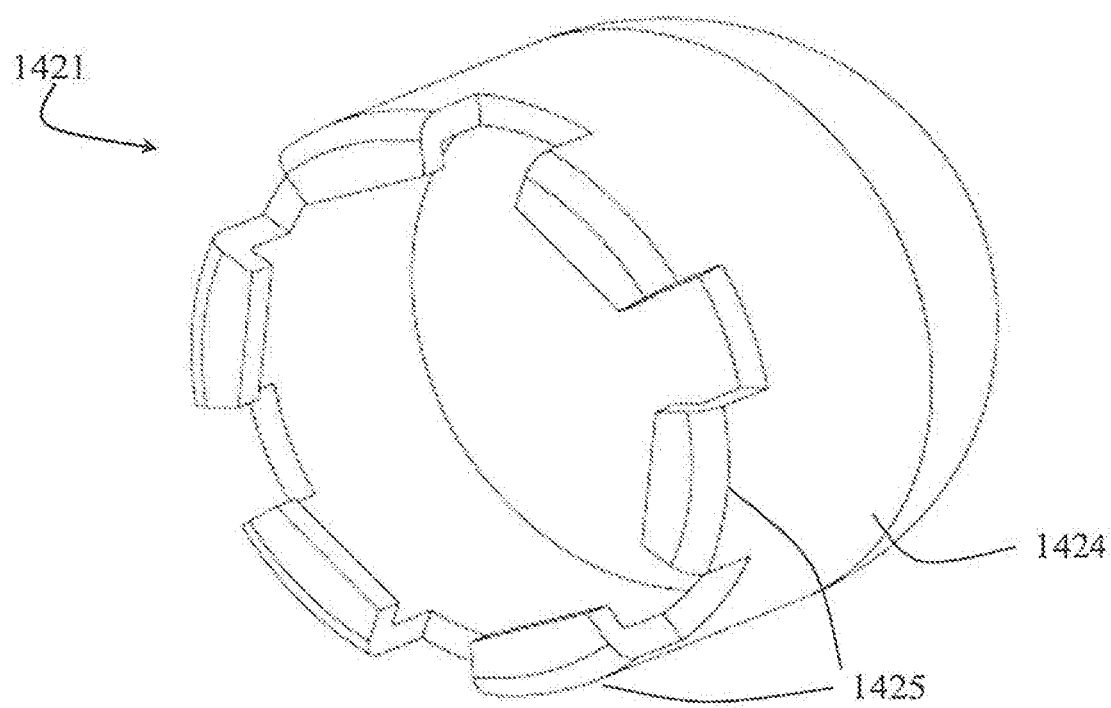
Figure 135:
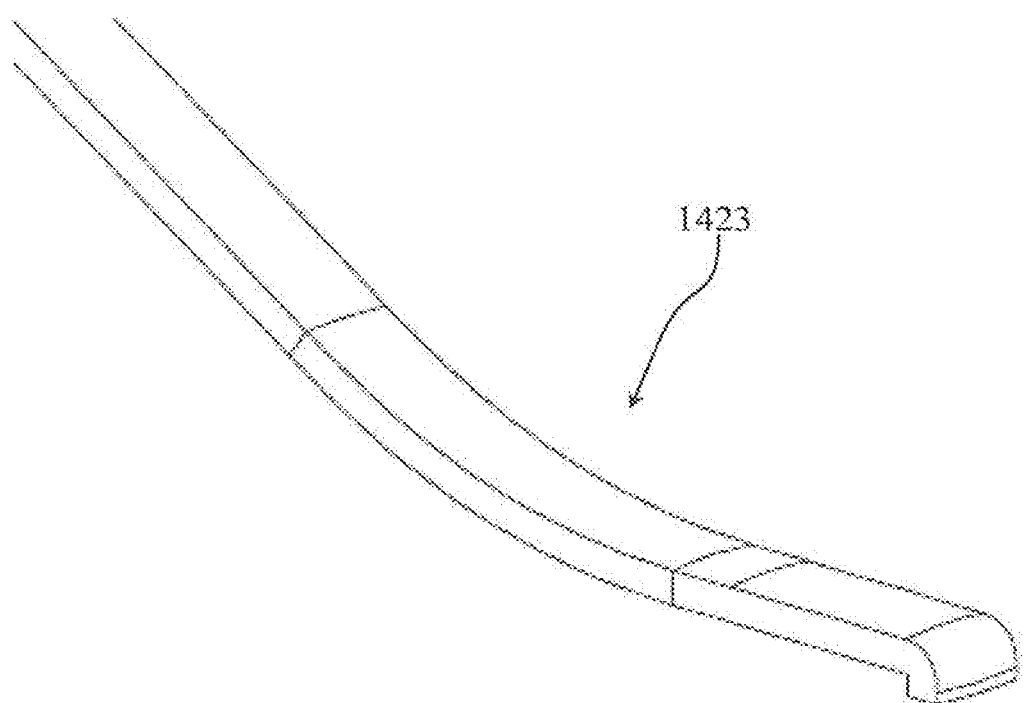
Figure 136:
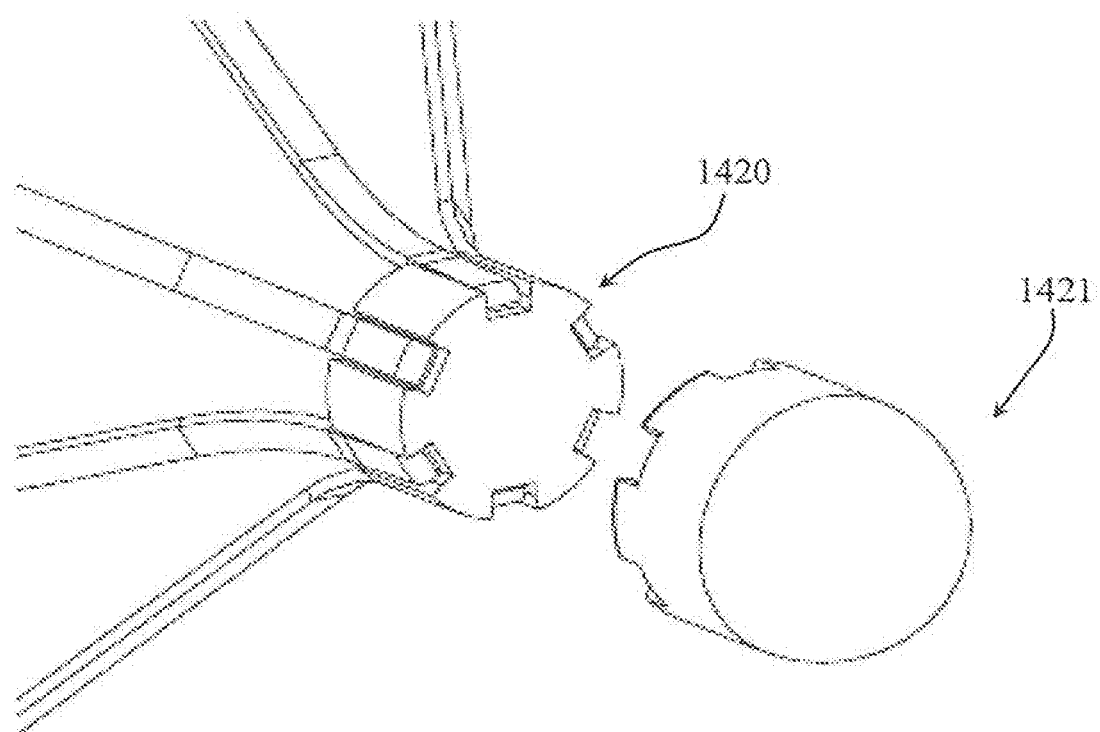
Figure 137:
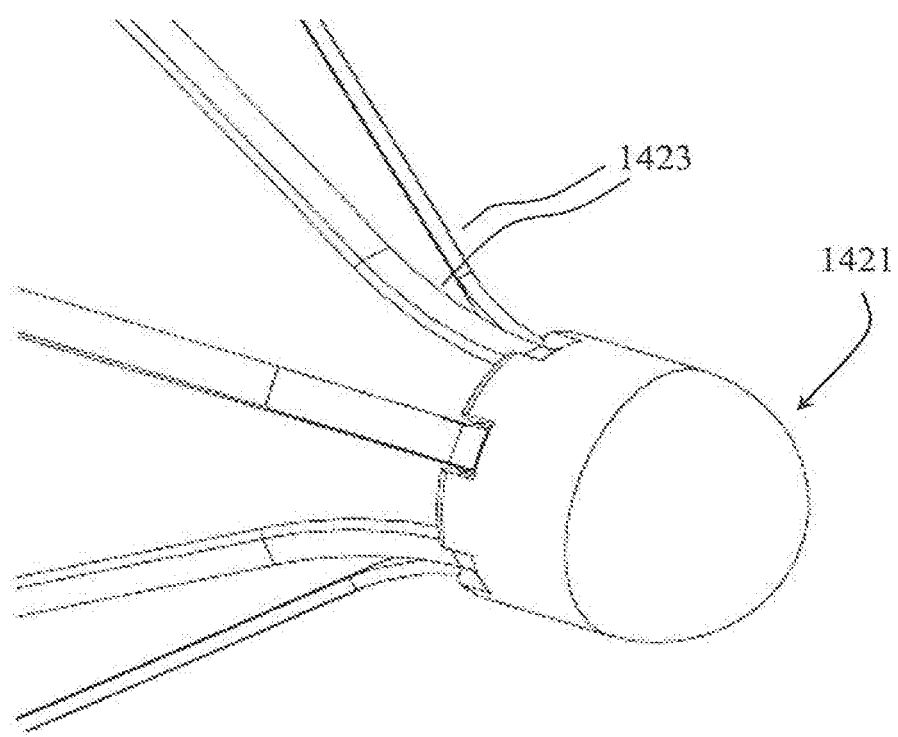
Figure 138:
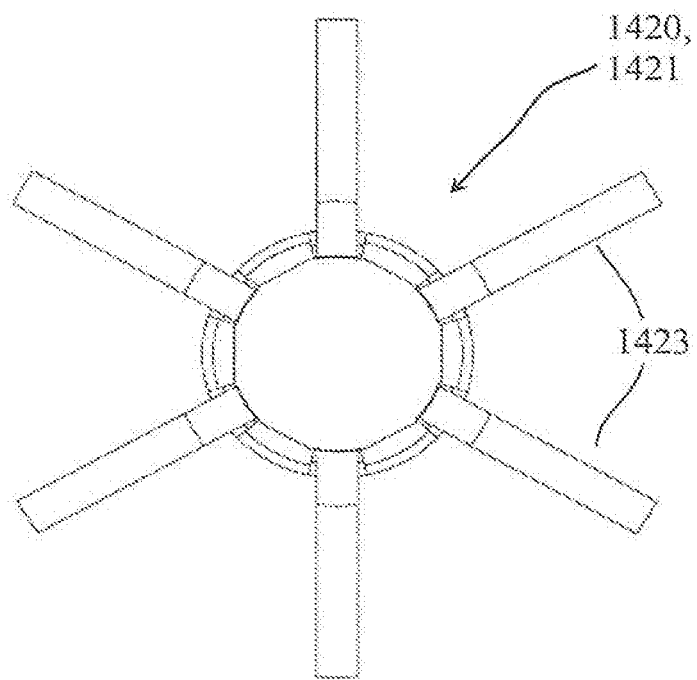

FIGS. 9A and 9B are a set of side views of the present invention showing only top and bottom filter elements, in which the top image (FIG. 9A) depicts the filter elements in a relaxed state without a holder when constrained in a vessel. Dotted lines depict the filter elements forming a central apex, and the bottom image (FIG. 9B) depicts the filter elements in a relaxed state with parametric designations;

FIGS. 10A and 10B a set of cross sectional views of a filter element of the present invention, in which the image to the left (FIG. 10A) depicts the filter element profile as cut from a raw tube shown in broken lines, and image to the right (FIG. 10B) gives parametric designations to the cross section;

FIG. 11 is a cross sectional view of a filter element of the present invention with further parametric designations;

FIGS. 12A and 12B include a cross-sectional side view and an end view of crimping of the filter elements at the apex, FIGS. 13A and 13B, and 14A and 14B show how a pin may be used for this purpose, and FIG. 15 shows the use of a multi-lumen tube for this purpose;

FIGS. 16A-16F show two types of holder caps for retaining the filter element at the apex; FIG. 17 shows how the filter elements may be twisted together;

FIGS. 18A-18E show filter elements which are configured at their ends for interconnection;

FIGS. 19A-19E show such interconnection with dovetail inter-locking;

FIG. 20 is a perspective view of a filter device of the invention during manufacture, and FIGS. 21A-21C and 22A-22E show parts in greater detail;

FIGS. 23A and 23B and 24A-24D show expanded parts of the device, and FIGS. 25A-25C show the parts connected together;

FIGS. 26A and 26B show the laser cut pattern;

FIGS. 27A-27F shows the assembled device and highlights the integral apex;

FIGS. 28A-28D show an integral proximal support, filter arms and apex with a separate distal support and connector arms and FIGS. 28E-28F show a separate support and integral filter elements and apex;

FIGS. 29A-29D show a separate support and FIGS. 29E-29H show a separate filter, and FIGS. 30 and 31A-31F show the assembled device;

FIGS. 32A-32D show a device in which the distal hoop is provided as a separate piece, and FIGS. 33A-33D show a device in which the connection points are on the filter elements;

FIGS. 34A to 41 show various methods of making the connections;

FIGS. 42 and 43 show methods of reducing the crimped outer diameter;

FIGS. 44A to 47B show an arrangement in which the filter apex is connected to a distal support hoop; FIGS. 48A to 53C show embodiments in which the apex is not fully closed in shape in axial view;

FIGS. 54A to 57C show different arrangements of connector struts;

FIGS. 58A-58B, 58C-58D, 59A-59B, 59C-59D, 60A-60B, and 60C-60D are each a pair of side and end views of filter devices of the invention;

FIGS. 61A-61D include a set of plan, elevation, end and perspective views of a further device of another embodiment;

FIGS. 62A-62C include a set of side, end, and perspective views of an integral apex of one embodiment;

FIG. 63 is a laser cut pattern for a device of one embodiment;

FIGS. 64A and 64B are a side view and end view of a device of an alternative embodiment;

FIGS. 65A and 65B are a pair of views showing filter element connections of devices of alternative embodiments;

FIGS. 66A and 66B are a side and end view of a further device;

FIGS. 67A-67C are a set of side and laser cut pattern views of the device shown in FIGS. 66A and 66B; FIG. 68 is a view of an alternative filter element; FIGS. 69A and 69B are views of an alternative connector element;

FIGS. 70A-B, 71A-B, 72A-B, 73A-B 74A-B include side views and end views of alternative filter devices of the invention, and FIG. 73C is a perspective view of a portion of FIG. 73A;

FIGS. 75A-75C include a set of plan, elevation, and end views of a further device of the invention; FIGS. 76A and 76B are perspective and laser cut pattern views of the device shown in FIGS. 75A-C respectively;

FIG. 76C is a view of an alternative laser cut pattern of the device shown in FIGS. 75A-75C to 76B;

FIG. 77 is a view of the Inferior Vena Cava (IVC) showing the iliac veins, renal veins and implant length for a device of the invention;

FIGS. 78A-78D to 79A-79D are each a set of plan, elevation and end views of alternative filter devices of the invention;

FIG. 80 and is a perspective view of a holder of one embodiment, for interconnecting or holding the filter element ends together in an apex, in which the holder is formed by a spiral;

FIG. 81A is a perspective view of an alternative spiral holder, and FIGS. 81B and 81C-81F show this holder in use;

FIGS. 82, 83 and 84 are perspective views showing alternative holders of the overlapping spiral or "key ring" type;

FIGS. 85 to 93 are perspective views of holders which can be trained through eyelets of filter element ends but are not of the overlapping spiral type, FIG. 85 showing a holder of the split ring type, FIGS. 86 and 87 showing holders in which one end forms a hook which passes through a loop at the other end, FIG. 88 shows another holder of the split ring type, and FIGS. 89 to 93 show holders in which a male end fits into an opposed female end;

FIGS. 94 to 97 show holders which have prongs for extending through filter element end eyelets and are biased radially inwardly for closure;

FIG. 98 is a perspective view of a holder which has prongs directed radially inward for engagement in eyelets such as the type shown in FIG. 99, as shown in FIGS. 100 to 102; FIG. 103 shows a variation in which the prongs extend both radially inward and are turned to be partly on-axis for engagement with eyelets as shown in FIGS. 104 and 105;

FIG. 106 shows an alternative holder, with a completely on-axis prong end and FIGS. 107 and 108 show it in use;

FIG. 109 shows a further holder, again having inwardly radially-directed prongs, and FIGS. 110 to 112 show this holder in use, in which FIG. 112 is a cross-sectional view showing snap-fitting engagement of the prongs through the filter element end eyelets;

FIG. 113 shows an alternative holder, having hooks on an annular base, there being one hook per filter element end, and FIGS. 114 to 116 show this in use;

FIG. 117 shows a holder having two arcuate hooks in a plane through the device and being on an on-axis ring base, each hook being configured to accommodate half of the filter element ends, and FIGS. 118 to 120 show the holder in use;

FIG. 121 shows a holder with two opposed hooks in an arrangement broadly similar to that of FIGS. 117 to 120, except that the hooks extend from opposite ends of a common radially-extending member to form an S-shape, and FIGS. 122 and 123 show the holder in use;

FIG. 124 shows a holder which is similar in principle to the holder of FIG. 121, the main difference being that the ends of the hooks are more turned-in, and FIGS. 125 and 126 show it in use;

FIG. 127 shows a further variation in which the ends of the hooks have abutments which are are turned on-axis, and FIGS. 128 and 129 show it in use;

FIG. 130 shows a holder in the form of a C with the ends turned in to form a non-reentrant opening, and FIGS. 131 and 132 show it in use; and FIGS. 133 to 139 show an alternative holder, in two parts having a central core which fits between the filter element ends and an outer ring which fits over the core and the filter element ends to clamp them together to form an apex.

DESCRIPTION OF THE EMBODIMENTS

Shape Set Filter Elements

Referring to FIGS. 2 to 6 a vascular filter device 1 of the present invention is manufactured by providing a part 2 with a support 3 and filter elements 4 which are formed to bend inwards and converge towards a central apex. The filter elements s are interconnected using a holder 6 to form a central apex 5 on a central axis of the device.

In more detail, in one embodiment the filter device 1 is formed from a laser cut NiTi shape memory alloy tube by expanding and constraining the device in a fixture or on a mandrel and then performing a heat treatment step to set the new shape. This method is referred to here as shape setting. The device can then be crimped down to a diameter that is greater than, equal to, or less than that of the raw tube and loaded into a delivery sheath for low profile delivery to the implant site. When deployed into an environment that is above the Af temperature, the filter will revert to its expanded form provided by the shape setting step (for example, if the material's Af temperature is 20° C., it will revert to its shape set form in an environment that is above 20° C. such as that of blood at 37° C. It is appreciated that materials without shape memory properties may alternatively be used. In this embodiment, the filter elements can be manually formed into a shape and then heat treated, annealed, to remove stresses and strains introduced through work hardening. The preferred embodiment uses shape memory materials as they are capable of withstanding much higher strains.

Improvements are made to the prior art device in that the present invention reduces filter element strain at the connection to the support frame. Vena cava filters operate in an environment in which the filter experiences deflections at a rate of approximately 70/min radially and approximately 20/min longitudinally due to pulsatile blood flow and respiration respectively. Therefore, reduced filter element strain will improve durability, fatigue performance and fracture resistance. In order to reduce filter element strain during use in a blood vessel, the filter may be shape set with the filter elements forming the central apex without a coupling means when constrained in the indicated vessel size. This would remove filter element strain when the filter device is placed in a blood vessel of the indicated vessel size as the filter elements would be in a relaxed state along their length and at the connection to the support frame. It is beneficial to oversize the device in order to provide sufficient radial force that will prevent migration and enhance deployment accuracy. The device over sizing should be applied in a balance so as not to provide excessive radial force that may cause transmural migration (movement of the device through the vessel wall) or perforation. With an oversized device, the filter shape setting step should provide filter element ends that form a central apex when constrained in the intended vessel size indication without the use of a coupling means to interconnect the filter elements at an apex. The shape setting step may be sufficient to keep the filter closed once adequate stiffness is attributed to the filter elements so that they exhibit no movement or minimal movement upon impact of a blood clot. In another embodiment, a coupling means is added to strengthen the apex to withstand the impact of blood clots and vessel movement. The coupling means may be provided by way of a holder or a feature(s) on the filter elements that interconnect the filter elements.

Figure 6E:
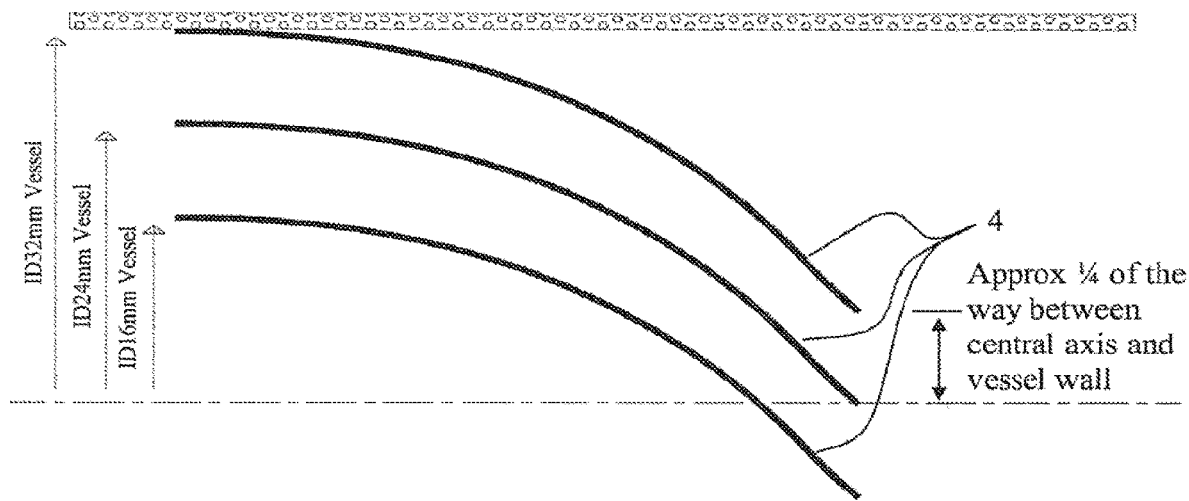

The device of the present invention may be indicated across a vessel size range, ideally from 16 mm to 32 mm internal diameter. In this embodiment, the filter may be shape set with the filter elements curved radially inwardly so that the filter element ends are positioned approximately one quarter of the way between the central apex and the vessel wall (4 mm) if the filter part 2 is constrained in the upper vessel size of 32 mm. Alternatively, the filter may be shape set with the filter elements curved radially inwardly so that the filter element ends form a central apex if the filter part 2 is constrained in the middle vessel size of 24 mm. Both situations are illustrated in FIG. 6(a) and FIG. 6(b). Then, the filter elements will have similar strain (in opposite bending directions) when placed in a 16 mm or 32 mm vessel. For example, if the filter device was constrained in the minimum indicated vessel of ID of 16 mm, the filter element ends would extend past the central axis as shown in FIG. 6(b)—approximately one quarter of the way (4 mm) from the central axis to the opposing vessel wall. However, when the filter element ends are coupled together using a holder, the filter elements press against opposing filter elements (applying compressive forces)—this is in contrast to when the filter is constrained in the maximum indicated vessel size of 32 mm where the filter elements pull against opposing filter elements (applying tensile forces). The diameter to form a central apex may be offset from the middle of the vessel range to account for structural considerations and ensure strains are similar when the device is implanted in the minimum and maximum indicated vessel sizes (i.e. equal or similar strain may be achieved when the filter elements are offset from the middle of the vessel size range due to offset centroid positions inherent in different filter element cross section profiles). In another embodiment, the diameter set to form a central apex may be chosen based on the mean of vessel sizes recorded in the literature in order to achieve minimum strain for the majority of implantations.

Figures 7A, 7B:
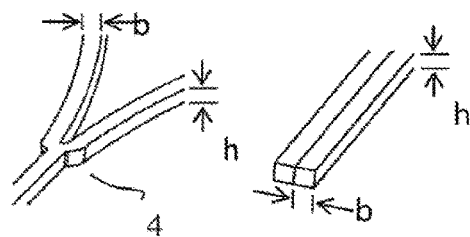
FIGS. 7A and 7B are a set of views showing a v-shaped filter element on the left (FIG. 7A) and two single filter elements on the right (FIG. 7B)

FIGS. 7A and 7B are a pair of views comparing a V-shaped filter element (FIG. 7A) to two single filter elements (FIG. 7B). Provided that b and h of the V-shaped filter element are equal to b and h of the two single filter elements, an approximation can be made that the second moment of area, I, for the V-shaped filter element is equal to that of two single filter elements.

Figure 8A:
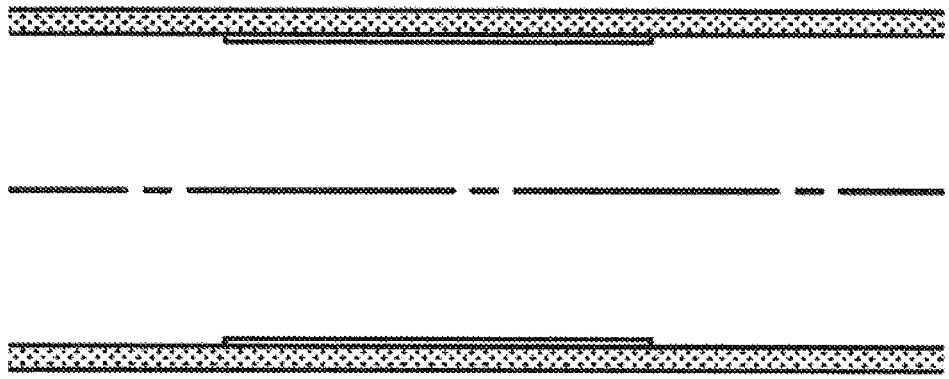
FIGS. 8A and 8B are a set of side views of the prior art showing only top and bottom filter elements, in which the top image (FIG. 8A) depicts the filter elements in a relaxed state without a holder when constrained in a vessel while the bottom image (FIG. 8B) depicts the filter elements pulled radially inwardly.
Figure 8B:
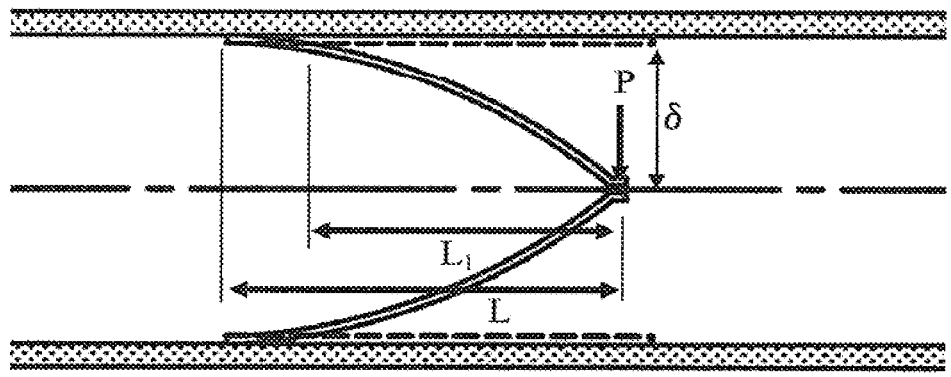

By way of comparison, FIG. 8A is a side view of the prior art device showing only the top and bottom filter elements in a relaxed state without the use of a holder when constrained in a vessel. The top and bottom filter elements are shown without the support frame for clarity. The proximal end of the filter elements are assumed to be in a fixed position as they are attached to the support frame. FIG. 8B is a side view of the prior art device showing only the filter elements with a holder coupling the filter element ends to form a central apex when constrained in a vessel. Also shown is the force, P, and deflection, δ, required to pull a filter element radially inwardly to the central apex. Assuming the filter element is a straight cantilever beam with uniform cross section, the filter element deflection, δ, is defined below where L is the axial length between the connection to the support frame and the filter element end, E is Young's modulus for the filter element material, and I is the second moment of area. $\delta = PL^3/3EI$ The strain on the surface of the filter element in bending at a point Li is $\varepsilon = My/EI = Mt/2EI$ where the moment $M = LiP$ Then, $\varepsilon = 3t\delta L_1/2L^3$ Filter element strain is highest at the connection to the support frame where Li=L. Filter element length is determined by balancing capture space (the volume of the capture cone increases with increasing filter element length) and parking space (parking space increases with increasing filter element length). Limited by the range of filter element lengths that will be adequate for capture space and parking space, it is preferred to control filter element strain by varying filter element thickness and/or deflection. Deflection is determined by vessel size for the prior art device leaving only the filter element thickness for strain control. Filter element strain reduces with decreasing filter element thickness; however, filter element thickness should be kept high enough to contribute sufficient radial force in order to prevent the filter device from migrating.

In order to improve the fatigue resistance, the present invention reduces the deflection, δ, in order to reduce the resultant strain.

FIG. 9A shows a simplified filter element profile of the present invention (support frame not shown). The relaxed filter element position in the upper vessel size is shown alongside the interconnected filter elements illustrated with broken lines. Assuming the filter element is a straight cantilever beam with uniform cross section, the bending equations can be described using Castiglianos thin curved beam theorem:

$$\delta_n = \frac{\delta U}{\delta P_n} = \int \frac{M}{EI} \cdot \frac{\delta M}{\delta P_n} dx = \int \frac{M}{EI} \cdot \frac{\delta M}{\delta P_n} \cdot r d\beta$$

Where, U=energy, P=force, M=moment, E=modulus, I=second moment of area, x=length, r=radius of arc, β=angle of arc, δ=deflection FIG. 9B shows angular relationships for the simplified filter element profile. The simplified filter element is shape set with an initial radius to point a subsequent straight section towards a central apex. It is appreciated that any filter element profile may be used to position the filter element in a deflection reducing configuration to inherently reduce filter element strain.

Using Castiglianos theorem, the filter element deflection, 5F, is expressed below.

$i5_F = \zeta - 1(L - \cos y) \cdot (L \cdot \cos y) dx +$ $\Gamma(I \cdot \cos y - t - r \cdot \sin\beta \cdot (L \cdot \cos y - \S - r \cdot \sin\beta)\tau \cdot \upsilon\beta I =$ $\frac{F}{EI} \left\{ \int_0^L (L \cdot \cos\gamma)^2 dx + \right.$ $\int_0^\beta (L^2 \cdot \cos^2\gamma + 2 \cdot L \cdot r \cdot \cos y \cdot \sin\beta + r^2 \cdot \sin^2\beta) r \cdot d\beta \right\} \cos -$ $y\cos + \frac{F}{EI} \left\{ \frac{L^2 \cdot \cos^2\gamma}{3} + r \cdot L^2 \cdot \beta \cdot \cos^2\gamma - \right.$ $\left. 2 \cdot L \cdot r^2 \cos y \cos\beta + \frac{r^3\beta}{2} - \frac{r^3 \sin 2\beta}{4} \right\}$ $\varepsilon = My/EI = Mt/2EI$, where the moment $M = F \_ \cos Y + r \cdot \sin\beta$ then, $L.\cos y + 7".5i\eta\beta$ $i - = 3.3_F \cdot t$ $. \cos^3 Y + 61'. \cos^2 y. r - 121. \cos y, c\ osp.\ r'2 r^a$ As the straight section of the filter element is tangential with the initial radius, β=γ, then, $$\varepsilon = 3 \cdot \delta_F \cdot t \left[ \frac{L \cdot \cos\beta + r \cdot \sin\beta}{2L^3 \cdot \cos^2\beta + 6L^2 \cdot \cos^2\beta \cdot r - 12L \cdot \cos^2\beta \cdot r^2 + 2r^3 \cdot \beta - \frac{3r^3 \cdot \sin 2\beta}{2}} \right]$$

In this example, the relationship between filter element length and strain is more complicated with relations to the filter element arc angle β. These variables should be limited by balancing capture space (the volume of the capture cone increases with increasing filter element length) and parking space (parking space increases with increasing filter element length) while fine tweaking to reduce strain. Similarly to the prior art device, strain has a direct relationship with deflection and filter element thickness. Filter element strain reduces with decreasing filter element thickness; however, filter element thickness should be kept high enough to contribute sufficient radial force in order to prevent the device from migrating.

Unlike the prior art, deflection is determined by a combination of vessel size and shape setting position. By shape setting the filter elements to have their ends positioned approximately one quarter of the way between the filter's central axis and the vessel wall (when constrained in the upper vessel size limit without the use of a holder), the deflection is reduced by approximately 75% when compared to the prior art device. The filter element deflection will also be halved for the present invention when constrained in the lower vessel size although the bending direction will be reversed as the filter elements will press against each other rather than pull away from each other. The reduction in deflection will in turn reduce filter element strain significantly. A reduction in strain will significantly improve fatigue resistance in an environment where the filter experiences deflections at a rate of 70/min radially and 20/min longitudinally due to pulsatile blood flow and respiration respectively.

In a preferred embodiment, the device of the present invention is indicated across a vessel size range, ideally from 16 mm to 32 mm internal diameter, and the filter elements are shape set to curve radially inwardly to a point that is slightly offset from a position one quarter of the way between the central axis and the vessel wall if constrained in the upper vessel size when a holder is not in place. Considerations in this embodiment include effects of the filter element profile centroid and material properties.

Referring to FIGS. 10A and 10B, the image on the left (FIG. 10A) illustrates a typical cross section of the filter element if it is cut from tubular stock, the unbroken line depicting the filter element cross section, and the broken line depicting the tubular stock. The image to the right (FIG. 10B) depicts the filter element cross section with parametric designations. In order to determine the offset orientation, the centroid must be calculated to determine which bending direction will yield the highest strains. It is appreciated that the corners of the filter element profile may be rounded.

Distance of centroid from $O$=Moment of area about $y$ axis/area of the figure

Area=$r.dO.dr$,

Moment about $y$ axis=$r.dO.dr.r. \cos O = r^2 . \cos 9.dr.d9$

Then, casB $d0. dt\ 2(ri-r)$. ana $$\text{Moment of area} = \int_{-\alpha}^{\alpha} \int_{r_1}^{r_0} r^2 \cdot 3$$

$$\text{Area} = \int_{-\alpha}^{\alpha} \int_{r_1}^{r_0} r \cdot d\theta \cdot dr = (r_0^2 - r_i^2) \cdot \alpha$$

Distance C of centroid from O $$\frac{2\sin\alpha}{3\alpha} \cdot \frac{(r_0^2 - r_i^2)}{(r_0^2 - r_i^2)}$$

In order to determine which bending direction will yield the highest strains, the centroid can be compared to a theoretical position of equal strain. Referring to FIG. 11, the position of equal strain, "ES", is half way between the position closest to the centre O and the position farthest from centre O.

Then,

ES=$c+a/2r\ a$.

Ti, $a=D.\cos a$ $C\ O\ \sec a=r_0$–Ti. $\cos a$, $c=r$, $\cos a\ r_0+T_j.\cos a$

ES=

The arc angle of a single filter element=$2a$. The present invention may comprise one or more filter element(s) and one or more connector strut(s) with a proximal and distal support hoop. The minimum number of proximal and distal peaks of the proximal and distal support hoops required to manufacture the filter is 2, due to geometry constraints. The maximum number of proximal and/or distal peaks required is 12; more than this will reduce the radial force and increase delivery profile beyond acceptable limits. Then, $2a$ should not exceed 60° where a filter is supplied comprising 2 proximal and distal peaks, 2 connector struts, and 4 filter elements as the number of struts to be cut radially from the tube will be 6. The angle $2a$ will reduce as connector and/or filter element numbers increase. Therefore, ES can be compared to the distance from the centroid to point O for $2a \leq 60°$. More preferably, the filter comprises an array of 6 to 12 filter elements with 4 to 8 connector struts. Then, $2a$ will be <36°. It is appreciated that the actual angle may be smaller as the cutting process will reduce the available degrees from the tubing. In addition, the connector elements may have wider strut widths than the filter elements in order to balance the support frame stiffness relative to the filter elements. This would also reduce $2a$.

In order to provide a filter with a low delivery profile, the raw tubing outer diameter should not exceed 8 mm and to provide sufficient radial force and structural support, the OD should not be lower than 1.5 mm. The wall thickness of the tube contributes towards strut stiffness and to satisfy radial force and structural support requirements, the wall thickness should be greater than 0.15 mm. The wall thickness should not exceed 0.8 mm as this would increase radial force and/or delivery profile beyond acceptable limits. Then, the raw tubing O.D. should range from 1.5 mm to 8.0 mm with a wall thickness ranging from 0.15 mm to 0.8 mm. More preferably, the raw tubing O.D. should range from 2 mm to 6.0 mm with a wall thickness ranging from 0.25 mm to 0.45 mm.

Therefore, preferred limitations are:
$r_0$ ranges from 1.5 to 8.0 mm
wall thickness ranges from 0.15 to 0.60 mm $2a \leq 60°$ ES≤Centroid and (Centroid−ES) increases with increasing $2a$. Then, filter element strain will be higher in compression when bending towards the centre O than that for a filter element bending away from the centre O. Similarly, filter element strain will be higher in tension when bending away from the centre O than that for a filter element bending towards the centre O. A method of reducing tensile or compressive strain is to reduce the deflection in a particular bending direction.

Surface cracks that may be present are more likely to propagate under cyclic tensile strains than cyclic compressive strains. Then, it is more desirable to balance tensile strains across the indicated vessel size range. Further, NiTi is stronger in compression than in tension. Then, it is preferred that the filter element be positioned in a way that reduces tensile strains to improve fatigue resistance.

Considering a filter device indicated for a vessel size range from 16 to 32 mm, the filter elements will have equal tensile strain in the upper and lower vessel sizes if the filter element ends are positioned at a point radially outwardly of a quarter way position between the central axis and the support frame when constrained in the upper (largest indicated) vessel size (due to ES≤C). With reducing $2a$, the filter element ends offset position radially outwardly of the quarter way position also reduces. Similarly, the filter element ends will form a central apex when positioned in a vessel that is smaller than the middle vessel (24 mm) of the 16-32 mm vessel size range. In general, the filter elements have positions when unconnected such hat, the filter element ends are located between the support frame and the central axis when the vascular filter device is unconstrained.

While the extent of the distance from the central axis is stated above as being preferably one quarter (25%) of the distance from the central axis to the support (radius), it could be in the range of 10% to 50% of this distance and more preferably in the range of 15% to 40%. Also, this is the preferred filter end position when the device is constrained in a vessel in the top third of the indicated size range the filter element end. When the device is constrained in a vessel at approximately the middle of the indicated size range (about 22 mm to 26 mm for the above indicated size range) the filter elements are within +/−10% of the radius from the central axis.

When the device is constrained in a vessel of the lower third of the indicated size range (about 16 mm to 22 mm for the above indicated size range) the filter elements are within about 15% to 40%) of the radius from the central axis, on the opposed side (see FIG. 6(b)).

It is appreciated that the filter element may have single straight struts, single curved struts, or a combination of both. A preferred filter element is of a V-shaped construction with a straight and/or curved profile (refer to FIG. 7).

Shape set filter elements may also be supplied with a support frame consisting of a proximal support hoop alone or with any other support frame design.

The shape set filter arms form an apex without the use of a holder when constrained in a tube with an internal diameter radially outwardly of the middle (24 mm) of the vessel size range (16 to 32 mm).

The filter elements and the support may be heat set in a tubular shape in order to achieve minimum filter element strain in the crimped delivery configuration.

The filter device may be formed to have a diameter that is larger than the upper vessel size in order to afford sufficient radial force to the device. For instance, with an indicated vessel size range of 16 to 32 mm, the unconstrained diameter may be 36 mm, or more preferably, 34 mm. The balance of filter element deflection should take into account the upper (32 mm) and lower (16 mm) vessel sizes and not the unconstrained vessel size. It is appreciated that a narrower or broader vessel size range may be chosen. A preferred vessel size range is 16 to 28 mm. Depending on support frame design, the connection between the filter elements and support frame may be positioned up to 2 mm radially inwardly of the average vessel size. Offsets such as these should be accounted for when balancing strain across the indicated vessel size range. Similarly, the support frame may taper, curve, flare, or undulate from the proximal to distal end. Again, when balancing the strain across the indicated vessel size range, the distance between the filter element connection to the central axis in the upper and lower vessel sizes should be taken as the filter element deflection range.

Any of a variety of means may be employed to secure the filter elements together at their ends to form the apex including holders disclosed in WO2010/082187. The following are further embodiments that can be used. Where shape set filter arms curve radially inwardly, the holder should be manufactured of a biostable material.

FIGS. 12A and 12B, crimped together inside a tube 10.

FIGS. 13A and 13B, crimped within the tube 10 against an axial pin 11.

FIGS. 14A and 14B, crimped as in FIGS. 13A and 13B, except in this case the pin has a head 13 to aid positioning of the pin during manufacturing.

FIG. 15, a tube 15 has an array of slots for each or a group of filter elements. The tube is crimped onto the filter elements from the ID to the OD of the tube. Alternatively, the filter elements can be placed in an array of slots in a tube or rod and be coupled to the tube or rod by welding, snap fitting, or by bending at least one of the capture arms distal to the apex to prevent the coupling tube or rod from dislodging. Adhesives may also be used to fix the apex in place.

FIGS. 16A-16F, a coupler 20 having an annular socket 21 may be used to receive and, crimp the filter element ends. The coupler may be open at both ends, as shown in the coupler 25 of this drawing.

FIG. 17, the filter elements may be twisted together or tied together in a "Teepee" arrangement.

FIGS. 18A-18E and 19A-19E, the filter elements have interlocking features to hold them together at the filter apex. The interlocking features may be machined, bonded, or otherwise attached. FIG. 18 shows filter elements 35 with grooves 36 on one side and inter-engaging ridges 37 on the opposed side. FIG. 19 shows filter elements 50 with opposed dovetail features 51 and 52, elements 55 with only male dovetail ridges and elements 60 with only female dovetail slots, with the elements 55 and 60 interconnecting as illustrated in FIGS. 10A and 10B. Alternatively, snap fit features may be used to interlock the filter element ends.

The designs shown in FIGS. 12A-12B, 13A-13B, and 14A-14B, and the top of FIG. 16 (FIGS. 16A-16C) offer streamlined profiles when compared to pins and ties as they are concentric with the apex and can be kept to a low profile (small diameter). FIG. 15 and the bottom of FIG. 16 (FIGS. 16D-16F) offer similar advantages while also facilitating blood flow through a central axis in order to minimise stagnant areas.

The interlocking features of FIGS. 18A-18E and 19A-19E offer a more streamlined profile by providing minimal material at the apex and facilitating blood flow through a central lumen.

A streamlined profile will reduce irregular flow patterns and shear blood flow forces to in turn reduce fibrin and/or clot formation.

These principles are also applicable to a filter where the ends of the filter elements are integral. An integral filter element end presents an additional challenge in that one cannot heat set the filter element ends to be positioned approximately one quarter way between the central axis and the vessel wall in the maximum indicated vessel size as the ends of the filter elements are not free—they are connected integrally. For such cases, it is possible to heat set the support frame separately to the filter portion thereby allowing the support frame to be biased to an unconstrained diameter of 34 mm (affording additional radial force for placement in a max indicated vessel size of 32 mm) and the filter elements can be biased to have similar strain when constrained in the minimum and maximum indicated vessel sizes. This could be achieved by heat setting the complete implant for an unconstrained diameter of 34 mm and then insulating the support portion while heat setting the filter portion when constrained in a vessel approximately in the middle of the vessel size range. Alternatively, this could be achieved in reverse where the implant is heat set in a vessel approximately in the middle of the vessel size range and then insulating the filter portion while heat setting the frame to have an unconstrained diameter of 34 mm. Integral Apex In some embodiments a vascular filter device has a support structure which is preferably stent-like in overall configuration, and preferably has proximal and distal hoops linked by connecting struts. The device preferably has a filter with filter elements connected to the support at one end and converging at the other end. In some embodiments they converge at an apex. The area of convergence is integral with at least some of the filter elements.

For example, the apex may be integral with the filter elements alone, with the filter elements and a portion of the support frame, or with a portion of the filter elements. This is advantageous for fatigue and manufacturing efficiency. The apex is the same diameter as the laser cut tube that the support frame and filter elements are cut from before expansion to the desired in-use diameter. However, it introduces a challenge in keeping a distal crown arrangement as the connector struts inherently split the integral filter apex into six separate filter element ends. The embodiments provide means to include a proximal and distal crown with an integral filter apex where the filter is cut from the raw tube in multiple pieces.

The filter is cut from the raw tube in two pieces, proximal and distal, preferably from the same tubing stock. This is shown in FIG. 20 in which a device 201 has separate proximal and distal parts 202 and 203 cut from the same tube. The proximal section (single piece cut from raw tubing) includes a proximal support hoop, capture arms, integral apex, and a proximal portion of the straight connectors. The distal section (single piece cut from raw tubing) includes a distal portion of the straight connectors and the distal support hoop.

FIGS. 21A-21C and 22A-22E show the device in more detail. The proximal part 202 has proximal peaks 205 of a proximal support hoop, distal peaks 206 of this hoop, filter elements 207 (or "capture arms"), proximal connector struts 208, a cylindrical filter apex 209 which is integral with the filter elements. The distal part 203 has connectors 210, hoop proximal peaks 211, and distal peaks 212

Once laser cut, the proximal and distal pieces are expanded to increase the filter diameter, as shown in FIGS. 23A and 23B, and and 24A-24D. For delivery, the expanded filter is crimped to a diameter closer to the raw tubing diameter in order to transfer it into a catheter for low profile delivery. Once expanded, the distal and proximal pieces are connected together via welding or mechanical means as shown in FIGS. 25A-25C.

The proximal and distal pieces may alternatively be connected together before expansion. In summary, the proximal piece 202 includes a proximal crown 205, 206, an array of filter elements 207 and an array of connecting struts 208. The distal piece 203 includes a distal crown 211, 212 and an array of connecting struts 210. The filter is joined by coupling the connecting struts 208 and 210 from both proximal and distal pieces. The coupling methods may include but are not limited to welding, crimping, swaging, adhesive bond, and/or snap fitting. The connection between proximal and distal may be provided at any point along the connector struts proximal to the position of the filter apex. The connector strut is advantageous for coupling the two pieces as it is a low strain region and will not impact fatigue performance significantly.

A developed view of the tubular laser cut pattern (tubular view shown in FIGS. 20 to 22) for the proximal and distal halves is shown in FIGS. 26A and 26B to illustrate how the connector struts cannot extend past the integral apex. A developed view is an image of the tubular pattern rolled out flat. The drawing to the left depicts the proximal support hoop, proximal half of the connector struts, the filter elements and the integral apex while the drawing to the right depicts the distal half of the connector struts and the distal support hoop. If the developed view is rolled so that the top and bottom are joined, it depicts the tubular laser cutting pattern used to machine the parts from a raw tube. The laser cut tube is then expanded to form the filter and heat set to remember its new shape. This is done by expanding the laser cut tube into its new shape and constraining in a fixture or on a mandrel and then performing a heat treatment. The filter can then be crimped down to a diameter that is greater than, equal to, or less than that of the raw tube and loaded into a delivery sheath for low profile delivery to the implant site. When deployed into an environment that is above the Af temperature, the filter will revert to it's expanded form provided by the shape setting step (for example, if the materials Af temperature is 20 degrees Celsius, it will revert to its shape set form in an environment that is above 20 degrees Celsius such as that of blood at 37 degrees Celsius. This step will reduce strains in the device when deployed in a vessel. Alternatively, the device may be manufactured from materials with no shape memory properties such as spring steel or cobalt chromium in which case the device may be annealed to remove the stresses raised through work hardening. As the integral apex is a tube that lies between the proximal and distal support hoops, it is not possible to include connector struts that extend between the proximal and distal support hoops as they would inherently separate the integral apex into non-integrated apices. This is overcome by cutting proximal and distal segments separately and joining them afterwards. Referring to FIGS. 27A-27F, the integral filter apex 209 has a smooth profile that reduces disruption to blood flow and thus reduces thrombus formation by reducing stagnation and irregular blood flow patterns. Coupling means such as pins and ties can add complexity that may cause irregular blood flow patterns and/or stagnation leading to thrombus formation.

Referring to FIGS. 28A-28F, alternatively, the connection point may be provided at the proximal end of the filter elements. This device has a proximal part 250 with a proximal hoop and a filter, and a distal part 255 with struts 256 and a hoop 257. Referring to FIGS. 28E-28H, in another embodiment, the array of filter elements 260 is provided separately to an integral support frame 261.

Further advantages of the separate filter portion is the ability to provide a permanent filter or a permanent filter with the option to retrieve the filter portion should the need arise, leaving the support frame behind. Refer to FIGS. 29A to 31F. For an optional filter with a separate support frame, it is advantageous to provide a connection between the support frame and filter that is low profile and streamlined so that during retrieval, minimal trauma is caused to any neo-intimal. A preferred solution comprises a filter portion with an array of pin shaped proximal ends. During retrieval, the apex of the filter is engaged from a jugular approach and pulled cranially into a sheath to slide the pin shaped proximal filter element ends through endothelial growth. The attachment means between the filter and support frame may include a bond, interference fit, breakable component, crimped component, heat shrink, magnet, tie or other mechanism that requires a predefined force to release the filter—this will ensure the filter is not released inadvertently if the release force was too low and will prevent damage to the vessel wall if the release force was too high. Ideally, the release force would range between 3N and 15N, more preferably between 5N and 10N.

FIGS. 29A-29D show a support 280 and FIGS. 29E-29H show a separate filter 290, and FIG. 30 shows the completed device after interconnection.

Referring to FIGS. 31A-31F, these show how the supports 280 and 290 are interconnected within a sleeve 310. The distal crown may be provided as a single piece given that the filter elements are longer than the connector elements from the point where the filter elements meet the connector elements. This is advantageous because a shorter filter can be manufactured. A shorter filter can also be achieved with short connector elements on both proximal and distal pieces. This is shown in FIGS. 32A-32D, in which a proximal part 350 connects with a distal part 360 comprising only a hoop.

Alternatively, the connection point may be provided along the filter elements as this too is a low strain region. FIGS. 33-33D such a first part 400 and second part 410. Welds used to join the laser cut parts may include but are not limited to the weld types (welds depicted as filled in areas) shown in FIGS. 34A-34L. These include butt and overlap joints, some with profiling ends.

Dovetail like features may be used to interlock struts. These features may be combined with welding, adhesive bonds, and/or crimping, as shown FIGS. 35A and 35B.

Figure 36:
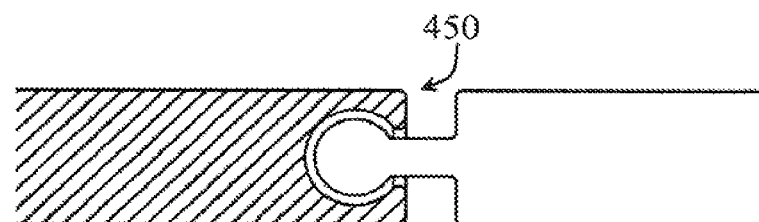
Figure 37:
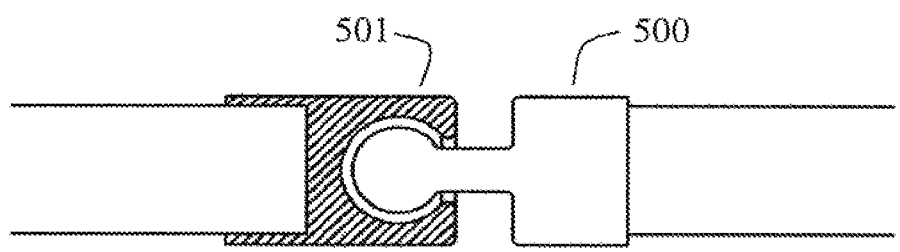
Figure 38A:
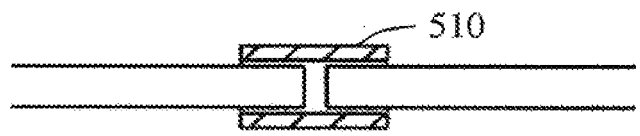
Figure 38B:
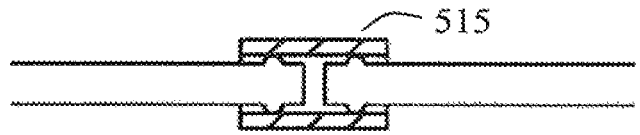
Figure 38C:
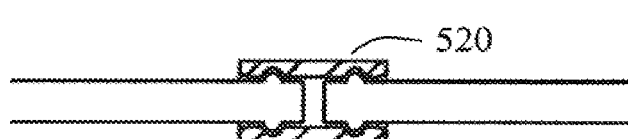

A ball and socket joint 450 could be formed on the connectors to provide a flexible connection (FIG. 36). The ball and socket features could be manufactured separately and attached as parts 500 and 501 in FIG. 37. Any form of hinge may be used to increase flexibility of the attachment.

Figure 39A:
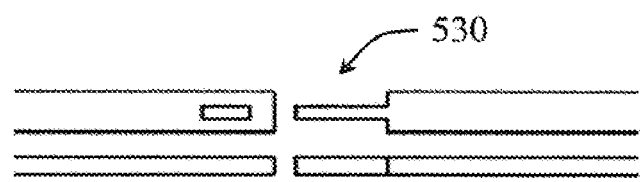
Figure 39B:
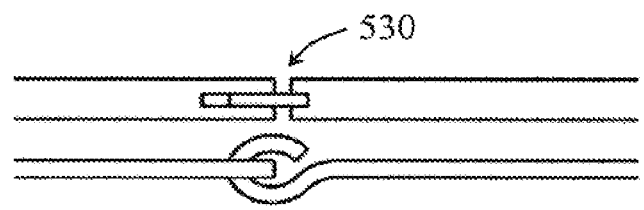

Crimping tubes 510, 515, and 520 may be used to join struts. Ridge or recess features may be provided on the struts, crimping tube, or both to increase the strength of the joint (FIGS. 38A-38C) Struts 530 may be machined to provide a slot and tie arrangement. The tie may be formed into a hook shape through mechanical or heat setting methods (FIGS. 39A and 39B).

Figure 40A:
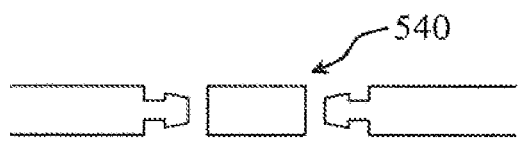
Figure 40B:
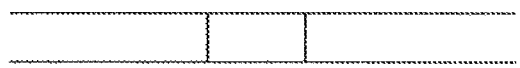

Snap fit features 540 may be laser cut on the connector struts to lock into an array of snap fit receptors (FIGS. 40A and 40B). The snap fit receptors may be biodegradable so that they separate after a predetermined period of time.

Figure 41:
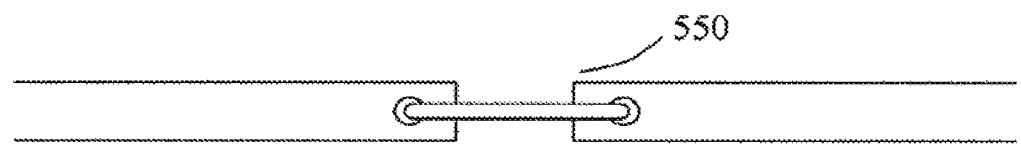

A biostable thread or biodegradable filament 550 may also be used to attach proximal and distal connector struts (FIG. 41). Each connector strut may have an opening or feature that the thread or biodegradable filament can be threaded through. When a filter with an integral apex is crimped for the delivery configuration, the delivery profile is governed by the wall thickness of the connector struts and the OD of the filter apex. The apex may be formed to provide a recess for each connector strut. This may be achieved by crimping the filter apex or by machining the filter apex. This is shown in an apex arrangement 560 in FIG. 42.

The proximal and distal connector struts connected by a thread or biodegradable filament may be spaced apart so that the apex lies between them when in the delivery configuration.

The raw tube, from which the proximal filter portion is cut, may be formed to have a necked down region 570 at the distal end to provide an integrated apex with a smaller OD than that of the proximal and distal support crowns (FIG. 43). In another embodiment the apex may be connected to a distal support, FIGS. 44A-44C. The filter comprises a proximal support crown 600 with an array of short connector elements 601 extending from each distal peak of the proximal crown. Two curved filter elements (possible to include 1, 2, 3, or more filter elements) extend from the distal end of each connector strut 401 to an integral tubular shaped filter apex 602. Two distal support struts extend distally from the filter apex to a distal support crown. It is possible to include 1, 2, 3, or more distal support struts. Fewer distal supports are preferred in order to minimise disruption to the blood flow. However, a balance is required between stability and flow obstruction where an increase in number of distal support struts enhances stability. As shown in the device 620 of FIGS. 45A and 45B, it is possible to enhance vessel contact by extending the connector struts distally to a point proximal of the filter apex. Additional distal connector struts may extend proximally from the proximal peaks of the distal support crown.

Further modifications can be made to include V-shaped support elements 625 extending proximally along the vessel wall from the distal crown and/or distally from the proximal crown (FIGS. 46A-46D).

An integral filter apex 630 (FIGS. 47A and 47B) provides flexibility between the proximal and distal support crowns. Referring to FIGS. 48A-48E, a C-shaped integral filter apex is provided where one (or more) connector element(s) 651 in a device 650 is cut through a fully integral tubular filter apex to form a C-shaped filter apex 651. This allows for an integral filter device with a proximal support crown, a distal support crown, a connector strut connecting the proximal and distal support crowns and a filter portion connected to the support frame between the proximal and distal support crowns.

As shown in FIGS. 49A-49D, vessel wall contact can be enhanced by extending struts 670 distally from the proximal support crown and/or by extending struts or v-shaped elements proximally from the distal support crown.

The C-shape integral filter apex can be modified to cut two or more connector struts 680, 681 provided means are provided to join the filter apex. Where two connector struts are cut, the filter apex can be joined simply with a pin, ring or weld. FIGS. 50A and 50C show elevation views of the filter with two connector struts.

Figure 51A:
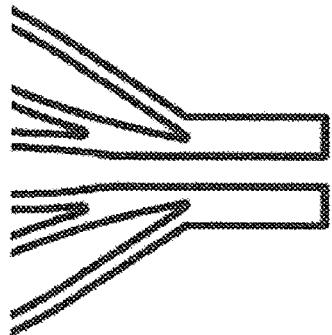
Figure 51B:
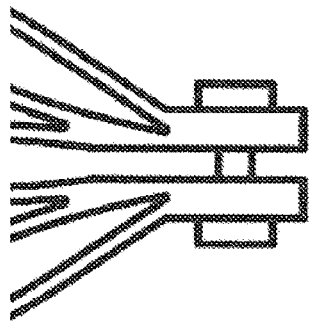
Figure 51C:
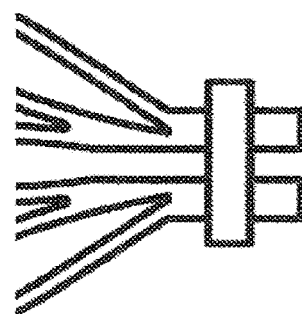
Figure 52A:
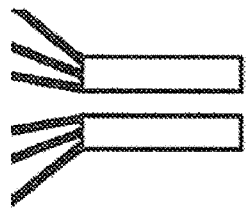
Figure 52B:
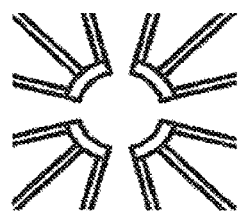
Figure 52C:
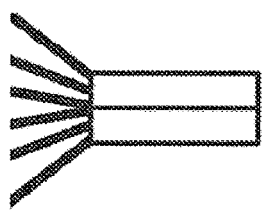
Figure 52D:
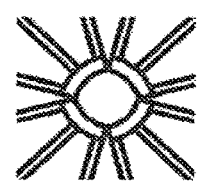
Figure 53A:
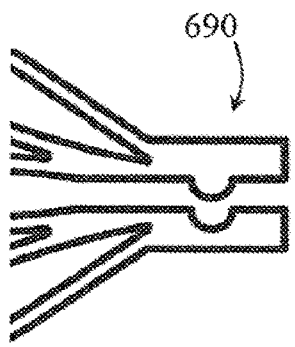
Figure 53B:
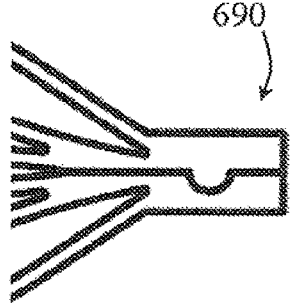
Figure 53C:
Figure 54A:
Figure 54B:
Figure 54C:
Figure 54D:
Figure 55A:
Figure 55B:
Figure 55C:
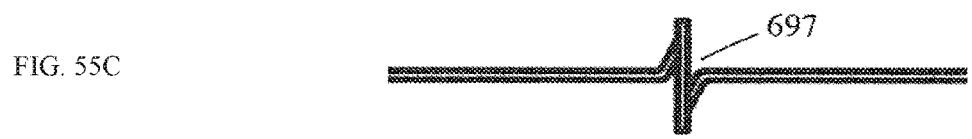

The C-shape integrated apex with two connector struts cut from it at 180 degrees to each other may not require fastening to form the filter shape as the 6 filter struts connected to each half would provide sufficient force to prevent the apex from moving significantly radially upon impact of a blood clot or through movement of the vasculature. However, the two piece apex can be joined using fasteners such as a pin, ring, crimping methods, swaging, or weld. This is shown in FIGS. 51A-51C. Alternatively, magnets could be supplied on each half to keep them together.

Referring to FIGS. 52A-52D, inclusion of 4 connector struts with a C-shape integrated apex yields 4 separated apex portions, that when assembled together; provide a smaller apex tube OD than the original cut tube OD. This is advantageous to achieve a low profile in the crimped delivery configuration. When crimped, the connector struts must lie across the OD of the apex, thereby, increasing the overall OD of the apex. A reduced apex OD will in turn allow the crimped delivery configuration to have a lower profile. Once assembled the 4 apex portions can be coupled using a variety of methods including but not limited to welding, low profile ties, caps, pins, magnetism, and rings. It is appreciated that some of these coupling means may increase the OD of the apex, however, welds could be applied in and/or outside the tubular apex and be ground down to remove excess material. Pins could be positioned so that the pin heads are misaligned with the connector struts and caps or rings could be profiled to provide a reception space for the connector struts.

Mating features 690 (FIGS. 53A-53C) can be included to enhance the different coupling means while simultaneously imparting flexibility in the connector struts to allow for more conform ability of the implant in the vessel (i.e. for curved vena cavae). The top left and right images show the filter apex before and after assembly respectively and the bottom image shows the connector strut. Referring to FIGS. 54A-54D to 55A-55C, it is possible to machine and/or shape flexible features for the connector struts, such as a sine wave 691, an offset sine wave 692, M-shaped 693, W-shaped 694, nested 695, elongated 696, or coil-shaped articulations 697.

Figure 56A:
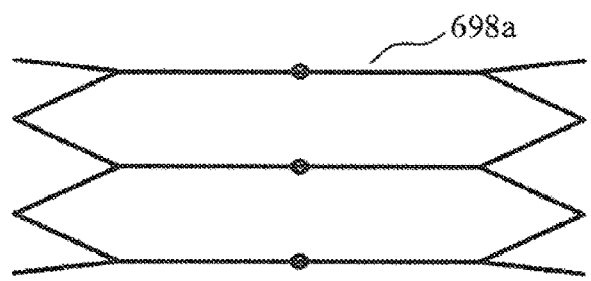
Figure 56B:
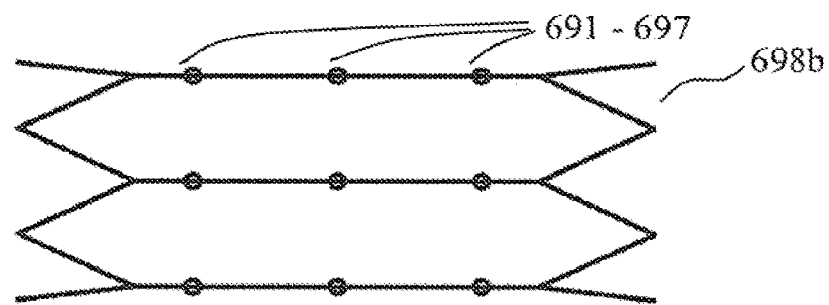

It is also possible to provide flexible features in different configurations over the length of the filter. They may be placed on the centre of each connector strut (698*a*, FIG. 56A), or a number of articulations 698*b* placed on each connector strut (FIG. 56B). The articulations may be equally distributed along the length of the connector or grouped together.

Figure 57A:
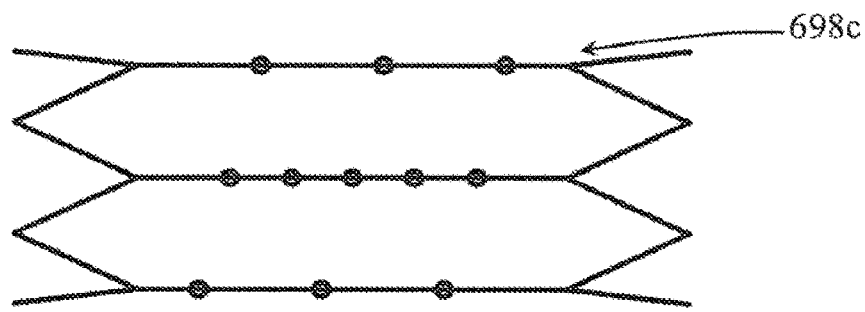
Figure 57B:
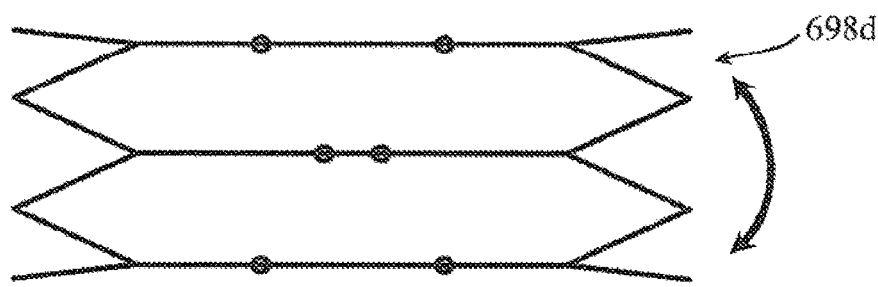
Figure 57C:
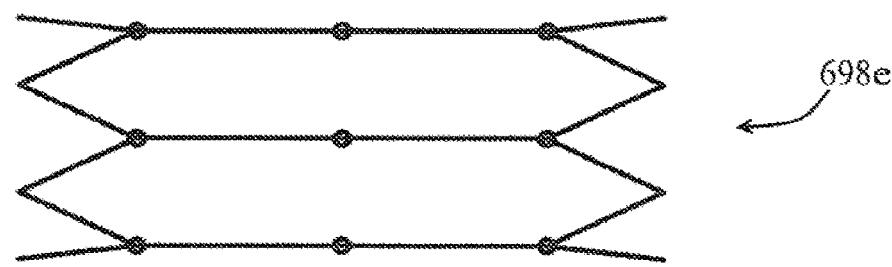
Figures 58A, 58B, 58C, 58D:
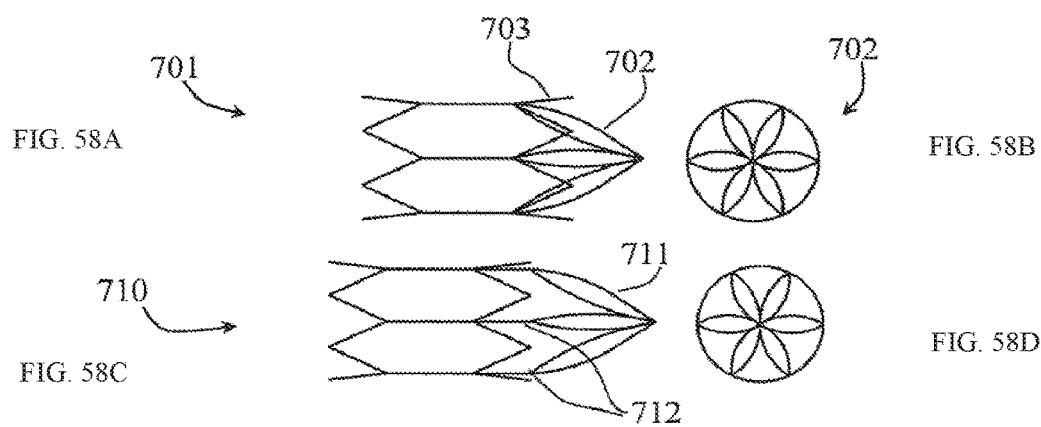

Further articulation embodiments are as follows, with reference to FIGS. 57A-57C:

698*c*, Spiral pattern of articulations to produce a spring-like flexibility in the frame,

698*d*, X-shaped distribution to allow greater bending in the plane shown, or

698*e*, Articulations may also be provided at joints to crowns.

Integral Filter Device

In some embodiments, a filter apex is integral with the filter elements that are in turn integral with a longitudinal support structure. The longitudinal support structure eliminates tilting once sufficient length is afforded to it, for example, if the device length is a multiple of the diameter of the vena cava in which it is implanted. A balance between implant length and tilting must be provided to ensure that implant length is kept to a minimum. When deployed in the filters maximum indicated vessel size, the ratio of filter length to vessel diameter should range from 1:1 to 2.3:1. More preferably, the ratio of filter length to vessel diameter should range from 1.5:1 to 2:1. The longitudinal support is designed to press against the vessel wall with sufficient radial force to prevent migration in the vessel. The support may also be fitted with barbs or protrusions to aid in anchoring it to the vessel wall. The filter elements connect to the apex in a way that minimises obstruction to the blood flow, for instance, it is preferred that two or more filter elements merge into one filter element in close proximity to the apex in order to provide a streamlined connection (refer to FIGS. 62A-62C). The proximity of the merging point to the apex should range from 1 to 10 mm; a range of 3 to 6 mm is preferred.

Referring to FIGS. 58A-58D, a filter device 701 has a filter 702 which is connected at the distal end of the device 701 to a distal support hoop 703. Because the filter 702 extends from one end of the support it may be integrally manufactured from a tube by laser cutting in one piece. The filter elements may be attached to the hoop (703, FIG. 58A) or to extended connector elements (712, FIG. 58C). Alternatively, the plurality of connector elements may extend from the struts or distal peaks of the distal support hoop.

Figures 59A, 59B, 59C, 59D:
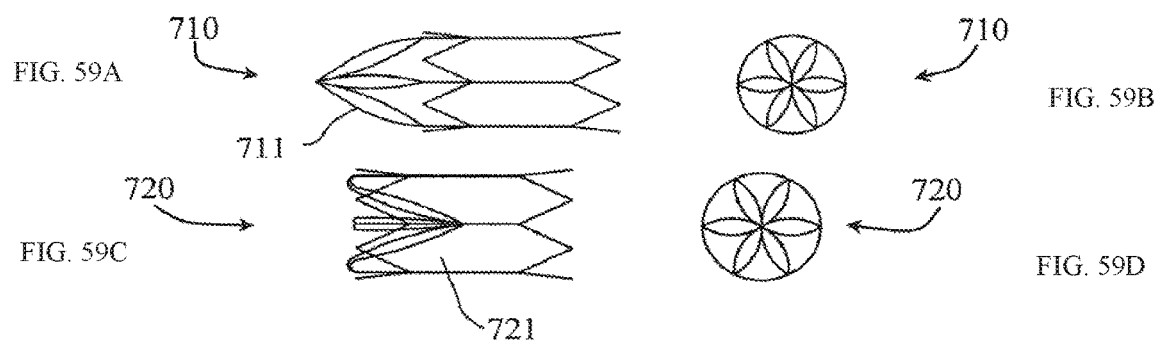
Figures 60A, 60B, 60C, 60D:
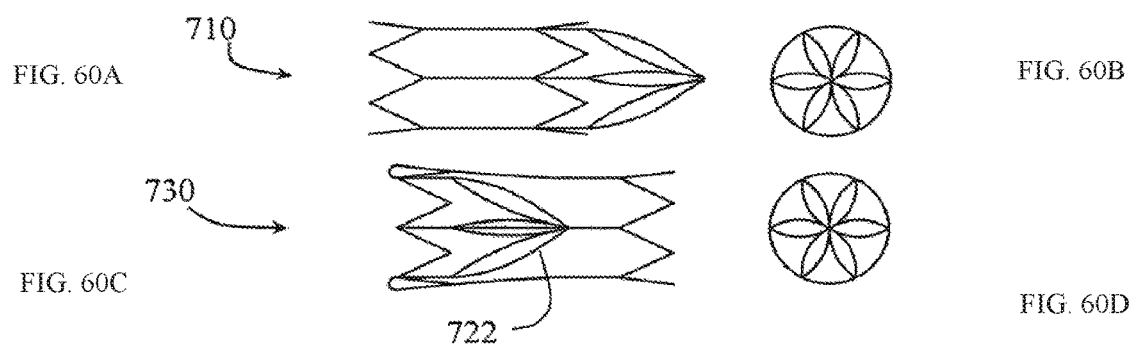

FIG. 59 shows on top (FIGS. 59A and 59B) the filter device 710 oriented in the opposite direction. This device may be improved by inverting the filter to point into the space encompassed by the support, as shown by a filter 721 in a device 720 in the bottom of FIG. 59 (FIGS. 59C and 59D). The filter may be connected to the proximal support hoop or proximal to the proximal support hoop with the addition of proximal connecting struts. The device is cut from a tube and expanded with the apex facing proximally. In order to keep captured clots central in the blood flow, the filter apex is directed distally through inversion of the filter inside the tubular support structure. Heat setting techniques may be employed to reduce the risk of the filter righting itself back outside of the tubular support. The filter's inner shape may change from a concave parabola to a convex parabola or intermediate configurations.

Referring to FIGS. 60A-60D, alternatively, the tubular support structure can be inverted over the filter cone to change a device 710 to a device 730 as illustrated. This approach keeps the filter cone shape as a concave parabola.

Referring to FIGS. 61A-61D a device 760 has a proximal hoop 761, connector struts 762, a filter 766 and a distal support hoop 763. The distal support hoop 763 comprises an array of V-shaped distal supports 766 and extension struts 764 in which the array of extension struts are connected to the connector struts. Alternatively, the extension struts may be omitted if the array of v-shaped distal supports is connected to the connector struts. Elevation and end views are shown at the top of FIG. 61 (FIGS. 61A and 61B) with a plan view in the middle and a projected view below. The filter elements 765 extend to a central apex at a point distal to the distal peak of the distal hoop when in the laser cut unexpanded state during manufacturing. Each distal support hoop comprises extension support struts 64 that extend beyond the point of connection between the filter elements and the support structure. The extensions are connected to an array of v-shaped struts 766 that provide a radial force to keep them pressed against the vessel wall. The device has two extension struts 764 for every proximal connector strut. A disadvantage of the distal filter 701 and 710 is that it adds length to the device for a given tubular length (ie length from proximal peak of proximal hoop to distal peak of distal hoop). The integral filter design of device 760 is advantageous as it allows for a shorter filter length and thus improved implant length with a reduced length of vena cava required as a suitable location for implanting the device. The filter apex may move closer to or inside the tubular support structure when it is deployed in a vessel due to foreshortening upon expansion. Foreshortening is the reduction in length of an expandable device as it moves from a compacted delivery configuration to an expanded configuration in use. As the device expands, the v-shaped supports, that afford radial force to the device, move from an acute v-shape in the compacted delivery configuration to an obtuse v-shape in the expanded configuration during use. The more obtuse the v-shape for a given strut length, the greater the reduction in axial length. Two or more filter elements may merge into one filter element in close proximity to the apex in order to provide a more streamlined profile to minimise obstruction to the blood flow. This will reduce irregular flow patterns and shear blood flow forces to in turn reduce fibrin and/or clot formation. Refer to FIGS. 62A-62C illustrating the y-shaped filter elements 766 and apex 767.

A developed pattern is shown in FIG. 63 that could be used to laser cut the device from tubing stock. If the developed view is rolled so that the top and bottom are joined, it depicts the tubular laser cutting pattern used to machine the parts from a raw tube. The laser cut tube is then expanded to form the filter. If the filter is made from Nitinol or a similar material with shape memory properties, the expanded filter can be heat set to remember its new shape. This is done by expanding the laser cut tube into its new shape and constraining it in a fixture or on a mandrel and then performing a heat treatment. The filter can then be crimped down to a diameter that is greater than, equal to, or less than that of the raw tube and loaded into a delivery sheath for low profile delivery to the implant site. When deployed into an environment that is above the Af temperature, the filter will revert to it's expanded form provided by the shape setting step. For example, if the materials Af temperature is 20 degrees Celsius, it will revert to its shape set form in an environment that is above 20 degrees Celsius such as that of blood at 37 degrees Celsius. Alternatively, if the device is formed from other materials with no shape setting properties such as spring steel or cobalt chromium, the expanded device may be annealed to remove the stresses raised through work hardening. It is also possible to connect the extension support struts and/or filter elements to the proximal support hoop.

Referring to FIGS. 64A-64B a device 780 has a proximal hoop 781, connector struts 782, a distal hoop array 783, and a filter 785. In this arrangement the filter has been shortened by adjusting the proximal connector and/or extension support strut length. The distal hoop array can also be flared to aid vessel wall apposition, deployment accuracy, and resistance to migration. A distal flare is a section at the distal end where the cylindrical profile tapers outwardly to form a larger diameter than the cylindrical profile, refer to FIGS. 64A-64B. Similarly, the proximal hoop may also be flared to further assist vessel wall apposition, deployment accuracy, and resistance to migration. In another embodiment, the proximal and/or distal hoop flares may extend across the proximal connector struts and/or extension struts. The support structure should be at least as long as the diameter of the largest indicated vessel diameter, preferably, the ratio of the support structure length to the diameter of the largest indicated vessel should be in the range of 1:1 to 2.3:1, more preferably 1.5:1 to 2:1, in order to prevent tilting. In the case of the short filter with equal length and diameter, the flared distal support array will aid tilt prevention.

Referring to FIGS. 65A-65B the extension struts may be connected to the proximal hoop, the proximal connector struts, or the filter elements. The filter elements may be connected to extended connector struts, extension struts, the proximal hoop, or the connector struts. It is also possible to omit the proximal connector struts by connecting the filter elements or extension struts to the proximal hoop. An extended connector strut may also be provided; this would reduce the number of filter element connections at the vessel wall as the extended proximal connector strut would bend radially inwards to a point away from the vessel wall before splitting into two or more filter elements. Less filter element connections at the vessel wall will provide a more streamlined profile to minimise areas of stagnation, reduce irregular flow patterns and shear blood flow forces to in turn reduce fibrin and/or clot formation. Alternatively, one filter element may be provided for every proximal connector strut or one filter element may be provided for every second proximal connector strut. Referring to FIG. 66 in a device 810 an integral filter apex 815 can be positioned proximal to the distal peak of the distal support hoop 813 provided that the position of the apex 815 is positioned close to the distal tip of distal support hoop. This is possible as the axial length of the filter elements 816 reduces relative to the axial length of the device when the support structure 811, 812, 813, 814 is expanded from a laser cut tube (i.e. axial length of filter elements is less than filter element length in the expanded configuration). This is due to the change in axial length of the filter element when moving from an unexpanded state to an expanded state. FIG. 67 shows an expanded view of such a device on top (FIG. 67A) with two unexpanded developed views below (FIGS. 67B and 67C). The device comprises a proximal support hoop 811 and an array of proximal connector struts 812, extension struts 814, distal v-shaped supports 813, filter elements 816, and an integral filter apex 815. The apex 815, being in close position to the distal tip of the distal array of v-shaped supports 813 when in the unexpanded position, moves to a point just proximal of the distal tip of the distal array of v-shaped supports 813. The broken lines depict the change in length of the filter element when moving from an unexpanded position to an expanded position.

Referring to FIG. 68, alternatively, filter elements 820 can be formed or heat set to have a reduced length in the expanded state than their length in the laser cut tube pre expansion. The top image depicts the filter element pre forming while the bottom image depicts the filter element shape set to have a reduced length. The reduced filter element length will position the filter apex more proximally inside the tubular support frame. The example shown includes a wave pattern with reducing amplitude from the proximal (left) end to the distal (right) end. This has an additional advantage in that it will improve capture efficiency closer to the vessel wall where the plurality of filter elements are spaced wider apart than at the apex where the plurality of filter elements merge together. It is appreciated that any shape apart from straight will reduce filter element length. Referring to FIGS. 69A and 69B, it is also possible before expansion, to laser cut the connector struts 825 with a lengthening pattern. Also shown are the struts 826 of the proximal support hoop, extension struts 827 and filter elements 828. Then, the connector struts can be pulled axially between the proximal and distal ends to lengthen them before heat setting. This will have the effect of positioning the filter apex more proximally inside the tubular support frame.

Referring to FIGS. 70A and 70B there is a device 830 with a proximal hoop 831, mirrored V-shaped struts 832, a distal hoop array 833, filter elements 834, and an integral filter apex 835. The distal hoop has an array of V-shaped segments 837 connected to the proximal support hoop through connector struts 836. The number of peaks for the distal hoop array 833 can vary from 3 to 15 depending on the radial force required. The example 830 has a proximal support hoop with 12 proximal peaks where every second V-shaped segment has a mirrored V-shape segment extending distally. The mirrored V-shaped segment may be connected directly to the proximal support hoop or along the connector struts 836 of the distal support hoop. Singular filter elements extend distally from the distal peak of the mirrored v-shaped segments to provide 6 filter elements in total. Where fewer peaks are utilised, it is possible to increase the number of filter elements extending from the mirrored V-shaped segments either singularly or in groups. The filter elements can be shaped to provide uniform filtration pores. An integral filter apex 835 is provided by alternating between v-shaped struts 832 and v-shaped struts 837. This feature provides the distal hoop array and allows the filter elements 834 to extend past the distal peak of the distal hoop array 833. The filter elements meet the integral apex at a point just distal of the distal peaks of the disconnected distal support hoop when in the laser cut unexpanded state during manufacturing. The integral filter apex may move to a point proximal of the distal peak of the distal hoop array when in the expanded state in use. The integral apex may be provided more distally to the distal peaks of the distal hoop array in order to provide a filter that extends past the distal peaks of the distal support. This may be advantageous if the filter was deployed so that the renal veins flow across the filter unobstructed by the support structure. The additional flow inlets at the renal veins would enhance lysis of any clot that was captured. Refer to FIG. 77 that shows the position of the renal veins.

Referring to FIGS. 71A and 71B, in a device 840 with a proximal hoop 841, a distal hoop array 842, mirrored V-shaped struts 844, a filter 843 and integral apex 845 it is also possible to include mirrored V-shaped struts 846 between the array of mirrored v-shaped struts 844 to provide a more balanced radial force from the proximal region. This will aid in keeping uniform spacing between the array of connector struts 847 to provide uniform filtration pores when in use in the expanded state.

Referring to FIGS. 72A and 72B a device 850 has a proximal hoop 851, filter elements 852 and paddle supports 855 comprising connector struts 853 and diamond shaped elements 854. The connector struts extend distally from every second distal peak of the proximal hoop and filter elements extending distally from every other distal peak of the proximal hoop. Each connector element may have a diamond, fork, or circular shaped, feature at the distal end to aid deployment accuracy, anti-tilting and resistance to migration. A closed cell shape such as a circle or diamond is advantageous in resistance to perforation because there are no unattached or uncoupled struts that might perforate the vessel. The filter elements and connector struts may be connected to other parts of the proximal hoop provided that they are supplied in an alternating fashion. It is appreciated that the devices of any embodiment can have distal and/or proximal flares to aid in preventing tilting and migration.

Referring to FIGS. 73A-73C a device 860 has a proximal hoop 861, a filter 862, connector struts 863, and a distal hoop

864. The distal supports can be joined together by M-shaped elements extending from each connector strut. Where the connector struts attach to the centre of the M-shaped elements, adjacent M-shaped elements can be coupled together by welding, crimping, fastening or other means. This has the advantage of providing a continuous distal support hoop with the integral filter apex. Referring to FIGS. 74A and 74B it is also possible to provide more than one annular ring at the proximal and/or distal hoops. The device, 870, shown here has a proximal hoop 871, a filter 874, connector struts 872, and a distal hoop 873.

FIGS. 75A-75C show an integral filter device 900 showing plan, elevation and end view with a proximal hoop 901, connector struts 902, distal v-shaped support struts 903, Y-shaped filter elements 904, and an integral apex 905. Each of the filter elements 904 may be supplied as two single filter elements, one V-shaped filter element or one Y-shaped filter element as shown. FIG. 76A illustrates an oblique view of the device and FIG. 76B illustrates a developed view of the device. The filter elements extend from the connector struts to an integral apex at a point distal to the distal peak of the distal V-shaped support struts. The connector struts 902 may have a distal flare at the connection of the filter element as shown in FIGS. 75A-75C and FIG. 76A. The flare may also be initiated proximal to or distal to the filter element connection. The repeating pattern has one Y-shaped filter element alternating with one distal v-shaped support as shown in FIG. 76B. Ideally, this pattern is repeated 3 times but it is appreciated that less or more repetitions are possible. More repetitions will result in more filter elements but will have less radial force. Additional filter elements can also be provided by extending struts proximally from the integral apex between adjacent filter elements 904. The proximal ends of the additional filter elements may be free ended or connected to adjacent filter elements 904, connector struts 902 or v-shaped distal supports 903. The filter element extensions may be connected singularly or through v-shaped connections. Additional filter element extensions will provide reduced filter pore size for a given number of repeating patterns as discussed. Alternatively, a number of filter elements can extend between the integral filter apex and the proximal support hoop 901, the connector struts 902, and/or the v-shaped elements 903. Referring to FIG. 76C, in another embodiment, distally pointing V-shaped filter elements 906 extend between adjacent Y-shaped filter elements 904. This would reduce filter pore size and add a radial force to the filter element where a v-shaped strut is provided. Alternatively, the V-shaped filter elements 906 may point proximally. It is appreciated that filter elements can be reshaped through heat setting during or after expansion of the device in order to provide a more uniform filter pore size.

FIGS. 78A-78D show an integral filter device 950 showing plan, elevation and end views with a proximal support hoop 951, filter elements 952, and paddle supports 953 comprising twin connector struts 954 and diamond shaped elements 955. The twin connector struts extend distally from every second distal peak of the proximal hoop with filter elements extending distally from every other distal peak of the proximal hoop. The proximal and distal ends of the twin connector struts are not connected together having the effect of splitting the proximal support hoop into an array of M-shaped supports and opening the proximal ends of the diamond shaped elements. Each paddle support may have a diamond, fork, or circular shaped feature at the distal end to aid deployment accuracy, anti-tilting and resistance to migration. A closed cell shape such as a circle or diamond is advantageous in resistance to perforation because there are no unattached or uncoupled struts that might perforate the vessel. The filter elements and connector struts may be connected, to other parts of the proximal hoop provided that they are supplied in an alternating fashion. Alternatively, the twin connector struts may be connected, at the proximal and distal ends to form an opening between the connector struts. The twin connector struts may not be close together or parallel as shown.

In another embodiment, referring to FIGS. 79A-79D, an integral filter device 960 is illustrated showing plan, elevation and end views with proximal support paddles 963, filter elements 962, and distal support hoop 961. Paddle supports 963, comprising twin connector struts 964 and diamond shaped elements 965, extend proximally from every second proximal peak of the distal support hoop with filter elements extending distally from the proximal peak of the diamond shaped elements. The proximal and distal ends of the twin connector struts are not connected together having the effect of splitting the distal support hoop into an array of m-shaped supports and opening the diamond shaped elements. Each paddle support may have a diamond, fork, or circular shaped feature at the proximal end to aid deployment accuracy, anti-tilting and resistance to migration. A cell shape such as a circle or diamond is advantageous in resistance to perforation because there are no unattached or uncoupled struts that might perforate the vessel. The number of proximal and distal peaks of the distal support hoop may be reduced while increasing the number of proximal paddle supports and filter elements in order to reduce filter pore size. For example, if the number of distal peaks of the distal support hoop is halved, it is possible to double the number of proximal paddle supports and filter elements. Then, the twin connectors would split the distal support hoop into an array of distally pointing v-shaped supports. The twin connectors do not have to be close together or parallel as shown, it is possible to extend them at angles or through curves along the tubular profile of the device. Proximal and/or distal flares may be included to aid deployment accuracy and resistance to migration. Alternatively, the filter elements and connector struts may be connected to other parts of the paddle supports. In another embodiment, more than one filter element extends from each paddle support. In a further embodiment, the filter is connected to the distal peaks of the distal support hoop and extends distally.

Figure 139:
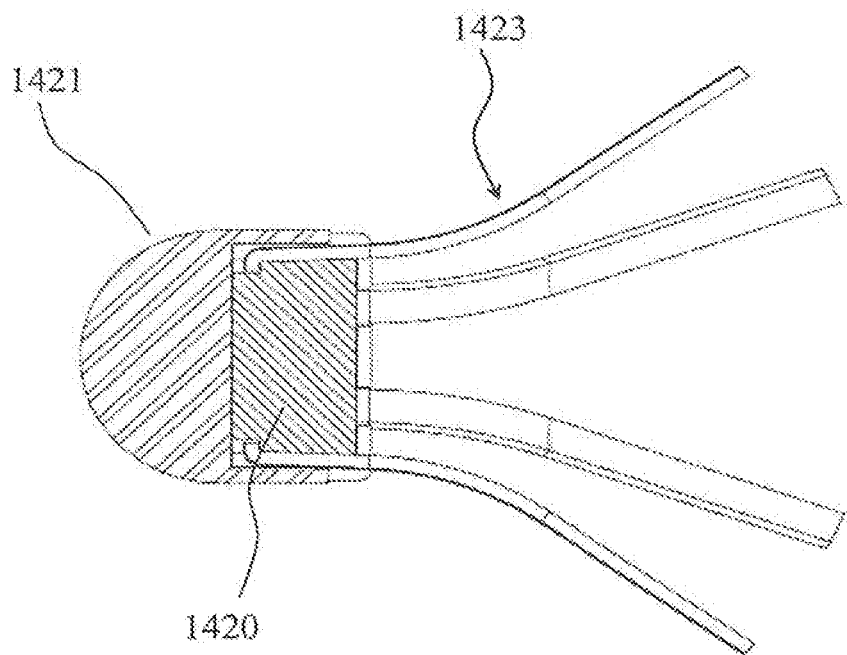

Referring to FIGS. 80 to 139, further holder embodiments are shown that may be employed to secure the filter elements together at their ends to form an apex—refer also to FIGS. 12 to 19. The holders are configured to securely hold the filter elements while reducing overall profile in order to reduce obstruction to blood flow and aid in preventing thrombus formation and/or fibrin growth. These benefits are achieved whether the holder is used with a filter as described above or with a filter of the prior art which terminates in an apex. Also, they may be used with devices of the type in which the filter remains permanently closed, or of the type which opens after a time such as when the holder biodegrades.

FIGS. 80 to 85 depict holders in the form of an overlapping coil or spiral to allow them to be trained through eyelets of the filter element ends and to automatically fasten. It is the type of fastener known as a "cinch" or "key ring" type fastener. The holders are preferably manufactured from wire or tubing that can be threaded through each of a plurality of circumferentially spaced filter element openings.

The drawings show spiral holders with overlapping wire in the axial direction, and some also partly in the radial direction (for example FIG. 82). However, in other embodiments the wire overlaps in a single (radial) plane in the form of a planar spiral holder. In all spiral holder embodiments the wire may be trained through the filter element end eyelets, the holder forming an integral fastener due to contact of juxtaposed spiral turns.

FIG. 80 and shows a holder 1000 with a wire 1001 coiled to overlap by about 50% of a turn. FIG. 81A shows a holder 1005 which overlaps about 110%. The diameter of the holder in FIG. 81A tapers radially outwardly from the proximal end to the distal end while the holder in FIG. 80 has a constant outer diameter. The tapered diameter conforms better to the profile of the eyelets 1011 as shown in FIGS. 81B and 81C-81F. FIG. 82 shows a holder 1050 with 6 overlaps. FIGS. 83 and 84 show holders 1060 and 1065 with only a half coil overlap, and tapered ends of the wire to guide training through the eyelets.

The filter element openings can be machined during laser cutting of the device from raw tubing. To form circumferentially spaced openings with an integral support member, filter elements and filter element openings, the ends of the filter elements should be twisted approximately 90 degrees (the filter element openings will face radially outwardly after laser cutting). Alternatively, filter element openings may be attached to the ends of filter elements.

Preferably, the holder is provided with between 1 and 3 revolutions, more preferably with between 1.2 and 1.8 revolutions, and even more preferably with between 1.4 and 1.6 revolutions. Additional revolutions enhance the security of the cinch preventing the filter element ends from working their way back out of the taurus formed by the cinch. However, excessive revolutions may over-crowd the filter element openings thereby requiring a reduction in the circular/rectangular cross sectional area of the wire/tube that the cinch is formed from in order to fit within a set filter element opening size.

It is preferred that the filter element opening or eyelet is kept small to avoid the need to cut the filter from a larger diameter tube and/or increase the compressed delivery profile of the device. Further, the coiled holder with multiple revolutions will extend through each filter element opening multiple times thereby increasing the complexity of assembly. One or more of the eyelets may include a larger opening to accommodate additional revolutions of holder, for example, where a holder is provided with 1.5 revolutions, the holder will extend once through some of the eyelets and twice through other eyelets. The holder may have a constant diameter at its proximal and distal ends or it may taper radially outwardly from its distal end to its proximal end.

Tapering is advantageous in that the holder will not be strained during use due to the filter elements moving from the compressed delivery profile to the expanded delivery profile as the circumferential space formed by the filter element openings changes from having a substantially constant diameter to having a diameter tapering radially outwardly from the distal end to the proximal end. Alternatively, the cross sectional shape of the holder (circular or rectangular or other) may be reduced to afford additional flexibility to the cinch allowing it to conform to the changing space determined by the filter element, openings when moving from the compressed delivery profile to the expanded in use profile. For cinches cut from raw tubing, it is more difficult to polish the surface of the cinch that resides between overlapping revolutions. This can be aided by increasing the pitch of the revolutions to provide additional space between overlapping revolutions allowing more efficient electro polishing. If it is desired that the space between overlapping revolutions is kept to a minimum for more stability, one of the free ends of the holder provided with an increased pitch may be pulled over the other free end of the cinch after polishing so that overlapping revolutions press against each other and eliminate the space between them. If it is desired that this holder's cross section revolves clockwise from one end to the other, the holder should be manufactured with an anti-clockwise revolution so that after pulling one free end over the other to eliminate the space between overlapping revolutions, the holder changes from revolving anti-clockwise to clockwise.

Figure 81B:
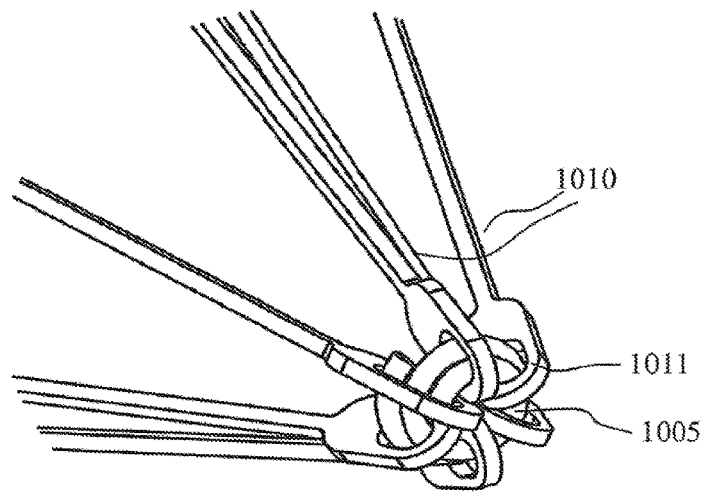
Figure 81C:
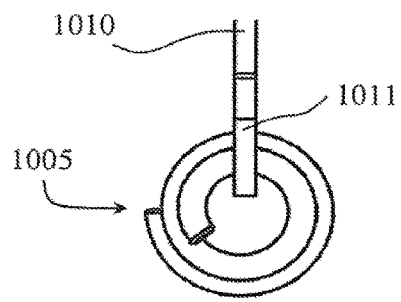
Figure 81D:
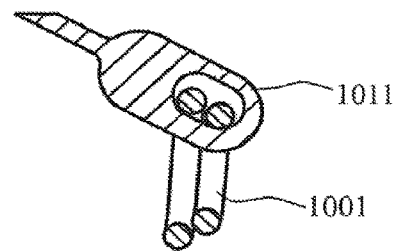
Figure 81E:
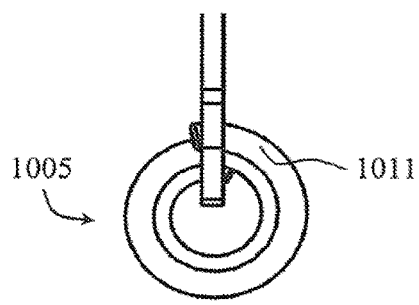
Figure 81F:
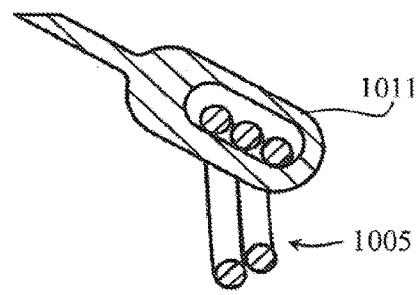

In more detail, FIG. 80 shows a holder 1000 with constant diameter and 1.6 revolutions, formed from wire. FIGS. 81A to 81F show a holder 1005 formed from wire with a tapered diameter and 2.2 revolutions. FIG. 81B shows the cinch 1005 assembled with six filter elements, five of the filter elements have a short opening and one of the filter elements has a long opening as shown in the cross section images in FIGS. 81C and 81D, and 81E and 81F, respectively. Note how the tapered profile of the filter elements matches the tapered profile of the holder 1005. As the tapered profile of the filter elements will vary between the minimum and maximum indicated vessel sizes, the tapered profile of the holder is preferably matched to the tapered profile of the filter elements when constrained in a middle vessel size of the indicated vessel size range—this will minimise wear and enhance durability across the full vessel size range. FIG. 82 shows another holder 1050 manufactured from wire with 5.25 revolutions and a tapered diameter. FIG. 83 shows a holder 1060 cut from raw tubing with 1.45 clockwise revolutions, minimal space between overlapping revolutions, and tapered ends to aid easy threading through eyelets. FIG. 84 shows a holder 1065 cut from raw tubing with 1.45 anti-clockwise revolutions, tapered ends, constant diameter, and with ample space between overlapping revolutions to aid electro polishing—when one free end of the holder is pulled over the other, this holder will resemble the holder shown in FIG. 83. FIG. 85 shows a holder 1070 with 0.9 revolutions that has no overlapping revolutions and therefore forms a taurus with constant cross sectional area. Holders can be manufactured by laser cutting from raw tubing or by forming a length of wire. If made from shape memory material such as Nitinol, the holder can be shape set or alternatively if made from wire without shape memory properties, can be annealed after forming to reduce stresses in the component. The component may also be moulded using a variety of polymer materials.

Referring to FIGS. 86 and 87, clasp holders 1080 and 1090 are shown in which a wire is looped at one end and forms a hook at the other end so that the hook features extend through the loop after threading through the filter element openings to secure in place. These embodiments ensure that the holder wire extends twice through each filter element opening in order to afford additional security should one of the wires fracture during use. Alternatively, the clasp holder 1080 may be provided with only one or with multiple lengths of wire that extend through the filter element openings. The clasp holder may be manufactured by forming shape memory material using a forming tool and heated to set the defined shape. Alternatively, the wire may be mechanically deformed into shape and annealed after to reduce stresses. A flexible biostable or biodegradable filament may also be used having a loop at one end as depicted in FIGS. 86 and 87 where in place of a hook at the other end, a knot is tied, preferably a stopper knot. Alternatively, the filaments may be welded together in a manner that moulds a larger cross section than the eyelet openings to prevent passage there through. The welded end may pass through one of the eyelets more than once where it is welded into an increased cross sectional profile or where a knot is tied in order to form a loop around said eyelet to form an anchor point. This would prevent the filament from becoming an embolus if the filament were biodegradable as the filament would be attached to said eyelet and move to the vessel wall with the eyelet after degradation (for convertible filter embodiment incorporating such a holder design). FIG. 88 depicts a split ring holder 1100 with opposing saw tooth surfaces 1101 and 1102 that inter-engage when the ring is compressed after threading through filter element openings to secure in place. This embodiment may be manufactured using laser or waterjet cutting machines. Alternatively, the holder may be injection moulded. The ring may also be heat set or annealed in its in use closed configuration so that it must be pulled apart in order to assemble with the filter elements. This will reduce the stresses during use as the member will be in its biased state.

FIGS. 89 to 93 show integral band holders in which a free end of a band is threaded through filter element, openings before being threaded back through the other end of the band where features exist to lock the holder in place.

Figure 89:
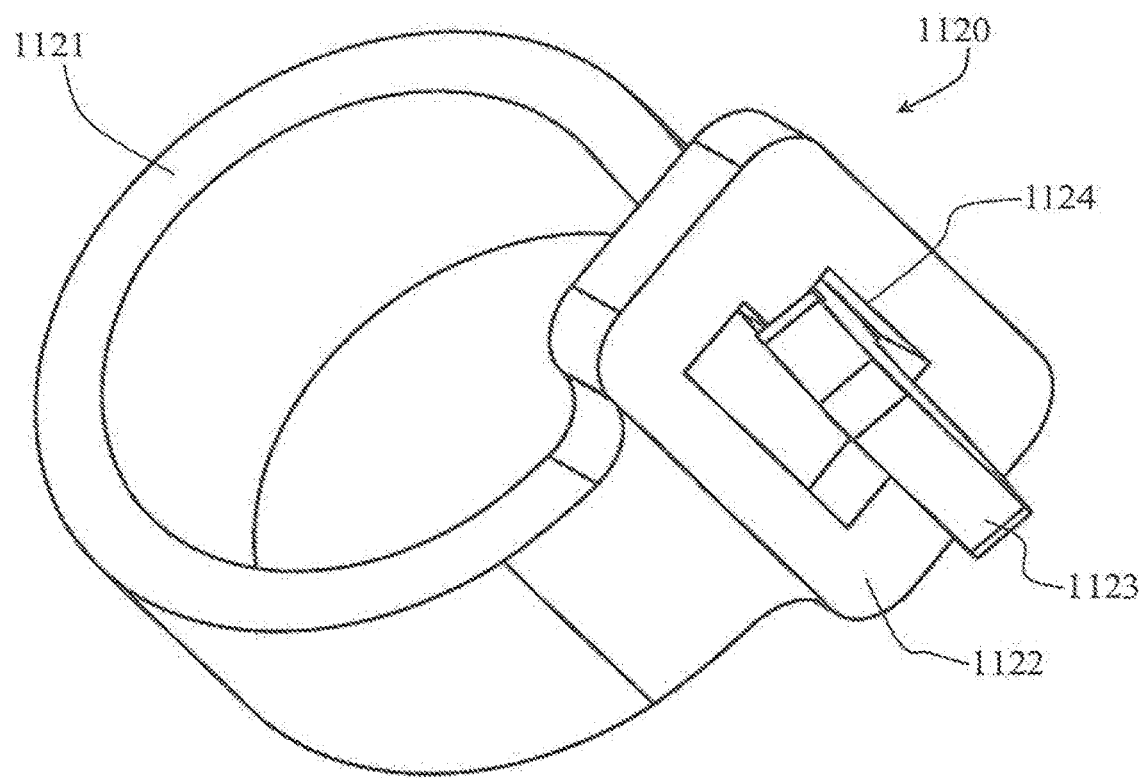
Figure 90:
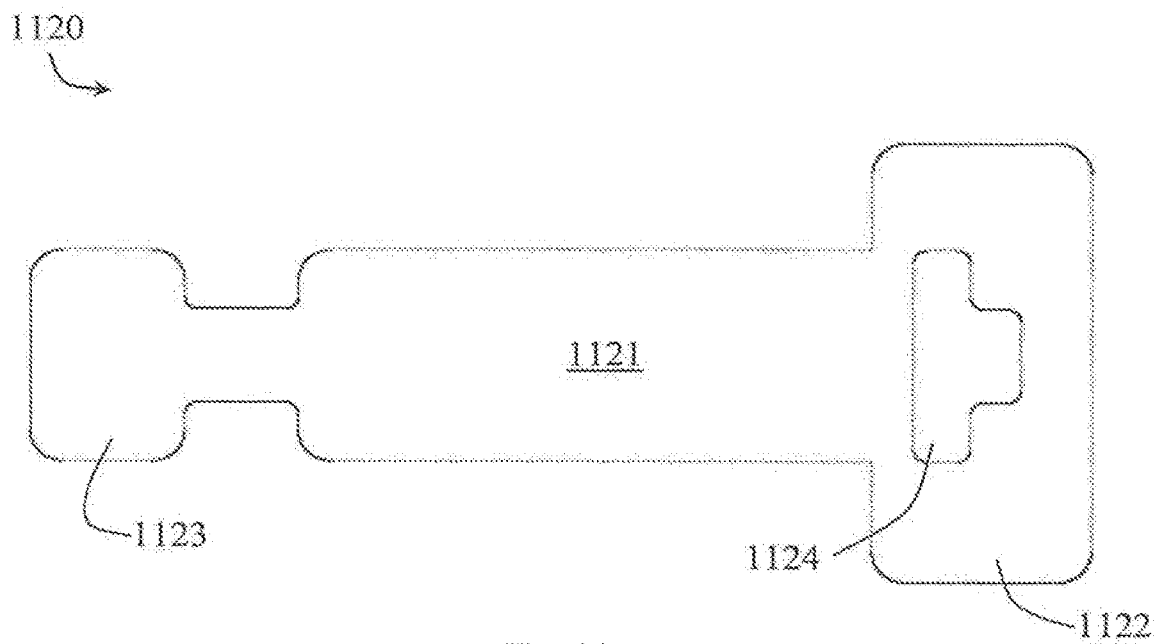
Figure 91:
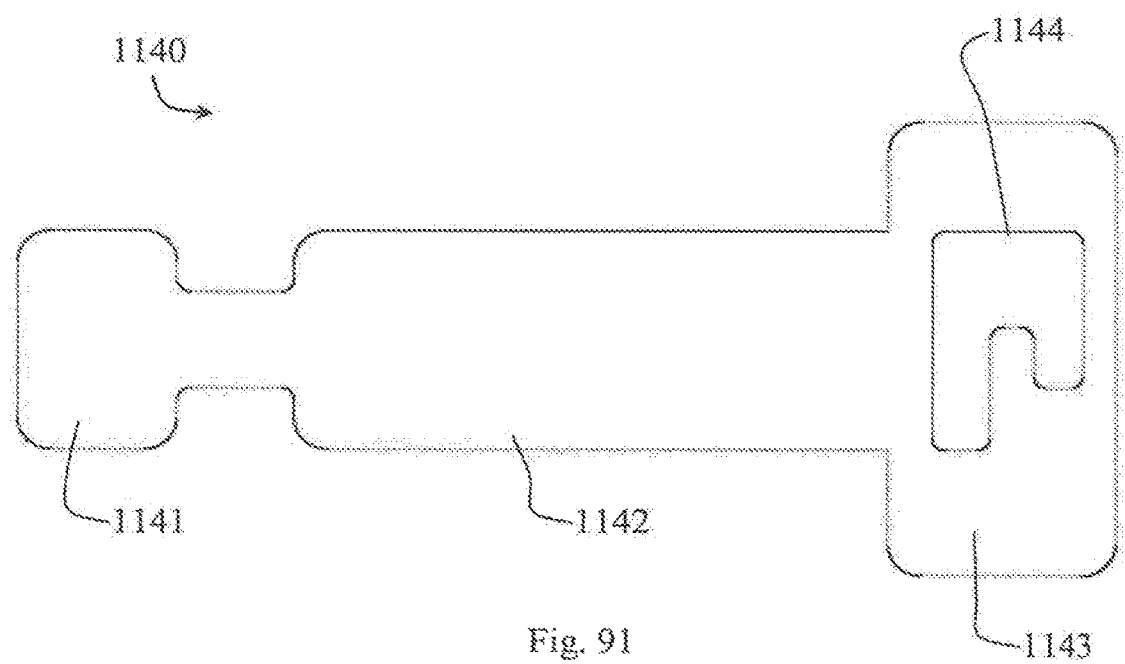

In FIGS. 89 and 90 a holder 1120 has a male connector tab 1123 at one end of a strip 1121 and a female connector tab 1122 with an eyelet 1124 at the other end. In FIG. 91 a holder 1140 has a male end 1141 extending from a strip 1142 and a female end 1143 with a U-shaped eyelet 1144 in which one branch is shorter than the other.

Figure 92:
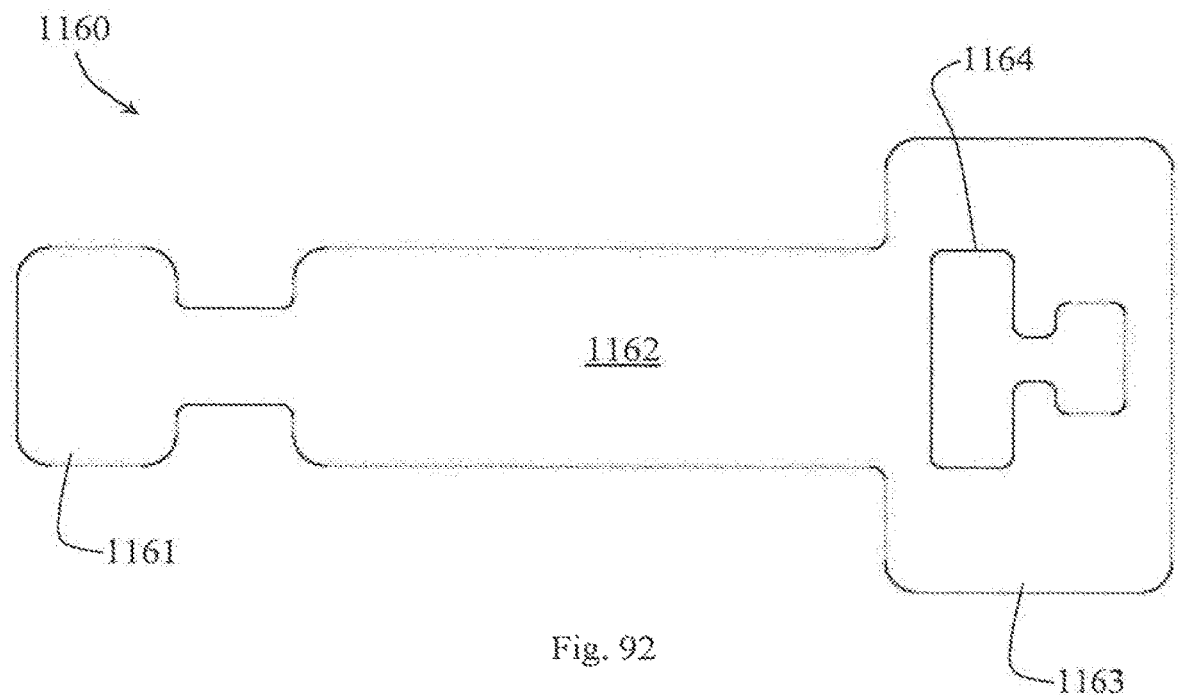

In FIG. 92 a holder 1160 has a male end 1161 extending from a strip 1162 and a female end 1163 with a an eyelet 1164 having openings linked by a bridge.

Figure 93:
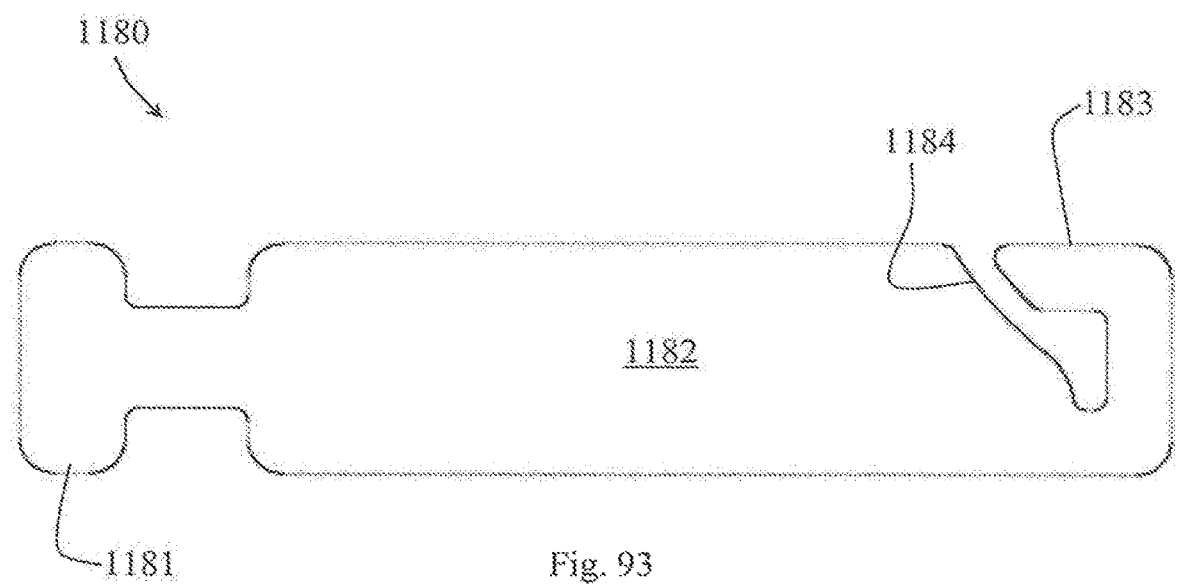

In FIG. 93 a holder 1180 has a male end 1181 extending from a strip 1182 and a female end 1183 with a slot 1184 extending at an angle to the axis of the strip 1182.

Figure 94:
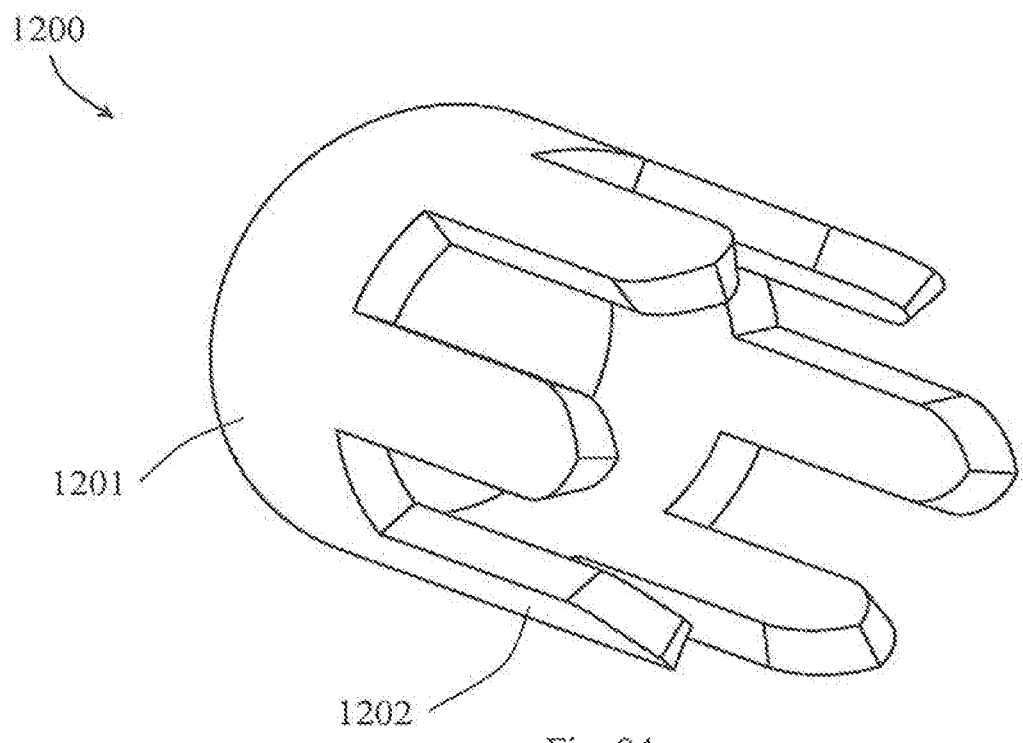
Figure 95:
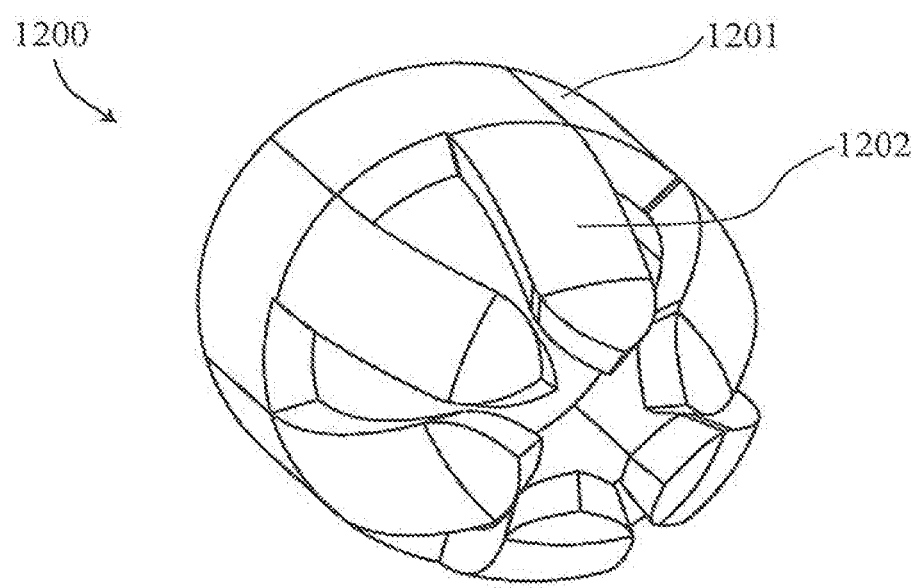
Figure 96:
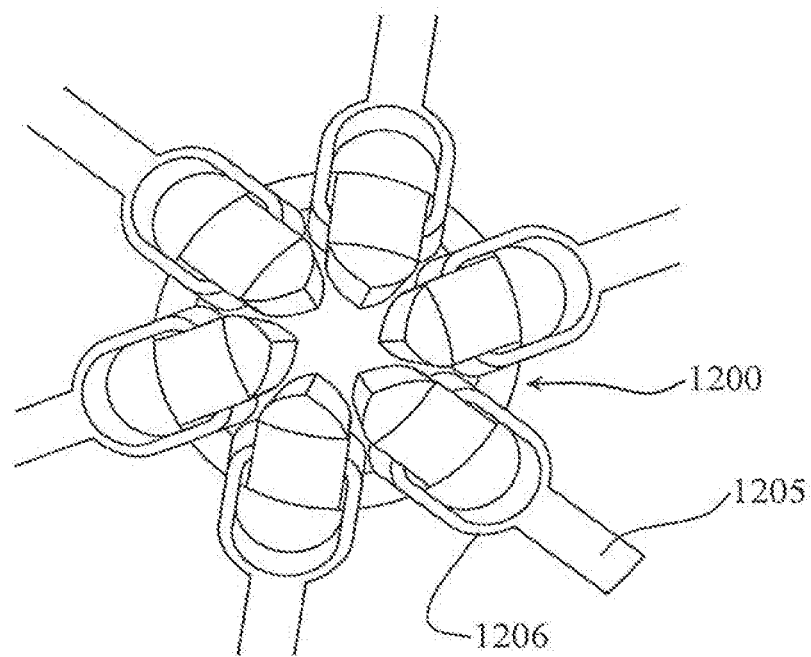
Figure 97:
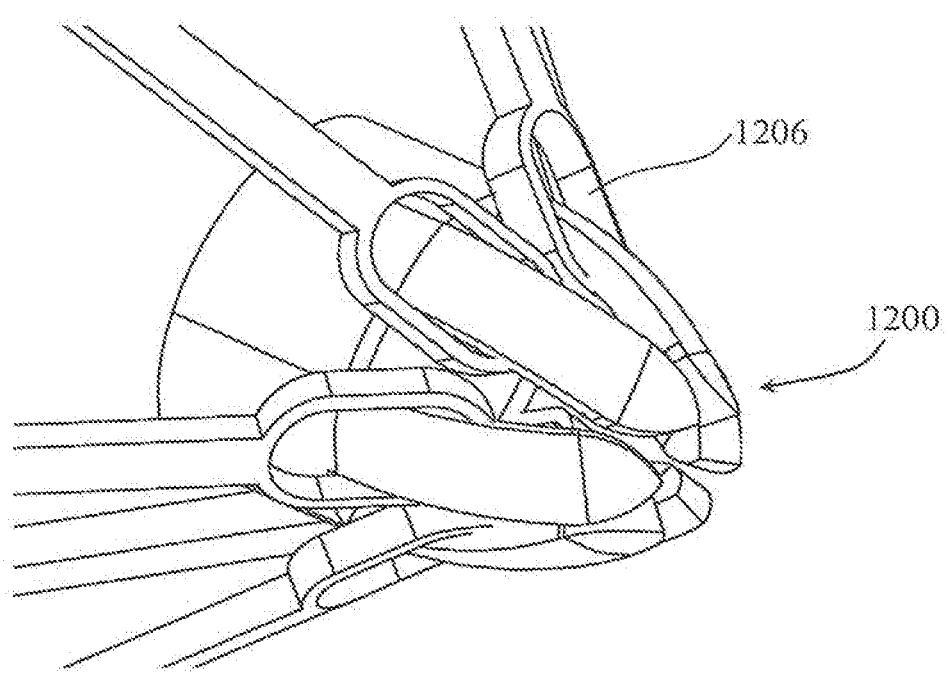

These embodiments may be laser cut from raw tubing, moulded, stamped from sheet metal or otherwise machined. FIG. 93 shows a belt-like holder in which one end is slotted into the other end offering a lower profile than the variations shown in FIGS. 89 to 92 which will reduce obstruction to blood flow and aid in preventing thrombus formation and/or fibrin growth. Additional members may be attached to the band in order to provide the loop and lock features. FIG. 94 to 97 depict a tubular holder 1200 with arms 1202 extending from a ring-shaped base 1201 towards a central apex. Each arm 1202 extends through a filter element opening 1206 providing security in the event that should one holding arm fracture, only one filter element will be affected. The holder 1200 may be laser cut from raw tubing and then heat set with the arms extending towards a central axis. FIG. 94 shows the holder 1200 post laser cutting while FIG. 95 shows it post heat setting. This holder 1200 may be fitted with a hook, preferably on the proximal end, to allow removal using a snare. Alternatively, the holder may be provided with an opening through which a hook member could be threaded through for removal. This would enable the device to be manually opened at a date post implantation should the need for filtration lapse. For this embodiment, the filter element arms should be heat set in a normally open position. The holding arms may extend distally or proximally. The free end of the holder may be fitted with a rounded nose to reduce obstruction to the blood flow preventing thrombus formation and/or fibrin growth. The rounded nose may be integral with the holder or it may be attached. The holder may also be moulded rather than machined from a rod or tubing. Preferably, the holding arms extend distally and the proximal end has an integral rounded nose as this option will have a favourable effect on reducing irregularities in the blood flow.

FIGS. 98 to 102 show a ring type holder 1220 with protrusions 1221 extending radially inwardly. The filter element openings 1225 are threaded into the centre of the holder 1220 before being pushed radially outwardly so that filter element openings are secured on the protrusions. As the filter elements are shape set to be biased radially outwardly of the apex, the filter element openings are unlikely to pop out of the holder 1220, further, the space in the centre of the holder 1220 can be sized so that only one filter element end 1225 can fit in the centre of the holder at any one time.

FIGS. 103 to 105 show a variation in which a holder 1240 has the protrusions 1242 extending from a ring 1241 and are bent distally to provide a resting surface for the filter element 1245 openings thus preventing the filter element ends from popping into the centre of the holder 1240 if the filter element is pushed radially inwardly. Alternatively, the protrusions 1242 may be bent proximally.

A further embodiment is shown in FIGS. 106 to 108 in which a holder 1260 has a ring 1261 from which extend protrusions 1262. The length of the bent protrusions 1262 shown in the previous embodiment is extended to provide additional security against inadvertent removal of one of the filter element ends 1265 from the holder 1260. Yet another holder, 1280, is shown in FIGS. 109 to 112 in which protrusions 1282 extend from a ring 1281 and include ridges or bumps 1283. The ridges 1283 are at least an interference fit with the filter element openings and are preferably sized slightly larger than the filter element openings so that they must be forcibly pushed over the ridge during assembly thereby preventing the filter elements from becoming inadvertently dislodged. A crimping tool may be employed to assemble each of the filter element openings onto each of the ridged protrusions. It will be appreciated that any suitable configuration of ridge or bump that provides a permanent or removable snap fit could also be provided. Alternatively, the protrusions may extend radially outwardly from a central disk as the ridges will hold the filter elements in place.

FIG. 113 to 116 depicts a further holder, 1300, comprising a tubular member 1302 and supporting hooks 1301 to engage with filter element 1305 openings. The hooks 1301 may be integral with the tubular member 1302. The tubular member 1302 may be closed or open in the circumferential direction and may have a polygon or circular cross section. This holder 1300 is advantageous as each filter element 1305 is held separately upon the central tubular member 1302 thereby preventing rubbing between adjacent filter elements 1305. Contacting surfaces may be shaped to mate over a large surface area to distribute contact pressure in order to minimise wear and maximise durability. The holder 1305 may be assembled with the filter elements so that the tubular member faces distally or proximally. The tubular end 1302 of the holder 1300 may be fitted with a hook to facilitate removal using a snare or alternatively, may include an opening through which a hook could be threaded. This would allow conversion of the device from filtering to open should the need arise. In another embodiment, the plurality of hooks 1301 extend from a disk rather than a tube. This holder could be stamped from sheet metal (with hooks flat) and shape set after to curl the hooks after. Either of the holders could be laser cut from tubing or sheet metal, moulded, or machined. Alternatively, the hooks may extend in a curve circumferentially rather than on-axis as shown.

FIGS. 117 to 132 show various split ring holders including circumferential arms that facilitate threading of the filter element openings for securement with circumferentially spaced filter element openings. FIG. 117 to FIG. 120 depict a holder 1320 with a central ring 1321 and two circumferential arms or hooks 1322 and 1323, one extending clockwise and the other extending anti-clockwise. There are preferably six filter element openings (as shown) with three held on the top arm 1322 and three held on the bottom arm 1323. This embodiment provides two holding areas for the filter element openings, however, it is appreciated that one or multiple holding arms may be provided. If desired, one holding arm may be provided for each filter element opening to reduce wear between filter elements and the holder 1320. It is also appreciated that holding arms may all extend clockwise, anti-clockwise, on-axis or various combinations of both. FIGS. 121 to 123 illustrate another holder 1340 in which two circumferential holding arms 1342 and 1343 are connected together by a support arm 1341 that extends through the central axis of the filter device. This embodiment provides more space radially inwardly of the holding arms 1342 and 1343 to facilitate easier assembly.

FIGS. 124 to 126 show a variation of the embodiment shown in FIGS. 121 to 123 where a holder 1360 has hooks 1362 and 1363 with in-turned abutments to prevent the filter elements 1365 from dislodging after assembly. It may be required to twist the ends of the holding arms 1362 and 1363 into each of the filter element openings; however, this further secures the filter elements to the holder 1360 as there will be no twisting forces applied to the filter elements during use.

Alternatively, the abutments may extend radially outwardly or axially as shown in FIGS. 127 to 129. In these drawings a holder 1380 has a central arm 1381 from which extend two hooks 1382 and 1383, with axial extensions 1383 and 1385 respectively pointing in the same direction. However, it is appreciated that axial extensions 1383 and 1385 may extend in opposite directions. In another embodiment where the holder is formed from wire, the axial extensions have excessive length (for example—100 mm) to aid in threading the holder through filter element eyelets (a longer length can be held by hand rather than with a tweezers enhancing ease of assembly), after assembly the extensions can be cut to any desired length, preferably less than 3 mm. It is appreciated that a sacrificial length of material may be included with any of the holders disclosed. This is especially true for holders manufactured from wire as one only needs to postpone trimming the additional length until after assembly. For holders laser cut from tubing, this would required a substantial amount of additional laser cutting and raw tubing material—therefore, such a sacrificial length is not as desirable for laser cut embodiments.

FIGS. 130 to 132 show a holder 1400 is in the form of a single holding arm with abutments 1401 extending radially inwardly at either end. The extensions 1401 form a non re-entrant opening 1402 so that the holder 1400 can securely engage the filter element 1405 eyelets. Alternatively, the abutments may extend radially outwardly, on-axis, or a combination for either.

FIGS. 133 to 139 depict another holder 1420 including a central hub 1420 and an outer housing 1421. The hub 1420 includes recesses 1422 for each of the filter elements 1423 and the housing 1421 engages with the hub 1420 to lock the filter elements within the holder. The filter element 1423 ends may be fitted with openings or hooks to afford a mechanical abutment between the hub and filter element ends.

It is preferred that the holder of the various embodiments interlock the filter element ends together in a way that minimises movement of the filter elements relative to the holder—this will minimise the extent of wear, thus enhancing durability. The preferred internal diameter of the holder is between 0.4 mm and 3.0 mm, more preferably between 0.6 mm and 1.2 mm, and even more preferably between 0.8 and 1.0 mm. If the holder is sized so that the ends of the filter elements are held tightly together, there will be negligible movement between filter element ends and the holder. Instead, the filter element ends and holder will move together as an assembly.

The invention is not limited to the embodiments described but may be varied in construction and detail. The invention may be manufactured from materials including but not limited to Nitinol, stainless steel, cobalt chromium, biodegradable materials, and/or implantable polymeric.

The proximal support hoops may be of sinusoid, crown, or zigzag construction. The proximal and/or distal supports may include more than one sinusoid, crown, zigzag construction, or paddle support.

The filter elements may be shaped to provide a more uniform filter pore size than straight filter elements. The filter cones of the devices presented are intended to point distally in a blood vessel in order capture clot centrally in the vessel where lysis, the physiological process in which the captured clots are broken down in the body, is optimum. It is appreciated that the devices may be alternatively positioned with the filter cones pointing proximally in order to capture clot in an annular region at the vessel wall.

The support frames of the present invention may be fitted with barb or hook features to further reduce the likelihood of migration.

The devices disclosed herein may be manufactured of wire material. The devices disclosed herein may be manufactured of multiple pieces and jointed later.

The invention is not limited to the embodiments described but may be varied in construction and detail.

The holders may be made of biodegradable material in order to afford convertible properties to the device if desired where the filter elements move from a closed filtering position to an open position with unobstructed blood flow after a predetermined period of time.

The integral filter apex arrangements may be modified to have free ends and include openings for reception of a biodegradable holder in order to supply the support frames in embodiments where the filter elements are movable from a closed filtering position to an open position with unrestricted blood flow.

The invention claimed is:

1. A vascular filter device comprising a support frame and filter elements, the filter elements having a first configuration and a second configuration,
    the filter elements extending from the support frame towards filter element ends forming an apex at which they are interconnected in the first configuration,
    wherein said apex is located at or near a central axis of the vascular filter device in the first configuration; and
    wherein the filter elements are biased such that if unconnected from the apex the filter element ends are located at radial positions between the radial positions of the support frame and said central axis when the vascular filter device is otherwise unconstrained in a second configuration.

2. The vascular filter device as claimed in claim 1, wherein the support frame and the filter elements are formed integrally.

3. The vascular filter device as claimed in claim 1, wherein the support frame and the filter elements are formed from NiTi.

4. The vascular filter device as claimed in claim 1, wherein filter element unconnected positions are provided by filter element shapes and angles at which they extend from the support frame.

5. The vascular filter device as claimed in claim 1, wherein the filter elements have unconnected positions if unconnected such that the filter element ends are located approximately 10% to 50% of a distance from the central axis to the support frame.

6. The vascular filter device as claimed in claim 5, wherein the unconnected positions are is approximately 15% to 40% of said distance.

7. The vascular filter device as claimed in claim 1, wherein the vascular filter device has an indicated vessel size range, and
  wherein the filter elements are biased to have positions if unconnected such that:
  a. when the vascular filter device is constrained in a vessel which lies in an upper subrange of said indicated vessel size range, the filter element ends are between the central axis and the support frame,
  b. when the vascular filter device is constrained in a vessel which lies in a central subrange of said indicated vessel size range the filter element ends are approximately on the central axis, and
  c. when the vascular filter device is constrained in a vessel which lies in a lower sub-range of said indicated vessel size range the filter element ends extend through said central axis.

8. The vascular filter device as claimed in claim 7, wherein the filter elements have similar maximum strains in situations (a) and (c) when the filter element ends are interconnected.

9. The vascular filter device as claimed in claim 7, wherein the filter elements have approximately equal maximum tensile strains in situations (a) and (c) when the filter element ends are interconnected.

10. The vascular filter device as claimed in claim 1, wherein the support frame comprises a proximal hoop, a distal hoop, and interconnecting struts.

11. The vascular filter device as claimed in claim 10, wherein the proximal hoop has peaks and the filter elements are connected to the support frame at or adjacent distal peaks of the proximal hoop.

12. The vascular filter device as claimed in claim 1, wherein the filter element ends, the filter elements, and the support frame are formed integrally from one piece.

13. The vascular filter device as claimed in claim 1, wherein the filter element ends are formed integrally to provide an integral apex.

14. The vascular filter device as claimed in claim 1, wherein the filter element ends are interconnected by a holder.

15. The vascular filter device as claimed in claim 14, wherein at least some filter elements have eyelets and the holder is trained through the eyelets.

16. The vascular filter device as claimed in claim 14, wherein the holder has an integral fastener.

17. The vascular filter device as claimed in claim 16, wherein the holder has a form of a spiral in which spiral turns are in contact or in close proximity with each other to provide the integral fastener.

18. The vascular filter device as claimed in claim 17, wherein the holder is in the form of a planar spiral in which the spiral turns overlap in a radial direction.

19. The vascular filter device as claimed in claim 18, wherein the holder is in the form of a three-dimensional spiral in which the spiral turns overlap at least partly in an axial direction.

20. The vascular filter device as claimed in claim 19, wherein an outer diameter of the holder is tapered axially.

* * * * *